United States Patent
Connor et al.

(10) Patent No.: US 6,458,781 B1
(45) Date of Patent: **\*Oct. 1, 2002**

(54) SUBSTITUTED DIARYLALKYL AMIDES AS CALCIUM CHANNEL ANTAGONISTS

(76) Inventors: David Thomas Connor, 2453 Antietam, Ann Arbor, MI (US) 48105; Lain-Yen Hu, 4881 S. Ridgeside Cir., Ann Arbor, MI (US) 48105; Thomas Charles Malone, 45139 N. Spring Dr., Canton, MI (US) 48187; Michael Francis Rafferty, 3711 Rolling Ridge Ct., Ann Arbor, MI (US) 48105; Bruce David Roth, 49255 Hunt Club Ct., Plymouth, MI (US) 48170; Todd Robert Ryder, 521 N. Ashley St., Ann Arbor, MI (US) 48103; Anthony Denver Sercel, 2424 Nixon Rd., Ann Arbor, MI (US) 48105; Yuntao Song, 4065 Spring Lake Blvd., Ann Arbor, MI (US) 48108

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/403,579
(22) PCT Filed: Mar. 31, 1999
(86) PCT No.: PCT/US99/07133
§ 371 (c)(1),
(2), (4) Date: Oct. 25, 1999
(87) PCT Pub. No.: WO99/55688
PCT Pub. Date: Nov. 4, 1999

Related U.S. Application Data

(60) Provisional application No. 60/083,141, filed on Apr. 27, 1998.

(51) Int. Cl.$^7$ .................... C07D 295/20; C07D 209/34; C07D 295/12; C07D 231/56; C07C 237/06
(52) U.S. Cl. .............................. 514/212.03; 514/239.2; 514/255.1; 514/453; 514/485; 514/522; 514/524; 514/617; 514/630; 540/529; 544/175; 544/391; 546/226; 549/356; 558/414; 560/27; 564/164; 564/168; 564/195
(58) Field of Search .......................... 558/414; 560/27; 564/164, 168, 195; 540/529; 544/391, 175; 549/356; 546/226; 514/212.03, 239.2, 255.1, 453, 485, 522, 524, 617, 630

(56) References Cited

U.S. PATENT DOCUMENTS

| | | | |
|---|---|---|---|
| 4,596,803 A | 6/1986 | Masaki et al. ............... 514/252 |
| 4,822,775 A | * 4/1989 | Hansen, Jr. et al. .......... 514/19 |
| 5,399,570 A | * 3/1995 | Klingler et al. ............. 514/327 |

FOREIGN PATENT DOCUMENTS

| | | |
|---|---|---|
| EP | 0 333 938 | 11/1988 |
| EP | 0 805 147 A1 | 5/1997 |
| WO | 96/05201 | 2/1996 |
| WO | 96/40747 | 12/1996 |

OTHER PUBLICATIONS

Mueller et al., WO 97/46511 (Abstract), 1997.*

Giudicelli et al. FR 2279383 (Abstract), 1976.*

Bolos et al. (J. Med. Chem. 1996, 39, 2962–2970).*

Kwapiszewski et al. (Acta Pol. Pharm. (1977), 34(5), 459–62).*

Kwapiszewski et al. (Acta Pol. Pharm. (1977), 34(4), 371–5).*

Kwapiszewski et al. (Acta Pol. Pharm. (1977), 34(3), 261–6).*

* cited by examiner

*Primary Examiner*—Bruck Kifle
(74) *Attorney, Agent, or Firm*—Todd M. Crissey; David R. Kurlandsky; Charles W. Ashbrook

(57) ABSTRACT

The present invention provides compounds that block calcium channels and have the Formula I:

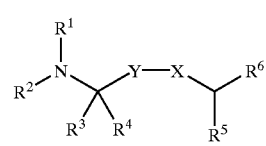

The present invention also provides pharmaceutical compositions containing the compounds of Formula I and methods of using them to treat stroke, cerebral ischemia, head trauma, and epilepsy.

20 Claims, No Drawings

SUBSTITUTED DIARYLALKYL AMIDES AS CALCIUM CHANNEL ANTAGONISTS

This application claims the benefit of provisional application No. 60/083,141, filed Apr. 27, 1998.

FIELD OF THE INVENTION

The present invention relates to compounds that act to block calcium channels; methods of using the compounds to treat stroke, cerebral ischemia, pain, head trauma or epilepsy; and to pharmaceutical compositions that contain the compounds of the present invention.

SUMMARY OF THE RELATED ART

The entry of excessive amounts of calcium ions into neurons following an ischemic episode or other neuronal trauma has been well-documented. Uncontrolled high concentrations of calcium in neurons initiates a cascade of biochemical events that disrupts normal cellular processes. Among these events are the activation of proteases and lipases, breakdown of neuronal membranes and the formation of free radicals, which may ultimately lead to cell death. Several types of calcium channels have been discovered and called the L, N, P, Q, R, and T types. Each type possesses distinct structural features, functional properties and cellular/subcellular distributions. Type selective calcium channel blockers have been identified. For example, SNX-111 has been shown to be a selective N-type calcium channel blocker and has demonstrated activity in a number of models of ischemia and pain (Bowersox S. S., et al., *Drug News and Perspective*, 1994;7:261–268 and references cited therein). The compounds of the present invention are calcium channel blockers that can block N-type calcium channels and can be used to treat stroke, pain, cerebral ischemia, head trauma, and epilepsy.

Certain benzhydryl amides and benzhydryl amines have been described in the past, but their methods of use have been different from those of the present invention. For instance, U.S. Pat. No. 4,596,803 disclosed the following compound for the treatment of cardiac problems, with no mode of action specified:

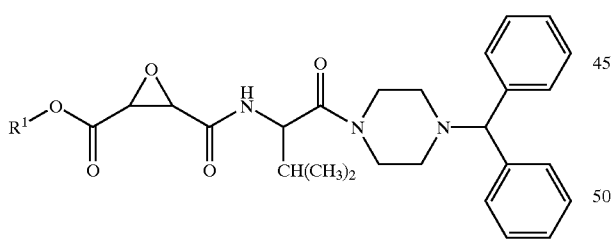

European Patent Publication 333,938 refers to compounds having beta blocking activity for use in treatment of cardiovascular disorders. World Patent Publication 96/05201 refers to imidazopyridine derivatives as dual histamine and platelet activating factor antagonists. U.S. Pat. No. 4,764,514 refers to an oxothiazolidine compound. Other benzhydryl amides are mentioned in *Acta. Polon. Pharm.* 34(4):371–375; 34(5):459–463; and 39(3):261–266. None of these earlier compounds have been used as N-type calcium channel blockers as described in the present invention.

The compounds of the present invention are not homologs or positional isomers of the compounds specified by Masaki et al.; therefore, one skilled in the art could not predict if these compounds would have similar biological activities.

SUMMARY OF THE INVENTION

The present invention provides compounds having the structural Formula I

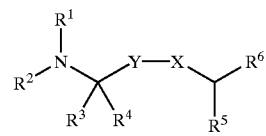

or the pharmaceutically acceptable salts, thereof, wherein:

X is —NH(CH$_2$)$_n$—

Y is 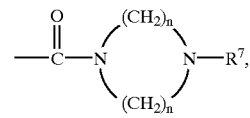

each $R^1$ and $R^2$ are independently hydrogen, $C_1$–$C_6$ alkyl, $C_2$–$C_6$ alkenyl,

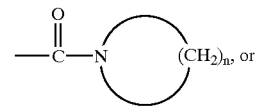

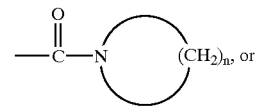

$R^1$ and $R^2$ together with the nitrogen atom to which they are both attached form a heterocycloalkyl group;

$R^3$ is hydrogen, $C_1$–$C_6$ alkyl, phenyl, substituted phenyl, benzyl, substituted benzyl, or —(CH$_2$)$_n$—$C_3$–$C_7$ cycloalkyl;

$R^4$ is hydrogen or $C_1$–$C_6$ alkyl;

or $R^3$ and $R^4$ together with the carbon atom to which they are attached form a $C_3$–$C_7$ cycloalkyl ring;

each $R^5$ and $R^6$ are independently phenyl or substituted phenyl;

$R^7$ is $C_1$–$C_6$ alkyl, phenyl, or heterocycloalkyl; and each n is independent 0 to 6.

In another preferred embodiment,
R¹ is hydrogen and

R² is 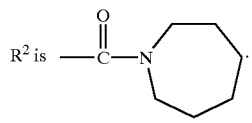.

In another preferred embodiment, R³ is hydrogen and R⁴ is 2-methylpropyl.

In another preferred embodiment, R⁵ and R⁶ are 4-fluorophenyl.

In another preferred embodiment, X is —NHCH₂CH₂CH₂—.

In another preferred embodiment, R⁵ and R⁶ are phenyl.

In another preferred embodiment, R⁵ and R⁶ are 4-fluorophenyl or phenyl;
X is —NHCH₂CH₂CH₂—;
R³ is hydrogen; and
R⁴ is 2-methylpropyl.

In a preferred embodiment of the compounds of Formula I,
X is

R¹ is hydrogen;
R² is

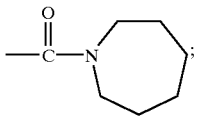

and
R⁵ and R⁶ are 4-fluorophenyl or phenyl.

The present invention provides the compound (S)-Azepane-1-carboxylic acid {3-methyl-1-[3-(1-methyl-2-oxo-3-phenyl-2,3-dihydro-1H-indol-3-yl)-propylcarbamoyl]-butyl}-amide.

The present invention provides the compound (S)-Azepane-1-carboxylic acid {3-methyl-1-[(1-phenyl-1H-indazol-3-ylmethyl)-carbamoyl]-butyl}-amide.

The present invention provides the compound (S)-Azepane-1-carboxylic acid {1-[4-(9H-fluoren-9-yl)-piperazine-1-carbonyl]-3-methyl-butyl}-amide.

The present invention provides the compound (S)-(1-{4-[Bis-(4-fluoro-phenyl)-methyl]-piperazin-1-ylmethyl}-3-methyl-butyl)-carbamic acid tert-butyl ester.

The present invention provides the compound (S)-Azepane-1-carboxylic acid (1-{4-[bis-(4-fluoro-phenyl)-methyl]-piperazin-1-ylmethyl}-3-methyl-butyl)-amide.

The present invention provides the compound (S)-Azepane-1-carboxylic acid [1-(benzhydryl-carbamoyl)-3-methyl-butyl]-amide.

The present invention provides the compound (S)-Azepane-1-carboxylic acid [1-(2,2-diphenyl-ethylcarbamoyl)-3-methyl-butyl]-amide.

The present invention also provides the compounds:

(S)-Azepane-1-carboxylic acid {1-[4,4-bis-(4-fluoro-phenyl)-butylcarbamoyl]-3-methyl-butyl}-amide;
(R)-Azepane-1-carboxylic acid {1-[4,4-bis-(4-fluoro-phenyl)-butylcarbamoyl]-3-methyl-butyl}-amide;
(S)-Azepane-1-carboxylic acid [1-(3,3-diphenyl-propylcarbamoyl)-3-methyl-butyl]-amide;
(S)-{1-[4,4-Bis-(4-fluoro-phenyl)-butylcarbamoyl]-3-methyl-butyl}-carbamic acid tert-butyl ester;
(S)-2-Amino-4-methyl-pentanoic acid [4,4-bis-(4-fluoro-phenyl)-butyl]-amide;
(S)-2-(Cyclohexylmethyl-amino)-4-methyl-pentanoic acid [4,4-bis-(4-fluoro-phenyl)-butyl]-amide;
(S)-4-Methyl-2-(3-methyl-but-2-enylamino)-pentanoic acid [4,4-bis-(4-fluoro-phenyl)-butyl]-amide;
(S)-4-Methyl-2-methylamino-pentanoic acid [4,4-bis-(4-fluoro-phenyl)-butyl]-amide;
(S)-4-Methyl-2-[methyl-(3-methyl-but-2-enyl)-amino]-pentanoic acid [4,4-bis-(4-fluoro-phenyl)-butyl]-amide;
(S)-2-[(4-tert-Butyl-benzyl)-methyl-amino]-4-methyl-pentanoic acid [4,4-bis-(4-fluoro-phenyl)-butyl]-amide;
(S)-2-Cyclohexylamino-4-methyl-pentanoic acid [4,4-bis-(4-fluoro-phenyl)-butyl]-amide;
(S)-Azepane-1-carboxylic acid {1-[4,4-bis-(4-fluoro-phenyl)-butylcarbamoyl]-2-methyl-butyl}-amide;
(S)-4-Phenyl-piperazine-1-carboxylic acid {1-[4,4-bis-(4-fluoro-phenyl)-butylcarbamoyl]-3-methyl-butyl}-amide;
(S)-4-Methyl-2-(tetrahydro-pyran-4-ylamino)-pentanoic acid [4,4-bis-(4-fluoro-phenyl)-butyl]-amide;
(S)-2-Isopropylamino-4-methyl-pentanoic acid [4,4-bis-(4-fluoro-phenyl)-butyl]-amide;
(S)-2-Dimethylamino-4-methyl-pentanoic acid [4,4-bis-(4-fluoro-phenyl)-butyl]-amide;
(S)-2-(Cyclohexyl-methyl-amino)-4-methyl-pentanoic acid [4,4-bis-(4-fluoro-phenyl)-butyl]-amide;
(S)-4-Methyl-2-piperidin-1-yl-pentanoic acid [4,4-bis-(4-fluoro-phenyl)-butyl]-amide;
(S)-4-Methyl-2-morpholin-4-yl-pentanoic acid [4,4-bis-(4-fluoro-phenyl)-butyl]-amide;
(S)-4-Methyl-2-piperidin-1-yl-pentanoic acid (3,3-diphenyl-propyl)-amide;
(S)-2-(Cyclohexyl-methyl-amino)-4-methyl-pentanoic acid (3,3-diphenyl-propyl)-amide;
(S)-Azepane-1-carboxylic acid {1-[4,4-bis-(4-fluoro-phenyl)-butylcarbamoyl]-2-methyl-propyl}-amide;
(S)-4-Methyl-2-[methyl-(tetrahydro-pyran-4-yl)-amino]-pentanoic acid [4,4-bis-(4-fluoro-phenyl)-butyl]-amide;
(S)-4-Methyl-2-[methyl-(3-methyl-butyl)-amino]-pentanoic acid [4,4-bis-(4-fluoro-phenyl)-butyl]-amide;
(S)-4-Methyl-piperazine-1-carboxylic acid {1-[4,4-bis-(4-fluoro-phenyl)-butylcarbamoyl]-3-methyl-butyl}-amide;
(S)-Azepane-1-carboxylic acid {1-[4,4-bis-(4-fluoro-phenyl)-butylcarbamoyl]-ethyl}-amide;
(S)-Azepane-1-carboxylic acid (1-{4-[bis-(4-fluoro-phenyl)-methyl]-piperazine-1-carbonyl}-3-methyl-butyl)-amide;
(S)-Azepane-1-carboxylic acid (2-{4-[bis-(4-fluoro-phenyl)-methyl]-piperazin-1-yl}-2-oxo-ethyl)-amide;
(S)-Azepane-1-carboxylic acid (1-{4-[bis-(4-fluoro-phenyl)-methyl]-piperazine-1-carbonyl)-2-methyl-propyl)-amide;
(R)-Azepane-1-carboxylic acid (1-{4-[bis-(4-fluoro-phenyl)-methyl]-1-piperazine-1-carbonyl}-3-methyl-butyl)-amide;
(S)-1-{4-[Bis-(4-fluoro-phenyl)-methyl]-piperazin-1-yl}4-methyl-2-piperidin-1-yl-pentan-1-one;
(S)-1-{4-[Bis-(4-fluoro-phenyl)methyl]-piperazin-1-yl}-2-cyclohexylamino-4-methyl-pentan-1-one;
(S)-1-{4-[Bis-(4-fluoro-phenyl)-methyl]-piperazin-1-yl}-2-dimethylamino-4-methyl-pentan-1-one;

(S)-1-{4-[Bis-(4-fluoro-phenyl)-methyl]-piperazin-1-yl}-2-(cyclohexyl-methyl-amino)-4-methyl-pentan-1-one;
(S)-1-{4-[Bis-(4-fluoro-phenyl)-methyl]-piperazin-1-yl}-4-methyl-2-[methyl-(tetrahydro-pyran-4-yl)-amino]-pentan-1-one;
(S)-1-{4-[Bis-(4-fluoro-phenyl)-methyl]-piperazin-1-yl}-4-methyl-2-morpholin-4-yl-pentan-1-one;
(S)-Azepane-1-carboxylic acid (1-{4-[bis-(4-fluoro-phenyl)-methyl]-piperazine-1-carbonyl}-2-methyl-butyl)-amide;
(S)-4-Phenyl-piperazine-1-carboxylic acid (1-{4-[bis-(4-fluoro-phenyl)-methyl]-piperazine-1-carbonyl}-3-methyl-butyl)-amide;
1-{4-[Bis-(4-fluoro-phenyl)-methyl]-piperazin-1-yl}-4-methyl-2-[methyl-(3-methyl-butyl)-amino]-pentan-1-one;
(S)-4-Methyl-piperazine-1-carboxylic acid (1-{4-[bis-(4-fluoro-phenyl)-methyl]-piperazine-1-carbonyl}-3-methyl-butyl)-amide;
(S)-Azepane-1-carboxylic acid [1-(4-benzhydryl-piperazine-1-carbonyl)-3-methyl-butyl]-amide;
(S)-1-{4-[Bis-(4-fluoro-phenyl)-methyl]-piperazin-1-yl}-2-isopropylamino-4-methyl-pentan-1-one;
(S)-(1-{4-[Bis-(4-fluoro-phenyl)-methyl]-piperazine-1-carbonyl}-3-methyl-butyl)-carbamic acid tert-butyl ester;
(S)-(1-Benzyl-2-{4-[bis-(4-fluoro-phenyl)-methyl]-piperazin-1-yl}-2-oxo-ethyl)-carbamic acid tert-butyl ester;
(S)-2-Amino-1-{4-[bis-(4-fluoro-phenyl)-methyl]-piperazin-1-yl}-3-phenyl-propan-1-one;
(S)-2-Amino-1-{4-[bis-(4-fluoro-phenyl)-methyl]-piperazin-1-yl}-4-methyl-pentan-1-one;
(S)-1-{4-[Bis-(4-fluoro-phenyl)-methyl]-piperazin-1-yl}-2-isopropylamino-3-phenyl-propan-1-one;
(S)-1-{4-[Bis-(4-fluoro-phenyl)-methyl]-piperazin-1-yl}-2-(3-methyl-butylamino)-3-phenyl-propan-1-one;
(S)-1-{4-[Bis-(4-fluoro-phenyl)-methyl]-piperazin-1-yl}-2-[bis-(3-methyl-butyl)-amino]-3-phenyl-propan-1-one;
(S)-2-[Bis-(4-tert-butoxy-benzyl)-amino]-1-{4-[bis-(4-fluoro-phenyl)-methyl]-piperazin-1-yl}4-methyl-pentan-1-one;
1-{4-[Bis-(4-fluoro-phenyl)-methyl]-piperazin-1-yl}-2-(4-tert-butyl-benzylamino)-4-methyl-pentan-1-one;
(S)-2-[Bis-(4-tert-butyl-benzyl)-amino]-1-{4-[bis-(4-fluoro-phenyl)-methyl]-piperazin-1-yl}-4-methyl-pentan-1-one;
1-{4-[Bis-(4-fluoro-phenyl)-methyl]-piperazin-1-yl}-4-methyl-2-(3,4,5-trimethoxy-benzylamino)-pentan-1-one;
1-{4-[Bis-(4-fluoro-phenyl)-methyl]-piperazin-1-yl}-2-cyclohexylamino-3-phenyl-propan-1-one;
S-2-Benzylamino-1-{4-[bis-(4-fluoro-phenyl)-methyl]-piperazin-1-yl}-4-methyl-pentan-1-one;
S-1-{4-[Bis-(4-fluoro-phenyl)-methyl]-piperazin-1-yl}-4-methyl-2-(tetrahydro-pyran-4-ylamino)-pentan-1-one;
S-1-{4-[Bis-(4-fluoro-phenyl)-methyl]-piperazin-1-yl}-2-(4-tert-butoxy-benzylamino)-4-methyl-pentan-1-one;
S-N-[4,4-Bis-(4-fluoro-phenyl)-butyl]-2-isopropylamino-3-methyl)-butyramide;
S-N-[4,4-Bis-(4-fluoro-phenyl)-butyl]-2-sec-butylamino-3-methyl)-butyramide;
S-{4-[4,4-Bis-(4-fluoro-phenyl)-butylcarbamoyl]-4-tert-butoxycarbonylamino-butyl}-carbamic acid tert-butyl ester;
S-2-(Isopropyl-methyl-amino)-4-methyl-pentanoic acid [4,4-bis-(4-fluoro-phenyl)-butyl]-amide;
S-N-[4,4-Bis-(4-fluoro-phenyl)-butyl]-2-(cyclohexyl-methyl-amino)-3-methyl-butyramide;
S-N-[4,4-Bis-(4-fluoro-phenyl)-butyl]-2-cyclohexylamino-3-methyl-butyramide;
(R)-4-methyl-2-methylamino-pentanoic acid [4,4-bis-(4-fluorophenyl)-butyl]-amide;
(S)-2-Hydroxy-4-methyl-pentanoic acid [4,4-bis-(4-fluoro-phenyl)-butyl]-amide;
(S)-3-Methyl-2-methylamino-butanoic acid [4,4-bis-(4-fluorophenyl)-butyl]-amide;
N-[4,4-Bis-(4-fluoro-phenyl)-butyl]-2-methylamino-acetamide;
(S)-4-Ethyl-2-methylamino-pentanoic acid [4,4-bis-(4-fluorophenyl)butyl]-amide;
(S)-$N^1$-[4,4-Bis-(4-fluoro-phenyl)-butyl]-4-$N^2$-dimethyl-pentane-1,2-diamine;
(R)-$N^1$-[4,4-Bis-(4-fluoro-phenyl)-butyl]-4-$N^2$-dimethyl-pentane-1,2-diamine;
N-[4,4-Bis-(4-fluoro-phenyl)-butyl]-2-(isobutyl-methyl-amino)-acetamide;
(R)-N-[4,4-Bis-(4-fluoro-phenyl)-butyl]-2-methylamino-propionamide;
(S){1-[4,4-Bis-(4-fluoro-phenyl)-butylcarbamoyl]-2-methyl-propyl)-methyl-carbamic acid tert-butyl ester;
(S)N-[4,4-Bis-(4-fluoro-phenyl)-butyl]-3-methyl-2-methylamino-butyramide;
(S){1-[4,4-Bis-(4-fluoro-phenyl)-butylcarbamoyl]-2-methyl-butyl}-methyl-carbamic acid tert-butyl ester;
(S)3-Methyl-2-methylamino-pentanoic acid [4,4-bis-(4-fluoro-phenyl)-butyl]-amide;
(S){1-[4,4-Bis-(4-fluoro-phenyl)-butylcarbamoyl]-ethyl}-methyl-carbamic acid tert-butyl ester;
(S)N-[4,4-Bis-(4-fluoro-phenyl)-butyl]-2-methylamino-propionamide;
(S){1-[4,4-Bis-(4-fluoro-phenyl)-butylcarbamoyl]-2-cyclohexyl-ethyl}-methyl-carbamic acid tert-butyl ester;
(S)N-[4,4-Bis-(4-fluoro-phenyl)-butyl]-3-cyclohexyl-2-methylamino-propionamide;
(S){1-[4,4-Bis-(4-fluoro-phenyl)-butylcarbamoyl]-2-cyclohexyl-ethyl}-carbamic acid tert-butyl ester;
(S)2-Amino-N-[4,4-bis-(4-fluoro-phenyl)-butyl]-3-cyclohexyl-propionamide;
{1-[4,4-Bis-(4-fluoro-phenyl)-butylcarbamoyl]-cyclohexyl}-carbamic acid tert-butyl ester;
1-Amino-cyclohexanecarboxylic acid [4,4-bis-(4-fluoro-phenyl)-butyl]-amide;
{1-[4,4-Bis-(4-fluoro-phenyl)-butylcarbamoyl]-cyclohexyl}-methyl-carbamic acid tert-butyl ester;
1-Methylamino-cyclohexanecarboxylic acid [4,4-bis-(4-fluoro-phenyl)-butyl]-amide;
{1-[4,4-Bis-(4-fluoro-phenyl)-butylcarbamoyl]-cyclopentyl}-carbamic acid benzyl ester; and
1-Amino-cyclopentanecarboxylic acid [4,4-bis-(4-fluoro-phenyl)-butyl]-amide.

Also provided is a method of blocking calcium channels in a cell, the method comprising contacting the cell with the compound according to Formula I.

In a preferred embodiment, the calcium channels are N-type calcium channels.

Also provided is a method of treating or preventing an N-type calcium channel mediated affliction in a mammal in need thereof, the method comprising administering to the mammal a therapeutically effective amount of a compound of Formula I.

In a preferred embodiment, the affliction is stroke.

In a preferred embodiment, the affliction is cerebral ischemia.

In a preferred embodiment, the affliction is head trauma.

In a preferred embodiment, wherein the affliction is epilepsy.

In a preferred embodiment, wherein the affliction is pain.

Also provided is a pharmaceutical composition comprising a compound of Formula I.

DETAILED DESCRIPTION OF THE INVENTION

The following terms are employed herein as defined below, except as may be expressly modified.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

Preferred alkyls are $C_1$–$C_6$ alkyls.

The term "alkoxy" means an alkyl group attached to an oxygen atom. Representative examples of alkoxy groups include methoxy, ethoxy, tert-butoxy, propoxy, and isobutoxy.

The terms "halo" and "halogen" include chlorine, fluorine, bromine, and iodine.

The term "alkenyl" means a branched or straight chain hydrocarbon having one or more carbon-carbon double bond.

The term "heteroatom" means oxygen, nitrogen, sulfur, or phosphorus.

The term "cycloalkyl" means a cyclic hydrocarbon. Examples of cycloalkyl groups include cyclopropyl, cyclobutyl, cyclopentyl, and cyclohexyl.

The term "heterocycle" or "heterocycloalkyl" means a 3- to 7-membered cycloalkyl moiety wherein one or more of the ring carbons is substituted by a heteroatom. Examples of heterocycles include, but are not limited to, pyrrolidinyl, piperidinyl, piperazinyl, and morpholinyl.

The term "aryl" means an aromatic hydrocarbon. Representative examples of aryl groups include phenyl and naphthyl.

The term "heteroaryl" means an aryl group wherein one or more carbon atom of the aromatic hydrocarbon has been replaced with a heteroatom. Examples of heteroaryl radicals include, but are not limited to, pyridyl, imidazolyl, pyrrolyl, thienyl, furyl, pyranyl, pyrimidinyl, pyridazinyl, indolyl, quinolyl, naphthyridinyl, and isoxazolyl.

The term "substituted" means that the base organic radical has one or more substituents. For example, substituted cyclohexyl means a cyclohexyl radical that has one or more substituents. Substituents include, but are not limited to, halogen, $C_1$–$C_8$ alkyl, —CN, $CF_3$, —$NO_2$, —$NH_2$, —$NHC_1$–$C_8$ alkyl, —$N(C_1$–$C_8$ alkyl)$_2$, —$OC_1$–$C_8$ alkyl, and —OH. Particularly preferred substituents include, but are not limited to, tert-butyl, methyl, chlorine, fluorine, bromine, —$OCH_3$, —$OCH_2CH_3$, —OH, and —$N(CH_3)_2$.

The symbol "—" means a bond.

The term "patient" means all animals including humans. Examples of patients include humans, cows, dogs, cats, goats, sheep, and pigs.

The following abbreviations are used throughout the application:

| | |
|---|---|
| APCI | Atmospheric pressure chemical ionization |
| BOC or Boc | tertiary-Butyloxy carbonyl |
| BSA | Bovine Serum Albumin |
| DMF | Dimethylformamide or dimethyl formamide |
| EDTA | Ethylenediaminetetraacetic acid |
| EGTA | (Ethylene glycol-bis [β-aminoethylether]-N,N,N'N'-tetracetic acid) |
| Et | Ethyl |
| EtOAC | Ethyl acetate |
| EtOH | Ethanol |
| FLIPR | Fluorescent Imaging Plate Reader |
| HCl | Hydrochloric acid |
| HEPES | (N-[2-Hydroxyethyl]piperazine-N'-[2-ethansulfonic acid]) |
| HOBt | 1-Hydroxybenzotriazole |
| IPr2NEt | Diisopropylethylamine |
| IR | Infrared |
| MS | Mass spectrum |
| msec | Millisecond |
| mV | Millivolt |
| SCG | Superior cervical ganglion |
| THF | Tetrahydrofuran |
| TLC | Thin layer chromatograph or thin layer chromatography |
| RT | Room temperature |

The compounds of the invention may be readily prepared as set forth in the following reaction scheme:

I. Amino acid synthesis was carried out by stepwise condensation of an aldehyde or ketone with a naturally occurring amino acid, followed by reduction. This sequence was repeated in order to prepare N,N-dialkyl amino acids, as illustrated below.

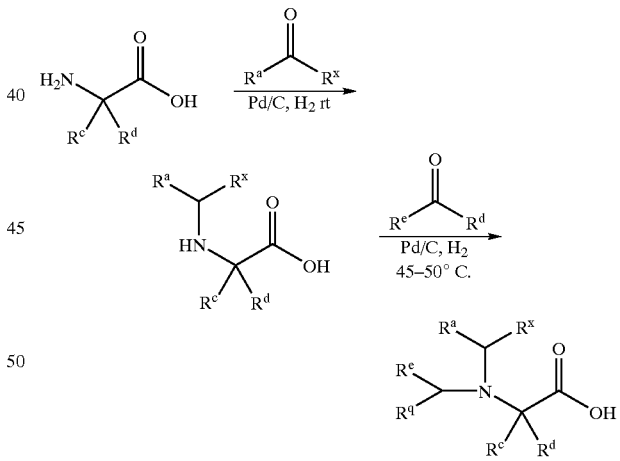

II. Coupling procedures

1. For N,N-dialkyl substituted amino acids

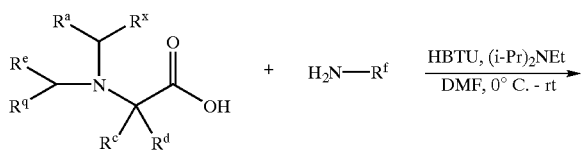

-continued

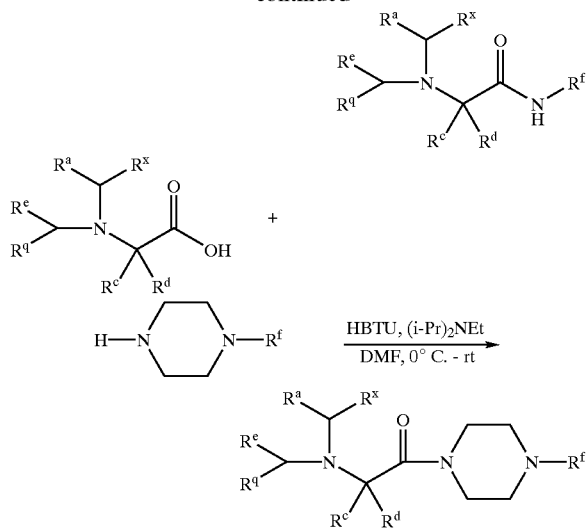

2. When the acids are secondary amino acids

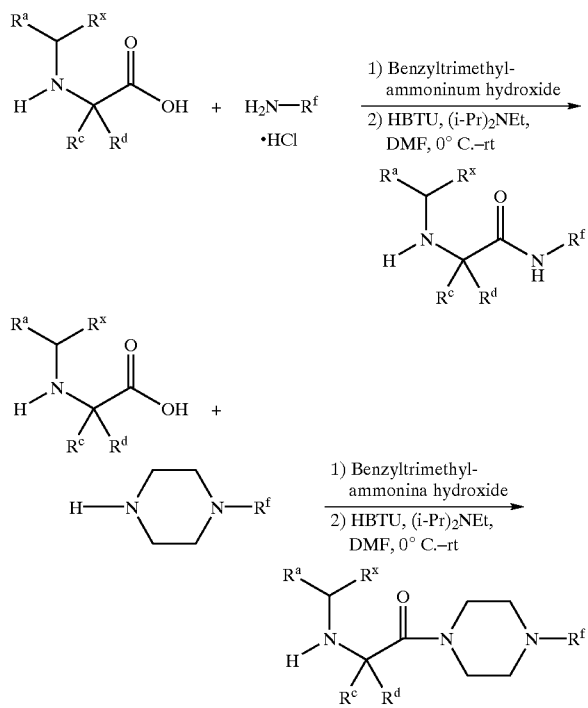

3. For N-acyl amino acids a.

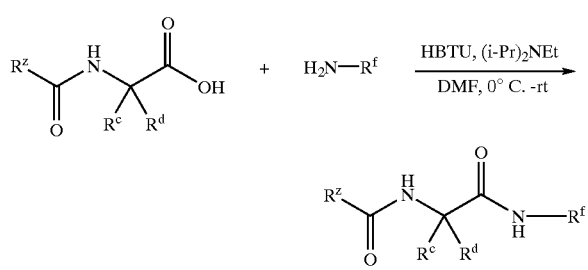

b.

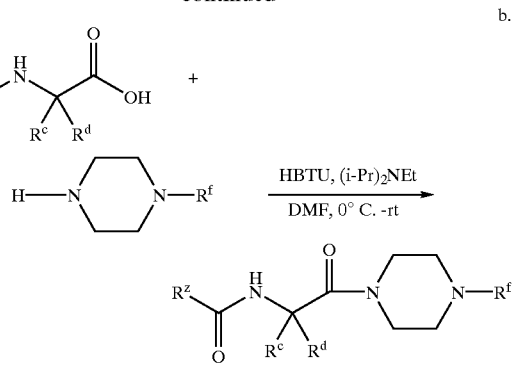

Each of the above variables $R^a$, $R^c$, $R^d$, $R^e$, $R^f$, $R^x$, $R^q$, and $R^z$ are defined as is consistent with the compounds disclosed herein.

Those skilled in the art are easily able to identify patients having a stroke or at risk of having a stroke, cerebral ischemia, head trauma, or epilepsy. For example, patients who are at risk of having a stroke include, but is not limited to, patients having hypertension or undergoing major surgery.

A therapeutically effective amount is an amount of a compound of Formula I that when administered to a patient, ameliorates a symptom of the disease.

The compounds of the present invention can be administered to a patient either alone or a part of a pharmaceutical composition. The compositions can be administered to patients either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Also included in the invention are pharmaceutically acceptable salts, esters, amides, and prodrugs of the compounds of the invention. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laureate, borate, benzoate, lactate, phosphate, tosylate, citrate, maleate, lumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary anmonium and amine cations including, but not limited to ammonium, tetramethylammonium, tetraethylammonium, methylamine, dimethylamine, trimethylamine, triethylamine, ethylamine, and the like. (See, for example, S. M. Berge et al., "Pharmaceutical Salts," *J. Pharm. Sci.*, 1977;66:1–19 which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amines, and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formula, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisomeric forms by virtue of the presence of asymmetric centers in the compounds. It is contemplated that all stereoisomeric forms of the compounds, as well as mixtures thereof including racemic mixtures, form part of this invention.

The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depend on a numbers of factors including the requirements of the patient, the severity of the condition being treated, and the pharmacological activity of the compound being used. The determination of optimum dosages for a particular patient is well-known to those skilled in the art.

The compounds of the invention are also useful research tools for studying the biological, cellular effects of blocking N-type calcium channels.

In addition, it is intended that the present invention cover compounds made either using standard organic synthetic techniques, including combinatorial chemistry or by biological methods, such as through metabolism.

The examples presented below are intended to illustrate particular embodiments of the invention and are not intended to limit the scope of the specification, including the claims, in any way.

EXAMPLE 1

Preparation of (S)-Azepane-1-carboxylic acid {1-[4,4-bis-(4-fluoro-phenyl)-butylcarbamoyl]-3-methyl-butyl}-amide

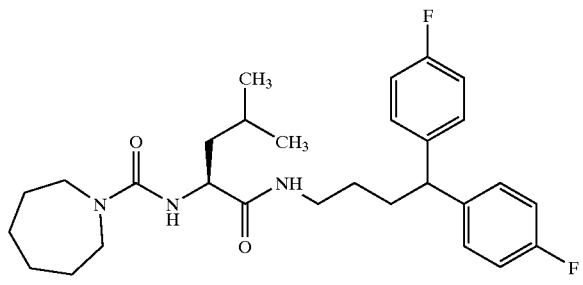

Step A. (S)-2-[(Azepane-1-carbonyl)-amino]-4-methyl-pentanoic acid benzyl ester

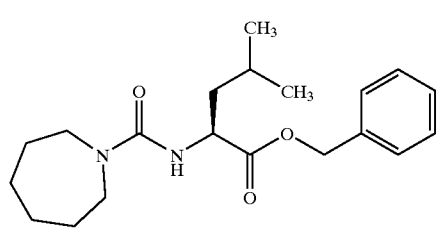

A solution of triphosgene (15.7 g, 52.9 mmol) in CH$_2$Cl$_2$ (600 mL) was cooled to −10° C. under a nitrogen atmosphere. The solution was treated dropwise with a solution of (S)-2-amino-4-methyl-pentanoic acid benzyl ester (28.1 g, 0.127 mol) and pyridine (26 mL, 0.32 mol) in 150 mL of CH$_2$Cl$_2$. The resulting solution was stirred at −10° C. for 90 minutes and then treated with a solution of hexamethyleneimine (22 mL, 0.38 mmol) in 75 mL of CH$_2$Cl$_2$. The resulting solution was stirred for 48 hours at room temperature. The reaction mixture was concentrated, and the residue was dissolved in ether and washed with 1N HCl solution, water, and saturated aqueous CuSO$_4$ solution. The organic layer was dried (MgSO$_4$), treated with activated charcoal and filtered. The filtrate was concentrated to approximately one-half volume and treated with hexane. The resulting suspension was stored overnight at −10° C. The solid was collected by filtration, washed with hexane and dried under vacuum to give the title compound as a white solid (38.6 g, 88%); mp 87–88° C. APCI-MS m/z 347 (MH+).

Step B. (S)-2-[(Azepane-1-carbonyl)-amino]-4-methyl-pentanoic acid

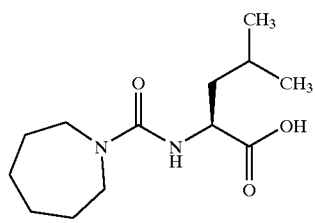

A solution of (S)-2-[(azepane-1-carbonyl)-amino]-4-methyl-pentanoic acid benzyl ester (38.5 g. 111 mmol) in 600 mL of THF was hydrogenated at 50 psi over 20% Pd/C (2.00 g) for 17 minutes. The reaction mixture was filtered through celite and concentrated to dryness. The residue was heated in 50 mL of hexane. The resulting suspension was cooled and the solid collected by filtration and washed with hexane. The solid was dried at room temperature under vacuum to give the title compound as a white solid (26.6 g, 93%); mp 88–89° C.

Anal. Cl$_3$H$_{24}$N$_2$O$_3$: C, 60.91; H, 9.44; N, 10.93. Found: C, 60.99; H, 9.46; N, 10.85.

Step C. 1,1'-(4-bromobutylidene)bis[4-fluorobenzene]

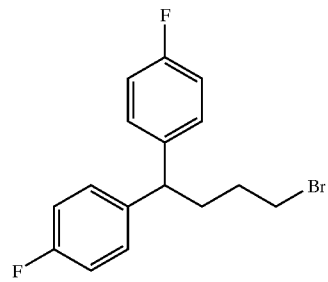

The synthesis was reported by Rajsner et. al., in *Collect. Czech. Chem. Comm.*, 1978;43:1760–1777.

Step D. 2-[4,4-Bis-(4-fluoro-phenyl)-butyl]-isoindole-1,3-dione

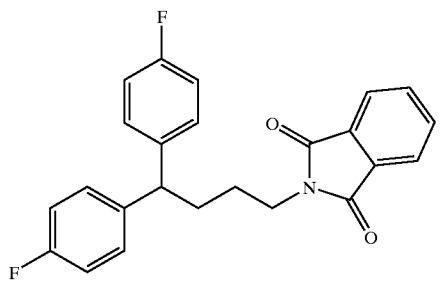

A suspension consisting of 1,1'-(4-bromobutylidene)bis[4-fluorobenzene] (25 g, 77 mmol) and potassium phthalimide (17 g, 92 mmol) in 300 mL DMF was stirred at 50° C. for 16 hours, cooled to 25° C., and poured into 900 mL of cold $H_2O$. The mixture was extracted with ethyl acetate (3×300 mL), and the combined extracts were washed with $H_2O$ (2×1 L), followed by brine (700 mL), then dried over anhydrous sodium sulfate. Evaporation of solvent in vacuo afforded 28.6 g of a golden oil, which was triturated with 250 mL 2,2,4-trimethylpentane containing 5% 2-propanol, and the solid thus obtained was collected by filtration and dried at 50° C. in vacuo, to give 28.7 g (97%) of titled compound as a white powder; mp 69–70° C. APCI-MS m/z 391.1 (M⁻).

Step E

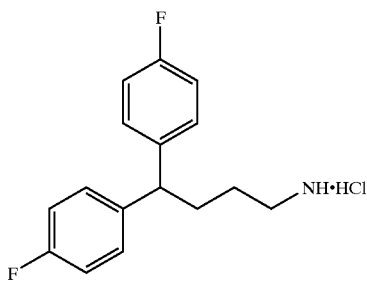

A mixture of 2-[4,4-Bis-(4-fluoro-phenyl)-butyl]-isoindole-1,3-dione (25.44 g, 65 mmol), sodium borohydride (12.29 g, 325 mmol), $H_2O$ (25 mL), and 2-propanol (55 mL) was stirred at 25° C. for 4 hours, then 275 mL of methanol that had been saturated with hydrogen chloride gas was very carefully added, and the mixture heated under reflux for 1 hour, then cooled to 25° C. The precipitate that formed was removed by filtration and the filtrate concentrated to dryness. Triturate the residue in 250 mL ethyl acetate, filter, and wash solids with two 50 mL portions of ethyl acetate to give 11.57 g (61%) of the titled compound as a white solid; mp 211–212° C. APCI-MS m/z 262.2 (MH⁺).

Step F (S)-2-[(Azepane-1-carbonyl)-amino]-4-methyl-pentanoic (0.37 g, 1.4 mmol) was dissolved in dry DMF (5 mL) under nitrogen atmosphere and cooled to 0° C. in an ice-water bath. To this solution were added, in succession, N,N-diisopropylethylamine (0.76 mL, 4.4 mmol) and solid O-benzotriazol-1-yl-N,N,N',N'-tetramethyluronium hexafluorophosphate (0.55 g, 1.5 mmol, Novabiochem, La Jolla, Calif.). The resulting reaction mixture was stirred at that temperature for 30 minutes; 4,4-bis-(4-fluoro-phenyl)-butylamine monohydrochloride (0.43 g, 1.4 mmol) was then added. After additional 30 minutes stirring at 0° C., reaction mixture was mixed with 60 mL of diethyl ether; the resulting mixture was successively washed with 5% aqueous HCl solution, brine, saturated aqueous $NaHCO_3$ solution, brine, and was dried over $Na_2SO_4$. The solution was concentrated in vacuo, a white solid was obtained. Recrystallization from EtOAc afforded 0.60 g (83%) of the pure titled compound as a white solid; mp 163–164° C.; APCI-MS m/z 500.6 (MH⁺);

EXAMPLE 2

Preparation of (R)-Azepane-1-carboxylic acid {1-[4,4-bis-(4-fluoro-phenyl)-butylcarbamoyl]-3-methyl-butyl}-amide

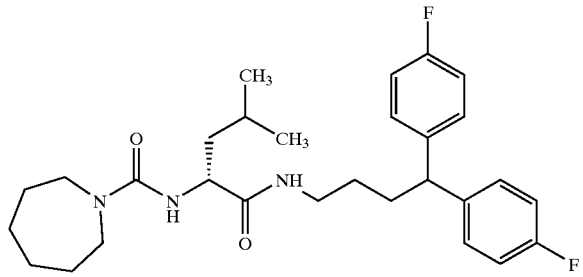

Step A. (R)-2-[(Azepane-1-carbonyl)-amino]-4-methyl-pentanoic acid benzyl ester

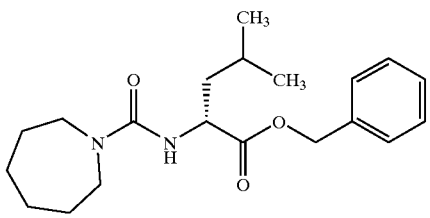

A solution of (R)-2-amino-4-methyl-pentanoic acid benzyl ester (14.1 g, 63.6 mmol) and pyridine (25 mL, 0.31 mmol) in 400 mL of $CH_2Cl_2$ was cooled to 0° C. and treated rapidly with phosgene (40 mL of a 1.9 M solution in toluene) in one portion. The resulting solution was stirred at 0° C. for 2 hours and then treated with hexamethyleneimine (9.3 mL, 82.7 mmol) in $CHCl_3$ (25 mL). The resulting solution was warmed to room temperature and concentrated. The residue was dissolved in ether and washed with aqueous 1N HCl solution. The organic phase was dried ($MgSO_4$), filtered and concentrated. The crude residue was purified by chromatography (silica gel, 2:1 heptane/ethyl acetate) to give the title compound as a yellow solid (4.96 g, 68%); mp 88–89° C. APCI-MS m/z 347 (MH⁺).

Step B. (R)-2-[(Azepane-1-carbonyl)-amino]-4-methyl-pentanoic acid

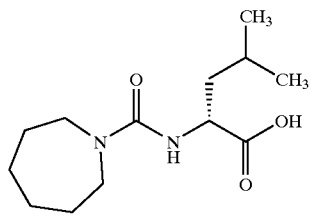

In a manner similar to that described in Example 1, Step B, (R)-2-[(Azepane-1-carbonyl)amino]-4-methyl-pentanoic acid benzyl ester (9.03 g, 26.1 mmol) was converted to the title compound (6.25 g, 93%); mp 87–88° C.

Anal. $C_{13}H_{24}N_2O_3$: C, 60.91; H, 9.44; N, 10.93. Found: C, 60.85; H, 9.33; N, 10.92.

Step C (R)-2-[(Azepane-1-carbonyl)-amino]-4-methyl-pentanoic (0.300 g, 1.17 mmol) was dissolved in dry DMF (4 mL) under nitrogen atmosphere and cooled to 0° C. in an ice-water bath. To this solution were added, in succession N,N-diisopropylethylamine (0.612 mL, 3.51 mmol) and solid O-benzotriazol-1-yl-N,N,N',N'-tetramethyluronium hexafluorophosphate (0.444 g, 1.17 mmol). The resulting reaction mixture was stirred at that temperature for 40 minutes, 4,4-bis-(4-fluoro-phenyl)-butylamine monohydrochloride (0.306 g, 1.17 mmol) was then added. After stirring for, sequentially, 25 minutes at 0° C. and 50 minutes at ambient temperature, reaction mixture was mixed with 60 mL of diethyl ether; the resulting mixture was successively washed with saturated aqueous $NaHCO_3$ solution (2×60 mL), brine (2×60 mL), and was dried over $Na_2SO_4$. The solution was concentrated in vacuo affording a solid. Recrystallization from EtOAc afforded 0.060 g (10%) of the pure titled compound as a white solid: mp 161–163° C. APCI-MS m/z 500.4 (MH$^+$).

EXAMPLE 3

Preparation of (S)-Azepane-1-carboxylic acid [1-(benzhydryl-carbamoyl)-3-methyl-butyl]-amide

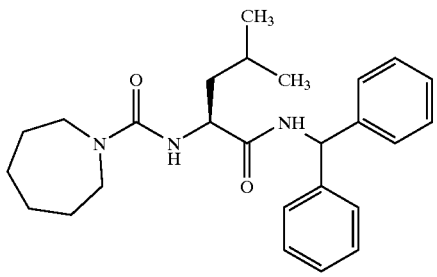

(S)-2-[(Azepane-1-carbonyl)-amino]-4-methyl-pentanoic acid (0.51 g, 2.0 mmol, Example 1, Step B) was dissolved in dry DMF (6 mL) under nitrogen atmosphere and cooled to 0° C. in an ice-water bath. To this solution were added, in succession, N,N-diisopropylethylamine (1.0 mL, 5.7 mmol) and solid O-benzotriazol-1-yl-N,N,N',N'-tetramethyluronium hexafluorophosphate (0.74 g, 2.0 mmol). The resulting reaction mixture was stirred at that temperature for 30 minutes; aminodiphenylmethane hydrochloride (0.43 g, 2.0 mmol, Aldrich, Milwaukee, Wis.) was then added. After additional 30 minutes stirring at 0° C., reaction mixture was mixed with 60 mL of diethyl ether; the resulting mixture was successively washed with 5% aqueous HCl solution, brine, saturated aqueous $NaHCO_3$ solution, brine, and was dried over $Na_2SO_4$. The solution was concentrated in vacuo, a white solid was obtained. Recrystallization from EtOAc-hexanes afforded 0.67 g (82%) of the pure titled compound as a white solid: mp 180–181° C. APCI-MS m/z 422.3 (MH$^+$).

EXAMPLE 4

Preparation of (S)-Azepane-1-carboxylic acid [1-(2,2-diphenyl-ethylcarbamoyl)-3-methyl-butyl]-amide

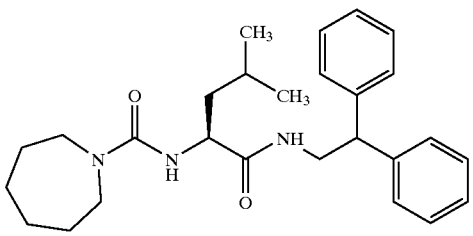

(S)-2-[(Azepane-1-carbonyl)-amino]-4-methyl-pentanoic acid (0.51 g, 2.0 mmol, Example 1, Step B) was dissolved in dry DMF (5 mL) under nitrogen atmosphere and cooled to 0° C. in an ice-water bath. To this solution were added, in succession, N,N-diisopropylethylamine (0.68 mL, 3.9 mmol) and solid O-benzotriazol-1-yl-N,N,N',N'-tetramethyluronium hexafluorophosphate (0.74 g, 2.0 mmol). The resulting reaction mixture was stirred at that temperature for 30 minutes; 2,2-diphenylethylamine (0.38 g, 1.9 mmol, Aldrich, Milwaukee, Wis.) was then added. After additional 30 minutes stirring at 0° C., reaction mixture was mixed with 60 mL of diethyl ether; the resulting mixture was successively washed with 5% aqueous HCl solution, brine, saturated aqueous $NaHCO_3$ solution, brine, and was dried over $Na_2SO_4$. The solution was concentrated in vacuo, a white solid was obtained. Recrystallization from EtOAc-hexanes afforded 0.71 g (84%) of the pure titled compound as a white solid; mp 194–195° C. APCI-MS m/z 436.3 (MH$^+$).

EXAMPLE 5

Preparation of (S)-Azepane-1-carboxylic acid [1-(3,3-diphenyl-propylcarbamoyl)-3-methyl-butyl]-amide

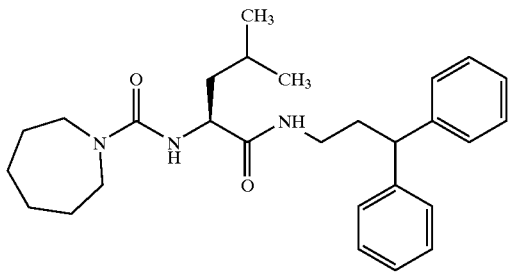

(S)-2-[(Azepane-1-carbonyl)-amino]-4-methyl-pentanoic acid (0.51 g, 2.0 mmol, Example 1, Step B) was dissolved in dry DMF (5 mL) under nitrogen atmosphere and cooled to 0° C. in an ice-water bath. To this solution were added, in succession, N,N-diisopropylethylamine (0.68 mL, 3.9 mmol) and solid O-benzotriazol-1-yl-N,N,N',N'-tetramethyluronium hexafluorophosphate (0.74 g, 2.0 mmol). The resulting reaction mixture was stirred at that temperature for 30 minutes; 3,3-diphenylpropylamine (0.41 g, 1.9 mmol, Aldrich, Milwaukee, Wis.) was then added. After additional 30 minutes stirring at 0° C., reaction mixture was mixed with 60 mL of diethyl ether; the resulting mixture was successively washed with 5% aqueous HCl solution, brine, saturated aqueous $NaHCO_3$ solution, brine, and was dried over $Na_2SO_4$. The solution was concentrated in vacuo, a white solid was obtained. Recrystallization from EtOAc-hexanes afforded 0.63 g (72%) of the pure titled compound as a white solid; mp 144–145° C. APCI-MS m/z 450.3 ($MH^+$).

EXAMPLE 6

Preparation of (S)-{1-[4,4-Bis-(4-fluoro-phenyl)-butylcarbamoyl]-3-methyl-butyl}-carbamic acid tert-butyl ester

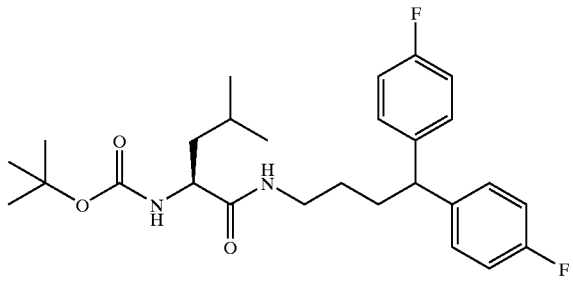

N-tert-butoxycarbonyl-L-leucine (0.84 g, 3.4 mmol, Bachem Inc., Torrance, Calif.) was dissolved in dry DMF (7 mL) under nitrogen atmosphere and cooled to 0° C. in an ice-water bath. To this solution were added, in succession, N,N-diisopropylethylamine (1.8 mL, 10 mmol) and solid O-benzotriazol-1-yl-N,N,N',N'-tetramethyluronium hexafluorophosphate (1.3 g, 3.4 mmol). The resulting reaction mixture was stirred at that temperature for 30 minutes; benzenebutanamine, 4,4-bis-(4-fluoro-phenyl)-butylamine monohydrochloride (1.0 g, 3.4 mmol) was then added. After additional 30 minutes stirring at 0° C., reaction mixture was mixed with 60 mL of diethyl ether; the resulting mixture was successively washed with 2% aqueous HCl solution, brine, saturated aqueous $NaHCO_3$ solution, brine, and was dried over $Na_2SO_4$. Concentration in vacuo followed by drying under vacuum afforded 1.4 g (90%) of the pure titled compound was obtained as a white foam: mp 50–55° C. APCI-MS m/z 475.3 ($MH^+$).

EXAMPLE 7

Preparation of (S)-2-Amino-4-methyl-pentanoic acid [4,4-bis-(4-fluoro-phenyl)-butyl]-amide monohydrochloride

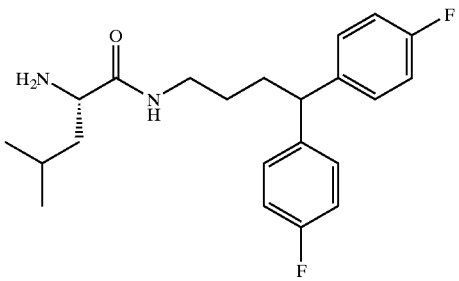

To a solution of (S)-{1-[4,4-bis-(4-fluoro-phenyl)-butylcarbamoyl]-3-methyl-butyl}-carbamic acid tert-butyl ester (1.4 g, 3.8 mmol, Example 6) in $CH_2Cl_2$ (15 mL) was added trifluoroacetic acid (5 mL) at ambient temperature under nitrogen atmosphere. The resulting reaction mixture was stirred for 25 minutes, then concentrated in vacuo. The viscous oil obtained was dissolved in 60 mL of $CH_2Cl_2$ and successively washed with saturated aqueous $NaHCO_3$ solution (2×60 mL), brine (2×60 mL), and was dried over $Na_2SO_4$. The $CH_2Cl_2$ solution of free amine was concentrated in vacuo to afford the crude product as a viscous oil which was then dissolved in 10 mL of ethyl ether. To this solution was added saturated HCl solution in ethyl ether until no more white precipitate formed. Filtration and drying overnight under vacuum afforded 1.2 g (99.6%) of crude product. A portion of the crude product, a HCl salt, was converted back to the free amine by treatment with saturated aqueous $NaHCO_3$ solution; the crude free amine was further purified by flash chromatography (straight EtOAc, then 10% MeOH in $HCCl_3$) and converted into HCl salt as described above. Pure titled compound was obtained as a white foam (0.3 g); mp 65–80° C. APCI-MS m/z 375.3 ($MH^+$).

EXAMPLE 8

Preparation of (S)-2-(Cyclohexylmethyl-amino)-4-methyl-pentanoic acid [4,4-bis-(4-fluoro-phenyl)-butyl]-amide monohydrochloride

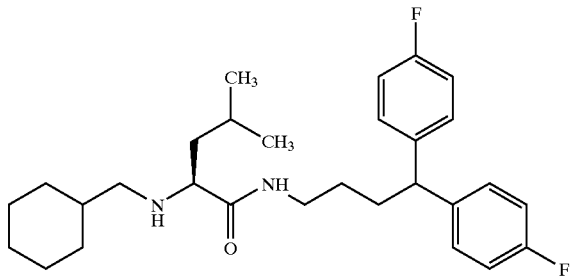

(S)-2-Amino-4-methyl-pentanoic acid [4,4-bis-(4-fluoro-phenyl)-butyl]-amide monohydrochloride (0.29 g, 0.71 mmol, Example 7) and cyclohexanecarboxaldehyde (0.086 mL, 0.71 mmol, Aldrich, Milwaukee, Wis.) were mixed in CH$_2$Cl$_2$ (10 mL). After stirring at ambient temperature under nitrogen atmosphere for 30 minutes, the solution was cooled to 0° C. in an ice-water bath. To this solution was added sodium triacetoxyborohydride (0.22 g, 1.0 mmol). The resulting reaction mixture was stirred for, in succession, 30 minutes at 0° C. and 12 hours at ambient temperature. Ten milliliters of saturated aqueous NaHCO$_3$ solution was added to the reaction mixture, and the resulting mixture was stirred for 5 minutes. The 2 layers were separated, and the aqueous layer was extracted with CH$_2$Cl$_2$ (2×10 mL). The combined organic solution was dried over Na$_2$SO$_4$. The solution was concentrated in vacuo affording a viscous oil. Desired free amine was isolated after flash chromatography (40% EtOAc in hexanes). The free amine was dissolved in 5 mL of ethyl ether and treated with ethereal HCl to afford 0.30 g (84%) of the pure titled compound as a white foam: mp 84–110° C. APCI-MS m/z 471.3 (MH$^+$).

EXAMPLE 9

Preparation of (S)-4-Methyl-2-(3-methyl-but-2-enylamino)-pentanoic acid [4,4-bis-(4-fluoro-phenyl)-butyl]-amide monohydrochloride

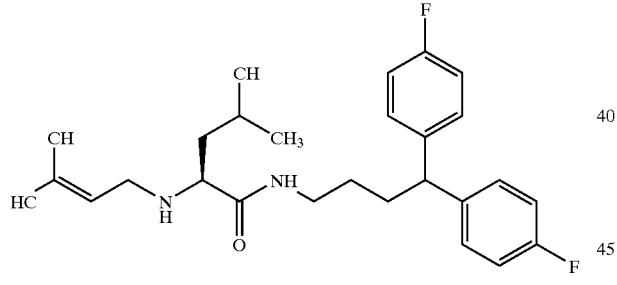

To a solution of (S)-2-amino-4-methyl-pentanoic acid [4,4-bis-(4-fluoro-phenyl)-butyl]-amide monohydrochloride (0.36 g, 0.88 mmol, Example 7) in THF (15 mL) were added, in succession, N,N-diisopropylethylamine (0.30 mL, 1.7 mmol) and 1-bromo-3-methyl-2-butene (0.10 mL, 0.87 mmol) at ambient temperature under nitrogen atmosphere. The resulting reaction mixture was stirred for 12 hours at that temperature, 16 hours at 50° C., cooled to ambient temperature, and concentrated in vacuo. The desired product was purified by flash chromatography (50% EtOAc in hexanes) and was dissolved in 10 mL of ethyl ether. To this solution was added saturated HCl solution in ethyl ether until no more white precipitate formed. Filtration and drying overnight under vacuum afforded 0.14 g (36%) of the titled compound as a yellow foam; mp 58–72° C. APCI-MS m/z 443.3 (MH$^+$).

EXAMPLE 10

Preparation of (S)-Azepane-1-carboxylic acid {3-methyl-1-[3-(1-methyl-2-oxo-3-phenyl-2,3-dihydro-1H-indol-3-yl)-propylcarbamoyl]-butyl}-amide

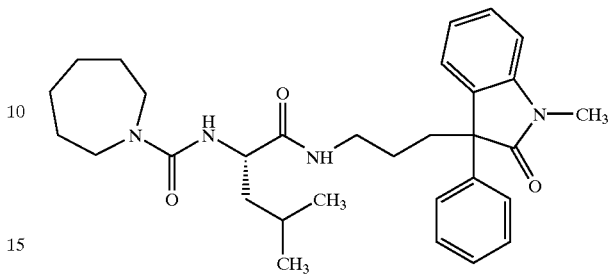

Step A. 3-(1-Methyl-2-oxo-3-phenyl-2,3-dihydro-1H-indol-3-yl)-propionitrile

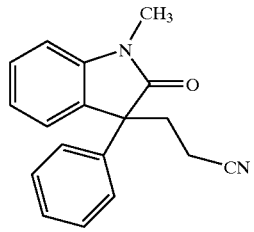

Synthesis is reported in *J Org. Chem.*, 1965;30:2973–2983.

Step B. 3-(3-Amino-propyl)-1-methyl-3-phenyl-1,3-dihydro-indol-2-one monohydrochloride monohydrate

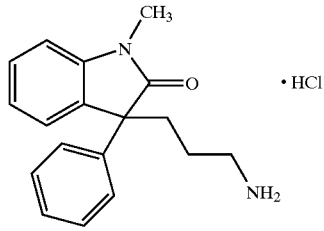

To a solution of 3-(1-methyl-2-oxo-3-phenyl-2,3-dihydro-1H-indol-3-yl)-propionitrile (64.0 g, 0.232 mmol) in toluene (400 mL) were added catalyst Ra—Co (15 g) and triethylamine (15 mL). The reaction mixture was sealed in an autoclave and agitated under hydrogen atmosphere at 2000 PSI at 110° C. for 90 minutes. The reaction mixture was cooled to ambient temperature and filtered. The filtrate was concentrated in vacuo to dryness, 48.6 g of light yellow solid was obtained. Five grams were taken up in EtOAc; the solution was saturated with HCl gas, a white precipitate forms which was collected via filtration and dried. The desired product was isolated as a white solid; mp 172–174° C.

Anal. C$_{18}$H$_{20}$N$_2$O.HCl.H$_2$O: C, 66.91; H, 6.77. Found: C, 66.69; H, 6.86.

Step C (S)-2-[(Azepane-1-carbonyl)-amino]-4-methyl-pentanoic acid (0.39 g, 1.5 mmol, Example 1, Step B) was dissolved in dry DMF (5 mL) under nitrogen atmosphere and cooled to 0° C. in an ice-water bath. To this solution were added, in succession, N-methylmorpholine (0.66 mL, 6.0 mmol) and solid O-benzotriazol-1-yl-N,N,N',N'-tetramethyluronium hexafluorophosphate (0.60 g, 1.6 mmol). The resulting reaction mixture was stirred at that temperature for 30 minutes; then a solution of 3-(3-amino-propyl)-1-methyl-3-phenyl-1,3-dihydro-indol-2-one monohydrochloride monohydrate (0.49 g, 1.5 mmol) in dry DMF (7 mL) was added. After additional 20 minutes stirring at 0° C., the ice-water bath was removed and the reaction mixture was stirred and allowed to warm up to ambient temperature for 15 minutes. The reaction mixture was poured into 50 mL of EtOAc, the resulting mixture was successively washed with 3% aqueous HCl solution, brine, saturated aqueous NaHCO$_3$ solution, brine, and was dried over Na$_2$SO$_4$. The solution was concentrated in vacuo affording a white solid. Recrystallization from EtOAc-hexanes afforded 0.56 g (72%) of the pure titled compound as a white powder: mp 181–182° C. APCI-MS m/z 519.1 (MH$^+$).

EXAMPLE 11

Preparation of (S)-Azepane-1-carboxylic acid {3-methyl-1-[(1-phenyl-1H-indazol-3-ylmethyl)-carbamoyl]-butyl}-amide

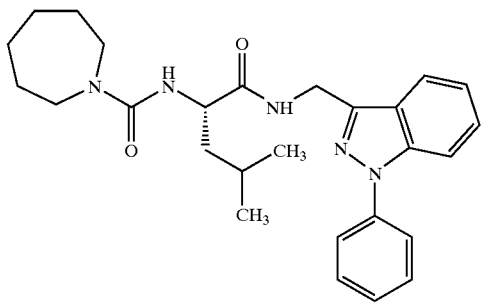

Step A. 1-Phenyl-1H-indazole-3-carboxylic acid

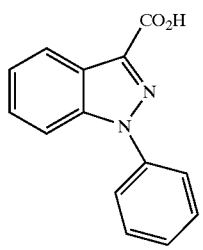

Made according to procedures described in *Aust. J. Chem.*, 1973;26:2683–2695.

Step B. 1-Phenyl-1H-indazole-3-carboxylic acid amide

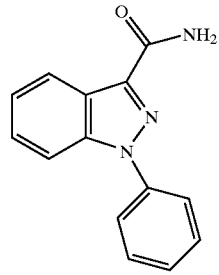

To a solution of 1,1'-carbonyldiimidazole (3.4 g, 21 mmol) in 60 mL of dry THF was added dropwise a solution of 1-phenyl-1H-indazole-3-carboxylic acid (5.0 g, 21 mmol) in 60 mL dry THF under nitrogen atmosphere. The resulting reaction mixture was stirred at ambient temperature for 30 minutes and refluxed for 30 minutes; then cooled to ambient temperature under nitrogen atmosphere. Ammonia, generated by warming concentrated aqueous ammonia solution, was bubbled through, and the reaction mixture was stirred overnight at ambient temperature. The reaction mixture was concentrated in vacuo to dryness, the solid was dissolved in 200 mL of ethyl acetate, the solution was successively washed with 1N aqueous HCl solution (2×50 mL), 1N aqueous NaOH solution (5×20 mL) and was dried over Na$_2$SO$_4$. Concentration and drying under vacuum gave 4.65 g (93%) of desired product as a white solid: mp 149° C.

Anal. C$_{14}$H$_{11}$N$_3$O$_1$: C, 70.87; H, 4.67; N, 17.71. Found: C, 70.53; H, 4.65; N, 17.48.

Step C. C-(1-Phenyl-1H-indazol-3-yl)-methylamine monohydrochloride

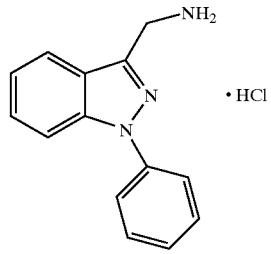

To a suspension of lithium aluminum hydride (0.76 g, 20 mmol) in 80 mL of dry THF cooled in an ice-water bath was added dropwise a solution of 1-phenyl-1H-indazole-3-carboxylic acid amide (2.4 g, 10 mmol) in 25 mL of dry THF under nitrogen atmosphere. Gas was evolved upon addition. The reaction mixture was stirred for 45 minutes in the ice-water bath, allowed to warm to ambient temperature, then refluxed for 2 hours. The reaction mixture was cooled to ambient temperature, and a mixture of Na$_2$SO$_4$ (10 g), Celite (8 g) and water (2 g) was added to the reaction mixture. The reaction mixture was filtered through celite and washed with THF; the filtrate was concentrated in vacuo affording an yellow oil which was purified by alumina chromatography (CH$_2$Cl$_2$, CH$_2$Cl$_2$/MeOH as eluant). The oil was partitioned between 1N HCl and CH$_2$Cl$_2$, and a solid forms which was isolated by filtration and dried under vacuum at 78° C.; mp 223–226° C.

Anal. C$_{14}$H$_{13}$N$_3$. C, 64.74; H, 5.43; N, 16.18. Found: C, 64.61; H, 5.34; N, 16.13

Step D (S)-2-[(Azepane-1-carbonyl)-amino]-4-methyl-pentanoic acid (0.45 g, 1.8 mmol, Example 1, Step B) was dissolved in dry DMF (6 mL) under nitrogen atmosphere and cooled to 0° C. in an ice-water bath. To this solution were added, in succession, N-methylmorpholine (0.68 mL, 6.1 mmol) and solid O-benzotriazol-1-yl-N,N,N',N'-tetramethyluronium hexafluorophosphate (0.70 g, 1.8 mmol). The resulting reaction mixture was stirred at that temperature for 30 minutes; then a solution of C-(1-phenyl-1H-indazol-3-yl)-methylamine monohydrochloride (0.45 g, 1.8 mmol) in dry DMF (8 mL) was added. After additional 20 minutes stirring at 0° C., the ice-water bath was removed, and the reaction mixture was stirred and allowed to warm up to ambient temperature for 15 minutes. The reaction mixture was poured into 50 mL of EtOAc; the resulting mixture was successively washed with 3% aqueous HCl solution, brine, saturated aqueous $NaHCO_3$ solution, brine, and was dried over $Na_2SO_4$. The solution was concentrated in vacuo affording an amber oil which was further purified by flash chromatography (80% EtOAC in hexanes). Finally, recrystallization from EtOAc-Hexanes afforded 0.39 g (48%) of the pure titled compound as a off-white solid: mp 135–136° C. APCI-MS m/z 462.0 ($MH^+$).

EXAMPLE 12

Preparation of (S)-4-Methyl-2-methylamino-pentanoic acid [4,4-bis-(4-fluoro-phenyl)-butyl]-amide monohydrochloride

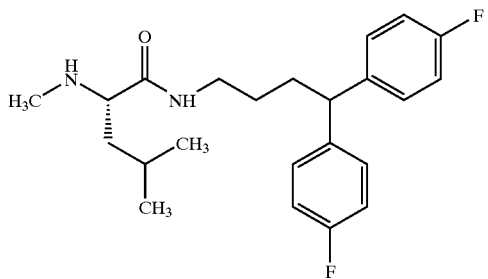

Step A. (S)-{1-[4,4-Bis-(4-fluoro-phenyl)-butylcarbamoyl]-3-methyl-butyl}-methyl-carbamic acid tert-butyl ester

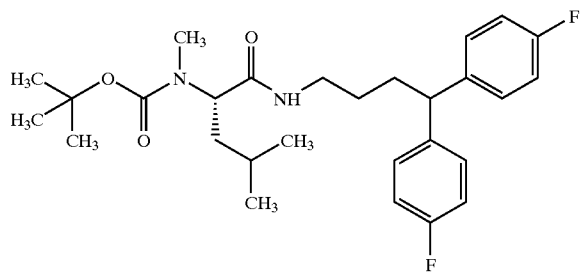

N-tert-Butoxycarbonyl-N-methyl-L-leucine (0.42 g, 1.7 mmol, Bachem Inc., Torrance, Calif.) was dissolved in dry DMF (5 mL) under nitrogen atmosphere and cooled to 0° C. in an ice-water bath. To this solution were added, in succession, N,N-diisopropylethylamine (0.90 mL, 5.2 mmol) and solid O-benzotriazol-1-yl-N,N,N',N'-tetramethyluronium hexafluorophosphate (0.66 g, 1.7 mmol). The resulting reaction mixture was stirred at that temperature for 30 minutes; 4,4-bis-(4-fluoro-phenyl)-butylamine monohydrochloride (0.51 g, 1.7 mmol) was then added. After additional 30 minutes stirring at 0° C., reaction mixture was mixed with 60 mL of diethyl ether; the resulting mixture was successively washed with 5% aqueous HCl solution, brine, saturated aqueous $NaHCO_3$ solution, brine, and was dried over $Na_2SO_4$. Concentration in vacuo followed by drying under vacuum afforded the crude desired product which was used in the subsequent reaction without further purification.

Step B

To a solution of (S)-{1-[4,4-bis-(4-fluoro-phenyl)-butylcarbamoyl]-3-methyl-butyl}-methyl-carbamic acid tert-butyl ester in $CH_2Cl_2$ (15 mL) was added trifluoroacetic acid (5 mL) at ambient temperature under nitrogen atmosphere. The resulting reaction mixture was stirred for 25 minutes, then concentrated in vacuo. The viscous oil obtained was dissolved in 60 mL of $CH_2Cl_2$ and successively washed with saturated aqueous $NaHCO_3$ solution (2×60 mL), brine (2×60 mL), and was dried over $Na_2SO_4$. The $CH_2Cl_2$ solution of free amine was concentrated in vacuo to afford the crude product as a viscous oil which was further purified by flash chromatography (10% methanol in chloroform). The free amine isolated was dissolved in 10 mL of ethyl ether. To this solution was added saturated HCl solution in ethyl ether until no more white precipitate formed. Filtration and drying overnight under vacuum afforded 0.65 g (89%) of pure titled compound as a white foam: mp 70–84° C. APCI-MS m/z 389.0 ($MH^+$).

EXAMPLE 13

Preparation of (S)-4-Methyl-2-[methyl-(3-methyl-but-2-enyl)-amino]-pentanoic acid [4,4-bis-(4-fluoro-phenyl)-butyl]-amide monohydrochloride

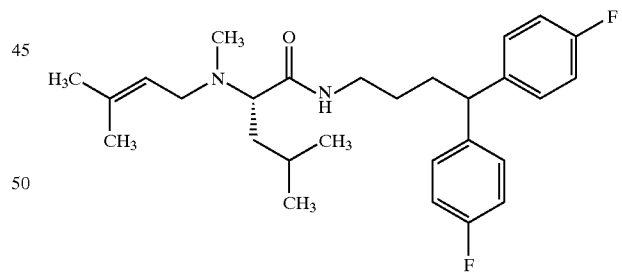

(S)-4-Methyl-2-methylamino-pentanoic acid [4,4-bis-(4-fluoro-phenyl)-butyl]-amide monohydrochloride (0.25 g, 0.59 mmol, Example 12) and 3-methyl-2-butenal (50 mg, 0.59 mmol, Aldrich, Milwaukee, Wis.) were mixed in $CH_2Cl_2$ (10 mL). After stirring at ambient temperature under nitrogen atmosphere for 30 minutes, the solution was cooled to 0° C. in an ice-water bath. To this solution was added sodium triacetoxyborohydride (0.19 g, 0.88 mmol). The resulting reaction mixture was stirred for, in succession, 30 minutes at 0° C. and 12 hours at ambient temperature. Six milliliters of saturated aqueous $NaHCO_3$ solution was added to the reaction mixture, and the resulting mixture was stirred for 5 minutes. The two layers were separated, and the aqueous layer was extracted with $CH_2Cl_2$ (2×10 mL). The combined organic solution was dried over $Na_2SO_4$. The solution was concentrated in vacuo affording a viscous oil. The crude product was purified by flash chromatography (50% EtOAc in hexanes), the mixed fractions were combined, concentrated in vacuo, and purified by preparative plate (50% EtOAc in hexanes). The desired product isolated from flash chromatography and preparative plate were combined and further purified by preparative plate (5% acetonitrile in chloroform, developed twice). The free amine was dissolved in 5 mL of ethyl ether and treated with ethereal HCl to afford 75 mg (28% over 2 steps) of the pure titled compound as a white foam: mp 55–68° C. APCI-MS m/z 456.9 (MH+).

EXAMPLE 14

Preparation of (S)-2-[(4-tert-Butyl-benzyl)-methyl-amino]-4-methyl-pentanoic acid [4,4-bis-(4-fluoro-phenyl)-butyl]-amide monohydrochloride

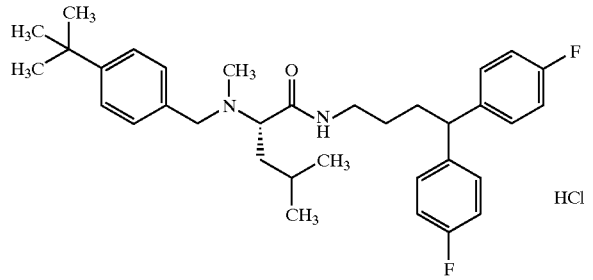

(S)-4-Methyl-2-methylamino-pentanoic acid [4,4-bis-(4-fluoro-phenyl)-butyl]-amide monohydrochloride (0.25 g, 0.58 mmol, Example 12) and 4-t-butylbenzaldehyde (94 mg, 0.58 mmol, Aldrich, Milwaukee, Wis.) were mixed in $CH_2Cl_2$ (10 mL). After stirring at ambient temperature under nitrogen atmosphere for 30 minutes, the solution was cooled to 0° C. in an ice-water bath. To this solution was added sodium triacetoxyborohydride (0.18 g, 0.87 mmol). The resulting reaction mixture was stirred for, in succession, 30 minutes at 0° C. and 12 hours at ambient temperature. Six milliliters of saturated aqueous $NaHCO_3$ solution was added to the reaction mixture, and the resulting mixture was stirred for 5 minutes. The two layers were separated, and the aqueous layer was extracted with $CH_2Cl_2$ (2×10 mL). The combined organic solution was dried over $Na_2SO_4$. The solution was concentrated in vacuo affording a viscous oil. The crude product was purified first by flash chromatography (25% EtOAc in hexanes), then by preparative plate (5% acetonitrile in chloroform). The free amine was dissolved in 5 mL of ethyl ether and treated with ethereal HCl to afford 130 mg (42% over 2 steps) of the pure titled compound as a white foam: mp 87–95° C. APCI-MS m/z 535.0 (MH+).

EXAMPLE 15

Preparation of (S)-2-Cyclohexylamino-4-methyl-pentanoic acid [4,4-bis-(4-fluoro-phenyl)-butyl]-amide monohydrochloride

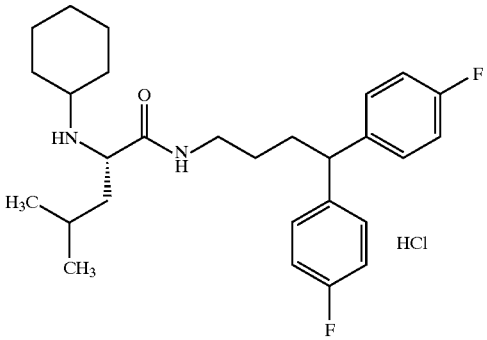

Step A. (S)-2-Cyclohexylamino-4-pentanoic acid

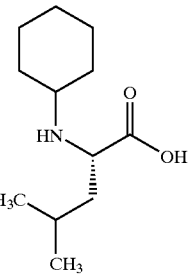

A mixture of L-leucine (100 g, 0.76 mol) and cyclohexanone (149 g, 1.5 mol, Aldrich, Milwaukee, Wis.) was agitated in an atmosphere of hydrogen (pressure, 50 psi) at room temperature in absolute ethanol (1.6 L) in the presence of Pd/C (20%, 8 g) until the absorption of hydrogen almost ceased, filtered. The solid was treated with concentrated aqueous HCl (36.5%) until all the desired product was dissolved in the acidic aqueous solution, the catalyst was then removed by filtration. The filtrate was treated with aqueous NaOH (50%) to adjust the pH to 6.5. White solid precipitated out which was isolated via filtration. The original filtrate, an ethanolic solution, was concentrated in vacuo to dryness to give a white solid. The combined white solid was triturated with a small amount of water at 50° C., the mixture was then filtered at 30–40° C., the white solid was washed with acetone (3×500 mL) and dried under vacuum. One hundred fifty-one grams (93%) of the pure titled compound was isolated as a white solid; mp >280° C. APCI-MS m/z 214.2 (MH+).

Step B

A suspension of (S)-2-cyclohexylamino-4-methyl-pentanoic acid (108 mg, 0.51 mmol) and 4,4-bis-(4-fluoro-phenyl)-butylamine monohydrochloride (151 mg, 0.51 mmol) in dry DMF (4 mL) was treated with Triton® B (0.92 mL, 2.0 mmol, 40 weight percent solution in methanol, Aldrich, Milwaukee, Wis.), then sonicated for a few seconds, a clear solution was obtained. The clear solution was concentrated in vacuo to remove most of the methanol, then cooled to 0° C. in an ice-water bath. Solid O-benzotriazol-1-yl-N,N,N',N'-tetramethyluronium hexafluorophosphate (0.19 g, 0.51 mmol) was then added. After stirring at 0° C. for 20 minutes the cooling bath was removed, and the stirring was continued at ambient temperature for 30 minutes. After this period, the reaction mixture was mixed with 60 mL of diethyl ether; the resulting mixture was successively washed with saturated aqueous NaHCO$_3$ solution (2×50 mL), brine (2×50 mL), and was dried over Na$_2$SO$_4$. The solution was concentrated in vacuo affording a viscous oil. The crude product was purified by flash chromatography (60% EtOAc in hexanes). The free amine was dissolved in 5 mL of ethyl ether and treated with ethereal HCl to afford 150 mg (60%) of the pure titled compound as a white foam; mp 75–85° C. APCI-MS m/z 457.3 (MH$^+$).

EXAMPLE 16

Preparation of (S)-Azepane-1-carboxylic acid {1-[4,4-bis-(4-fluoro-phenyl)-butylcarbamoyl]-2-methyl-butyl}-amide

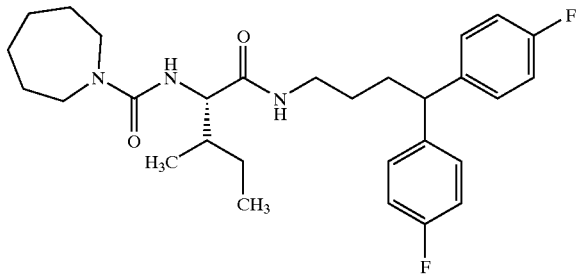

Step A. (S)-2-[(Azepane-1-carbonyl)-amino]-3-methyl-pentanoic acid benzyl ester

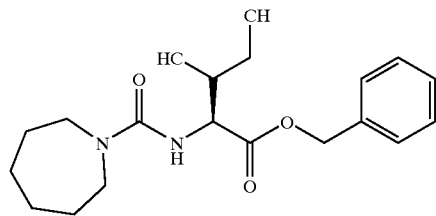

In a manner similar to that described in Example 2 Step A, (S)-2-amino-3-methyl-pentanoic acid benzyl ester (4.89 g, 22.1 mmol) was converted to the title compound (6.09 g, 79%).

Step B. (S)-2-[(Azepane-1-carbonyl)-amino]-3-methyl-pentanoic acid

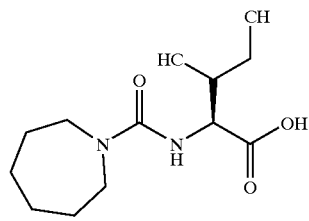

In a manner similar to that described in Example 1, Step B, (S)-2-[(Azepane-1-carbonyl)amino]-3-methyl-pentanoic acid benzyl ester (6.03 g, 17.4 mmol) was converted to the title compound (3.57 g, 80%). APCI-MS m/z 247 (MH$^+$).

Step C (S)-2-[(Azepane-1-carbonyl)-amino]-3-methyl-pentanoic acid (0.300 g, 1.24 mmol) was dissolved in dry DMF (4 mL) under nitrogen atmosphere and cooled to 0° C. in an ice-water bath. To this solution were added, in succession, N,N-diisopropylethylamine (0.647 mL, 3.71 mmol) and solid O-benzotriazol-1-yl-N,N,N',N'-tetramethyluronium hexafluorophosphate (0.470 g, 1.24 mmol). The resulting reaction mixture was stirred at that temperature for 30 minutes; solid 4,4-bis-(4-fluoro-phenyl)-butylamine mono-hydrochloride (0.369 g, 1.24 mmol) was then added. After stirring for, sequentially, 15 minutes at 0° C. and 25 minutes at ambient temperature, reaction mixture was mixed with 60 mL of diethyl ether; the resulting mixture was successively washed with saturated aqueous NaHCO$_3$ solution (2×60 mL), brine (2×60 mL), and was dried over Na$_2$SO$_4$. The solution was concentrated in vacuo affording a viscous oil. The crude product was further purified by flash chromatography (60% EtOAc in hexane) to provide 0.50 g (81%) of the pure titled compound as a white foam; mp 50–60° C. APCI-MS m/z 500.3 (MH$^+$).

EXAMPLE 17

Preparation of (S)-4-Phenyl-piperazine-1-carboxylic acid {1-[4,4-bis-(4-fluoro-phenyl)-butylcarbamoyl]-3-methyl-butyl}-amide

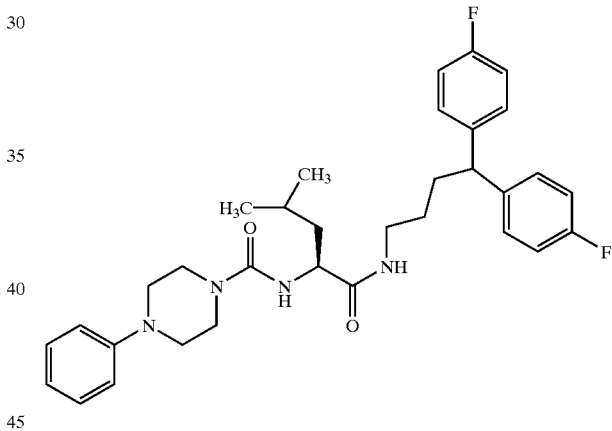

Step A. (S)-4-Methyl-2-[(4-phenyl-piperazine-1-carbonyl)-amino]pentanoic acid benzyl ester

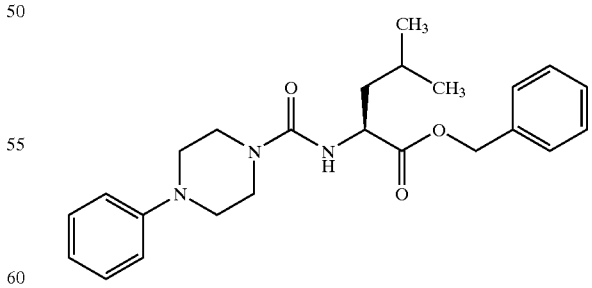

In a manner similar to that described in Example 2, Step A, (S)-2-amino-4-methyl-pentanoic acid benzyl ester (2.80 g, 12.7 mmol) and N-phenylpiperazine (4.12 g, 25.4 mmol) were converted to the title compound (3.8 g, 73%), mp 88° C.

Step B. (S)-4-Methyl-2-[(4-phenyl-piperazine-1-carbonyl)-amino]pentanoic acid

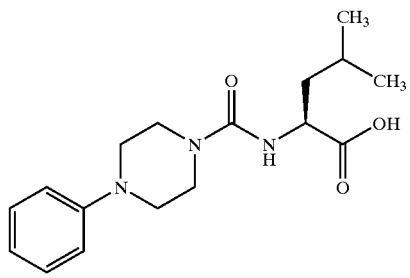

In a manner similar to that described in Example 1, Step B, (S)-4-methyl-2-[(4-phenyl-piperazine-1-carbonyl)-amino]-pentanoic acid benzyl ester (2.8 g, 6.78 mmol) was converted to the title compound (0.93 g, 43%). APCI-MS m/z 321 (MH$^+$).

Step C (S)-4-Methyl-2-[(4-phenyl-piperazine-1-carbonyl)-amino]pentanoic acid (0.300 g, 0.940 mmol) was dissolved in dry DMF (4 mL) under nitrogen atmosphere and cooled to 0° C. in an ice-water bath. To this solution were added, in succession, N,N-diisopropylethylamine (0.490 mL, 2.81 mmol) and solid O-benzotriazol-1-yl-N,N,N,',N'-tetramethyluronium hexafluorophosphate (0.356 g, 0.939 mmol). The resulting reaction mixture was stirred at that temperature for 30 minutes; solid 4,4-bis-(4-fluoro-phenyl)-butylamine monohydrochloride (0.280 g, 0.940 mmol) was then added. After stirring for, sequentially, 10 minutes at 0° C. and 35 minutes at ambient temperature, reaction mixture was mixed with 60 mL of diethyl ether; the resulting mixture was successively washed with saturated aqueous NaHCO$_3$ solution (2×60 mL), brine (2×60 mL), and was dried over Na$_2$SO$_4$. The solution was concentrated in vacuo affording a solid. Recrystallization from ether afforded 0.18 g (34%) of the pure titled compound as a white solid; mp 138–141° C. APCI-MS m/z 563.4 (MH$^+$).

EXAMPLE 18

Preparation of (S)-4-Methyl-2-(tetrahydro-pyran-4-ylamino)-pentanoic acid [4,4-bis-(4-fluoro-phenyl)-butyl]-amide

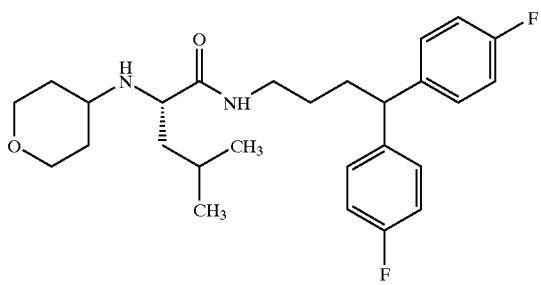

Step A. (S)-4-Methyl-2-(tetrahydro-pyran-4-ylamino)-pentanoic acid

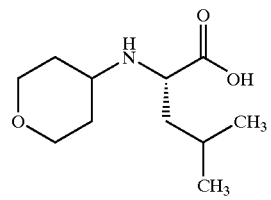

A mixture of L-leucine (20.0 g, 152 mmol), concentrated aqueous HCl solution (13.1 mL, 36.5%), and tetrahydro-4H-pyran-4-one (30.0 g, 300 mmol, Aldrich, Milwaukee, Wis.) was agitated in an atmosphere of hydrogen (pressure, 43–51 psi) at room temperature in a mixture of ethanol and water (1:1, v/v, 400 mL) in the presence of Pd/C (20%, 4 g) until the absorption of hydrogen almost ceased, filtered. The filtrate was treated with concentrated aqueous ammonium hydroxide (29.8%) to adjust the pH to 5.5. White solid precipitated out which was isolated via filtration. The white solid was mixed with 150 mL of water and heated to boiling. After cooling down to 0° C., the white solid was filtered and dried under vacuum affording 17.5 g (53.4%) of the pure titled compound as a white solid; mp >300° C. APCI-MS m/z 216.2 (MH$^+$).

Step B

A suspension of (S)-4-methyl-2-(tetrahydro-pyran-4-ylamino)-pentanoic acid (430 mg, 2.00 mmol), N-methylmorpholine (0.220 mL, 2.00 mmol), and 4,4-bis-(4-fluoro-phenyl)-butylamine monohydrochloride (597 mg, 2.00 mmol) in dry DMF (10 mL) was treated with Triton® B (1.82 mL, 4.00 mmol, 40 weight percent solution in methanol, Aldrich, Milwaukee, Wis.), a clear solution was obtained and cooled to 0° C. in an ice-water bath. Solid O-benzotriazol-1-yl-N,N,N',N'-tetramethyluronium hexafluorophosphate (0.760 g, 2.00 mmol) was then added. After stirring at 0° C. for 30 minutes, was added, the cooling bath was then removed, and the stirring was continued at ambient temperature for 30 minutes. After this period, the reaction mixture was mixed with 50 mL of diethyl ether; the resulting mixture was successively washed with saturated aqueous NaHCO$_3$ solution (50 mL), brine (2×50 mL), and was dried over Na$_2$SO$_4$. The solution was concentrated in vacuo affording a viscous oil. The crude product was purified by flash chromatography (EtOAc:hexanes:MeOH 50:50:5) to give 300 mg (39%) of the pure titled compound as a clear oil. APCI-MS m/z 459.4 (MH$^+$).

Anal. C$_{27}$H$_{35}$N$_2$O$_2$F$_2$.0.4H$_2$O: C, 69.77; H, 7.76; N, 6.03; H$_2$O, 1.55. Found: C, 69.81; H. 7.76; N, 5.74; H$_2$O, 1.61.

EXAMPLE 19

Preparation of (S)-2-Isopropylamino-4-methyl-pentanoic acid [4,4-bis-(4-fluoro-phenyl)-butyl]-amide monohydrochloride

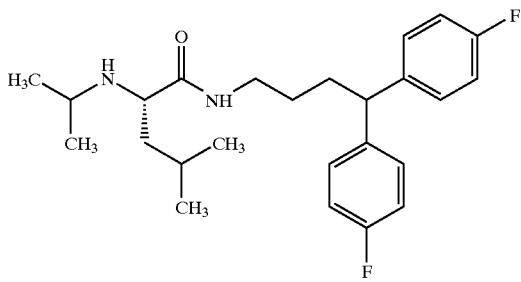

Step A. (S)-2-Isopropylamino-4-methyl-pentanoic acid

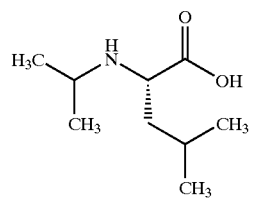

A mixture of L-leucine (5.0 g, 38 mmol) and acetone (5.6 mL, 76 mmol) was agitated in an atmosphere of hydrogen (pressure, 33–52 psi) at room temperature in absolute ethanol (100 mL) in the presence of Pd/C (20%, 1 g) until the absorption of hydrogen almost ceased. Four milliliters of concentrated HCl (aq, 36.5%) was then added and stirred for 10 minutes; the catalyst was then removed by filtration. The filtrate was treated with aqueous ammonium hydroxide (29.8%) to adjust the pH to 6.5. White solid precipitated out which was isolated via filtration. The white solid was mixed with 100 mL of water and heated to boiling on a hot plate. After cooling down to 0° C., the white solid was filtered and dried under vacuum. Forty percent (2.6 g) of the pure titled compound was isolated as a white solid; mp 293–296° C. APCI-MS m/z 174.2 (MH$^+$).

Step B

A suspension of (S)-2-isopropylamino-4-methyl-pentanoic acid (433 mg, 2.50 mmol), N-methylmorpholine (0.275 mL, 2.50 mmol), and 4,4-bis-(4-fluoro-phenyl)-butylamine monohydrochloride (750 mg, 2.52 mmol) in dry DMF (12 mL) was treated with Triton® B (2.27 mL, 4.99 mmol, 40 wt percent solution in methanol, Aldrich, Milwaukee, Wis.), a clear solution was obtained and cooled to 0° C. in an ice-water bath. Solid O-benzotriazol-1-yl-N,N,N',N'-tetramethyluronium hexafluorophosphate (0.940 g, 2.50 mmol) was then added. After stirring at 0° C. for 90 minutes the cooling bath was removed, and the stirring was continued at ambient temperature for 30 minutes. After this period, the reaction mixture was mixed with 100 mL of diethyl ether; the resulting mixture was successively washed with saturated aqueous NaHCO$_3$ solution (100 mL), brine (100 mL), and was dried over Na$_2$SO$_4$. The solution was concentrated in vacuo affording a viscous oil. The crude product was purified by flash chromatography (EtOAc:hexanes:MeOH 50:50:5). The free amine was dissolved in 5 mL of ethyl ether and treated with ethereal HCl to afford 368 mg (35%) of the pure titled compound as a white foam: mp 100–103° C.

Anal. C$_{25}$H$_{34}$N$_2$OF$_2$.1.0HCl: C, 66.28; H, 7.79; N, 6.18; F, 8.39; Cl, 7.83. Found: C, 66.22; H, 7.72; N, 5.80; F, 8.37; Cl, 7.51.

EXAMPLE 20

Preparation of (S)-2-Dimethylamino-4-methyl-pentanoic acid [4,4-bis-(4-fluoro-phenyl)-butyl]-amide monohydrochloride

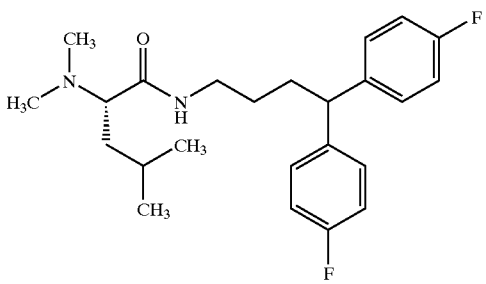

Step A. (S)-2-Dimethylamino-4-methyl-pentanoic acid

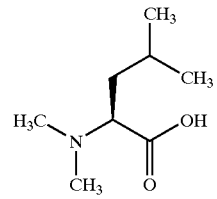

Synthesized according to the procedure described in *J. Chem. Soc.*, 1950:1342–1345.

Step B

A solution of (S)-2-dimethylamino-4-methyl-pentanoic acid (433 mg, 2.72 mmol), N-methylmorpholine (0.275 mL, 2.50 mmol), and 4,4-bis-(4-fluoro-phenyl)-butylamine monohydrochloride (809 mg, 2.72 mmol) in dry DMF (12 mL) was treated with Triton® B (1.80 mL, 3.96 mmol, 40 weight percent solution in methanol, Aldrich, Milwaukee, Wis.). The clear solution was cooled to 0° C. in an ice-water bath. Solid O-benzotriazol-1-yl-N,N,N',N'-tetramethyluronium hexafluorophosphate (1.03 g, 2.72 mmol) was then added. After stirring at 0° C. for 30 minutes, the cooling bath was removed, and the stirring was continued at ambient temperature for 15 minutes. After this period, the reaction mixture was mixed with 60 mL of diethyl ether, white precipitate forms and was removed by filtration. The filtrate was successively washed with saturated aqueous NaHCO$_3$ solution (50 mL), brine (2×50 mL), and was dried over Na$_2$SO$_4$. The solution was concentrated in vacuo affording a viscous oil. The crude product was purified by flash chromatography (5% MeOH in 1:1 EtOAc/hexanes). The free amine was dissolved in 5 mL of ethyl ether and treated with ethereal HCl to afford 361 mg (30%) of the pure titled compound as a white foam; mp 60–72° C. APCI-MS m/z 403.3 (MH$^+$).

EXAMPLE 21

Preparation of (S)-2-(Cyclohexyl-methyl-amino)-4-methyl-pentanoic acid [4,4-bis-(4-fluoro-phenyl)-butyl]-amide monohydrochloride

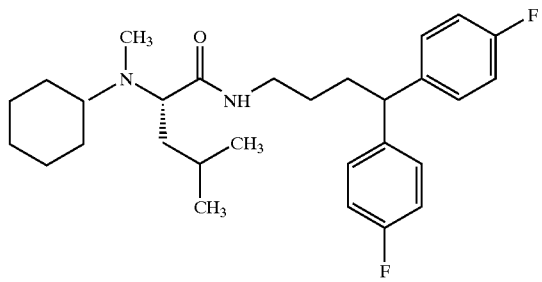

Step A. (S)-2-(Cyclohexyl-methyl-amino)-4-methyl-pentanoic acid

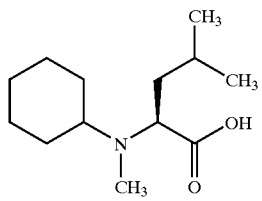

A mixture of (S)-2-cyclohexylamino-4-methyl-pentanoic acid (6.4 g, 30 mmol) and aqueous HCHO (7 mL of 37.2%, 2.6 g, 87 mmol) was agitated in an atmosphere of hydrogen (pressure, 6–51 psi) at 50° C. in absolute ethanol (250 mL) in the presence of Pd/C (20%, 1 g) until the absorption of hydrogen almost ceased. The catalyst was removed by filtration. The filtrate was concentrated in vacuo to dryness. Fifty milliliters of water was added and concentrated to dryness, and this operation was repeated twice to remove most of HCHO. The white solid collected was triturated with hot acetone, then cooled to 0° C. for 10 minutes. Filtration and drying under vacuum gave 5.0 g (73%) of the desired product as a white solid; mp 185–187° C. APCI-MS m/z 228.2 (MH$^+$).

Step B (S)-2-(Cyclohexyl-methyl-amino)-4-methyl-pentanoic acid (0.300 g, 1.32 mmol) was dissolved in dry DMF (4 mL) under nitrogen atmosphere and cooled to 0° C. in an ice-water bath. To this solution were added, in succession, N,N-diisopropylethylamine (0.690 mL, 3.96 mmol) and solid O-benzotriazol-1-yl-N,N,N',N'-tetramethyluronium hexafluorophosphate (0.501 g, 1.32 mmol). The resulting reaction mixture was stirred at that temperature for 40 minutes; solid 4,4-bis-(4-fluoro-phenyl)-butylamine monohydrochloride (0.393 g, 1.32 mmol) was then added. After stirring for, sequentially, 15 minutes at 0° C. and 30 minutes at ambient temperature, reaction mixture was mixed with 60 mL of diethyl ether; the resulting mixture was successively washed with saturated aqueous NaHCO$_3$ solution (2×60 mL), brine (2×60 mL), and was dried over Na$_2$SO$_4$. The solution was concentrated in vacuo affording an oil. The crude product was further purified by flash chromatography (50% EtOAc in hexane) and treated with ethereal HCl. Subsequent concentration in vacuo and drying under vacuum provided 0.51 g (75%) of the pure titled compound as a white foam; mp 73–83° C. APCI-MS m/z 471.4 (MH$^+$).

EXAMPLE 22

Preparation of (S)-4-Methyl-2-piperidin-1-yl-pentanoic acid [4,4-bis-(4-fluoro-phenyl)-butyl]-amide

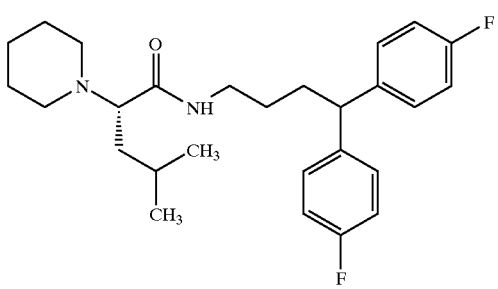

Step A. (S)-4-Methyl-2-piperidin-1-yl-pentanoic acid monohydrobromide

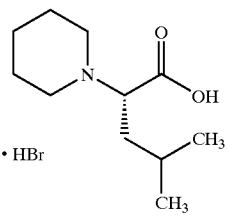

Synthesized according to the procedure described in *Acta Poloniae Pharmaceutica—Drug Research*, 1994;51:227–229.

Step B (S)-4-Methyl-2-piperidin-1-yl-pentanoic acid monohydrobromide (0.300 g, 1.51 mmol) was dissolved in dry DMF (4 mL) under nitrogen atmosphere and cooled to 0° C. in an ice-water bath. To this solution were added, in succession, N,N-diisopropylethylamine (0.787 mL, 4.52 mmol) and solid O-benzotriazol-1-yl-N,N,N',N'-tetramethyluronium hexafluorophosphate (0.571 g, 1.51 mmol). The resulting reaction mixture was stirred at that temperature for 30 minutes; solid 4,4-bis-(4-fluoro-phenyl)-butylamine monohydrochloride (0.448 g, 1.51 mmol) was then added. After stirring for, sequentially, 10 minutes at 0° C. and 45 minutes at ambient temperature, reaction mixture was mixed with 60 mL of diethyl ether; the resulting mixture was successively washed with saturated aqueous NaHCO$_3$ solution (2×60 mL), brine (2×60 mL), and was dried over Na$_2$SO$_4$. The solution was concentrated in vacuo affording an viscous oil. The crude product was further purified by flash chromatography (50% EtOAc in hexane) and treated with ethereal HCl. Subsequent concentration in vacuo and drying under vacuum provided 0.4 g (54%) of the pure titled compound as a white foam; mp 52–70° C. APCI-MS m/z 443.4 (MH$^+$).

EXAMPLE 23

Preparation of (S)-4-Methyl-2-morpholin-4-yl-pentanoic acid [4,4-bis-(4-fluoro-phenyl)-butyl]-amide monohydrochloride

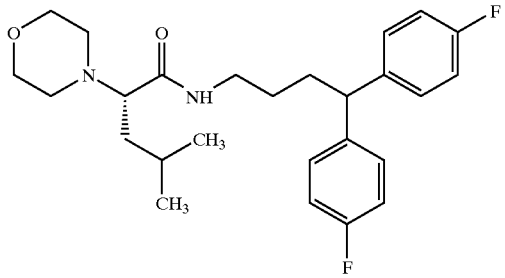

Step A. (S)-4-Methyl-2-morpholin-4-yl-pentanoic acid

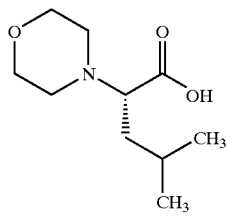

Synthesized according to the procedure described in *Acta Poloniae Pharmaceutica—Drug Research*, 1994;51:227–229.

Step B (S)-4-Methyl-2-morpholin-4-yl-pentanoic acid (0.300 g, 1.49 mmol) was dissolved in dry DMF (4 mL) under nitrogen atmosphere and cooled to 0° C. in an ice-water bath. To this solution were added, in succession, N,N-diisopropylethylamine (0.779 mL, 4.47 mmol) and solid O-benzotriazol-1-yl-N,N,N',N'-tetramethyluronium hexafluorophosphate (0.565 g, 1.49 mmol). The resulting reaction mixture was stirred at that temperature for 30 minutes; solid 4,4-bis-(4-fluoro-phenyl)butylamine monohydrochloride (0.444 g, 1.49 mmol) was then added. After stirring for, sequentially, 10 minutes at 0° C. and 45 minutes at ambient temperature, reaction mixture was mixed with 60 mL of diethyl ether; the resulting mixture was successively washed with saturated aqueous NaHCO$_3$ solution (2×60 mL), brine (2×60 mL), and was dried over Na$_2$SO$_4$. The solution was concentrated in vacuo affording an viscous oil. The crude product was further purified by flash chromatography (70% EtOAc in hexane) and treated with ethereal HCl. Subsequent concentration in vacuo and drying under vacuum provided 0.55 g (75%) of the pure titled compound as a white foam; mp 63–78° C. APCI-MS m/z 445.4 (MH$^+$).

EXAMPLE 24

Preparation of (S)-4-Methyl-2-piperidin-1-yl-pentanoic acid (3,3-diphenyl-propyl)-amide monohydrochloride

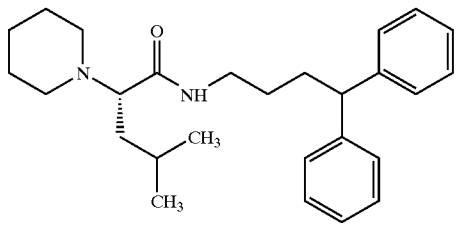

(S)-4-Methyl-2-piperidin-1-yl-pentanoic acid monohydrobromide (0.300 g, 1.51 mmol, Example 22, Step A) was dissolved in dry DMF (4 mL) under nitrogen atmosphere and cooled to 0° C. in an ice-water bath. To this solution were added, in succession, N,N-diisopropylethylamine (0.524 mL, 3.01 mmol) and solid O-benzotriazol-1-yl-N,N,N',N'-tetramethyluronium hexafluorophosphate (0.571 g, 1.51 mmol). The resulting reaction mixture was stirred at that temperature for 30 minutes; 3,3-diphenylpropylamine (0.318 g, 1.50 mmol) was then added. After stirring for, sequentially, 10 minutes at 0° C. and 45 minutes at ambient temperature, reaction mixture was mixed with 60 mL of diethyl ether; the resulting mixture was successively washed with saturated aqueous NaHCO$_3$ solution (2×60 mL), brine (2×60 mL), and was dried over Na$_2$SO$_4$. The solution was concentrated in vacuo affording an viscous oil. The crude product was further purified by flash chromatography (60% EtOAc in hexane) and treated with ethereal HCl. Subsequent concentration in vacuo and drying under vacuum provided 0.39 g (59%) of the pure titled compound as a white foam: mp 58–65° C. APCI-MS m/z 393.3 (MH$^+$).

EXAMPLE 25

Preparation of (S)-2-(Cyclohexyl-methyl-amino)-4-methyl-pentanoic acid (3,3-diphenyl-propyl)-amide monohydrochloride

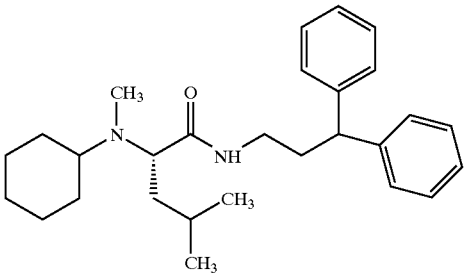

(S)-2-(Cyclohexyl-methyl-amino)-4-methyl-pentanoic acid (0.300 g, 1.32 mmol, Example 21, Step A) was dissolved in dry DMF (4 mL) under nitrogen atmosphere and cooled to 0° C. in an ice-water bath. To this solution were added, in succession, N,N-diisopropylethylamine (0.460 mL, 2.63 mmol) and solid O-benzotriazol-1-yl-N,N,N',N'-tetramethyluronium hexafluorophosphate (0.501 g, 1.32 mmol). The resulting reaction mixture was stirred at that temperature for 30 minutes; 3,3-diphenylpropylamine (0.279 g, 1.32 mmol) was then added. After stirring for, sequentially, 15 minutes at 0° C. and 30 minutes at ambient temperature, reaction mixture was mixed with 60 mL of diethyl ether; the resulting mixture was successively washed with saturated aqueous NaHCO$_3$ solution (2×60 mL), brine (2×60 mL), and was dried over Na$_2$SO$_4$. The solution was concentrated in vacuo affording an viscous oil. The crude product was further purified by flash chromatography (40% EtOAc in hexane) and treated with ethereal HCl. Subsequent concentration in vacuo and drying under vacuum provided 0.31 g (50%) of the pure titled compound as a white foam: mp 67–86° C.; APCI-MS m/z 421.4 (MH$^+$).

EXAMPLE 26

Preparation of (S)-Azepane-1-carboxylic acid {1-[4,4-bis-(4-fluoro-phenyl)-butylcarbamoyl]-2-methyl-propyl}-amide

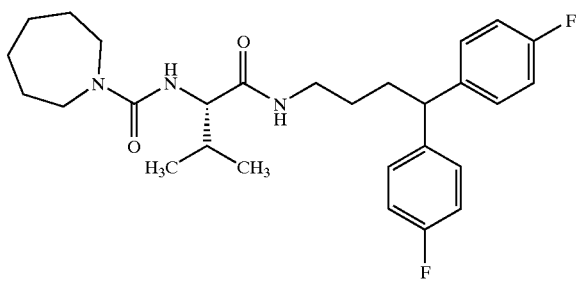

Step A. (S)-2-[(Azepane-1-carbonyl)-amino]-3-methyl-butanoic acid benzyl ester

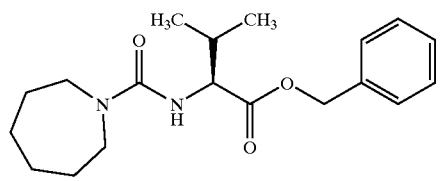

In a manner similar to that described in Example 2, Step A, (S)-2-amino-3-methyl butanoic acid benzyl ester (8.79 g, 42.1 mmol) was converted to the title compound (2.43 g, 17%). APCI-MS m/z 332 (MH$^+$).

Step B. (S)-2-[(Azepane-1-carbonyl)-amino]-3-methyl-butanoic acid

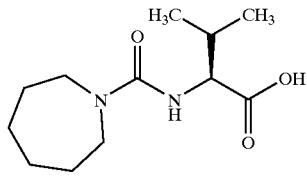

In a manner similar to that described in Example 2, Step B, (S)-2-[(azepane-1-carbonyl)amino]-3-methyl-butanoic acid benzyl ester (2.33 g, 7.01 mmol) was converted to the title compound (1.40 g, 82%).

Step C (S2-[(Azepane-1-carbonyl)-amino]-3-methyl-butanoic acid (0.300 g, 1.23 mmol) was dissolved in dry DMF (4 mL) under nitrogen atmosphere and cooled to 0° C. in an ice-water bath. To this solution were added, in succession, N,N-diisopropylethylamine (0.647 mL, 3.71 mmol) and solid O-benzotriazol-1-yl-N,N,N',N'-tetramethyluronium hexafluorophosphate (0.470 g, 1.24 mmol). The resulting reaction mixture was stirred at that temperature for 30 minutes; solid 4,4-bis-(4-fluoro-phenyl)-butylamine mono-hydrochloride (0.369 g, 1.24 mmol) was then added. After stirring for, sequentially, 15 minutes at 0° C. and 50 minutes at ambient temperature, reaction mixture was mixed with 60 mL of diethyl ether; the resulting mixture was successively washed with saturated aqueous NaHCO$_3$ solution (2×60 mL), brine (2×60 mL), and was dried over Na$_2$SO$_4$. The solution was concentrated in vacuo affording an viscous oil. The crude product was further purified by flash chromatography (60% EtOAc in hexane) to provide 0.31 g (51%) of the pure titled compound as a white foam: mp 32–50° C. APCI-MS m/z 486.3 (MH$^+$).

EXAMPLE 27

Preparation of (S)-4-Methyl-2-[methyl-(tetrahydro-pyran-4-yl)-amino]-pentanoic acid [4,4-bis-(4-fluoro-phenyl)-butyl]-amide monohydrochloride

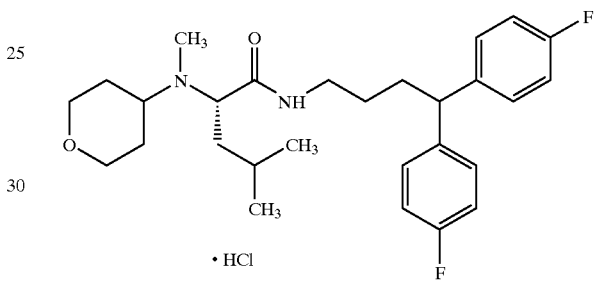

Step A. (S)-4-Methyl-2-[methyl-(tetrahydro-pyran-4-yl)-amino]-pentanoic acid

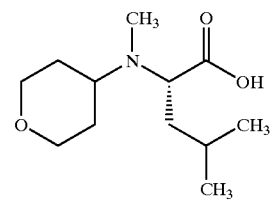

A mixture of (S)-4-methyl-2-(tetrahydro-pyran-4-ylamino)-pentanoic acid (9.09 g, 42.3 mmol, Example 18, Step A) and aqueous HCHO (10 mL of 37.2%, 3.72 g, 124 mmol) was agitated in an atmosphere of hydrogen (pressure, 47–52 psi) at 50° C. in absolute ethanol (250 mL) in the presence of Pd/C (20%, 1 g) until the absorption of hydrogen almost ceased. The catalyst was removed by filtration. The filtrate was concentrated in vacuo to dryness. Fifty milliliter of water was added and concentrated to dryness, and this operation was repeated twice to remove most of HCHO. Absolute ethanol (50 mL) was then added and concentrated to dryness to remove residual water. The white solid collected was triturated with acetone. Filtration and drying under vacuum gave 8.93 g (92%) of the desired product as a white solid; mp 185–190° C. (decomposed). APCI-MS m/z 230.2 (MH$^+$).

Step B (S)-4-Methyl-2-[methyl-(tetrahydro-pyran-4-yl)-amino]-pentanoic acid (0.300 g, 1.31 mmol) was dissolved in dry DMF (4 mL) under nitrogen atmosphere and cooled to 0° C. in an ice-water bath. To this solution were added, in succession, N,N-diisopropylethylamine (0.684 mL, 3.93 mmol) and solid O-benzotriazol-1-yl-N,N,N',N'-tetramethyluronium hexafluorophosphate (0.496 g, 1.31 mmol). The resulting reaction mixture was stirred at that temperature for 25 minutes; solid 4,4-bis-(4-fluoro-phenyl)-butylamine monohydrochloride (0.390 g, 1.31 mmol) was then added. After stirring for, sequentially, 15 minutes at 0° C. and 30 minutes at ambient temperature, reaction mixture was mixed with 60 mL of diethyl ether; the resulting mixture was successively washed with saturated aqueous NaHCO$_3$ solution (2×60 mL), brine (2×60 mL), and was dried over Na$_2$SO$_4$. The solution was concentrated in vacuo affording an viscous oil. The crude product was further purified by flash chromatography (70% EtOAc in hexane) and treated with ethereal HCl. Subsequent concentration in vacuo and drying under vacuum provided 0.432 g (63%) of the pure titled compound as a white foam; mp 75–92° C. APCI-MS m/z 473.4 (MH$^+$).

EXAMPLE 28

Preparation of (S)-4-Methyl-2-[methyl-(3-methyl-butyl)-amino]-pentanoic acid [4,4-bis-(4-fluoro-phenyl)-butyl]-amide monohydrochloride

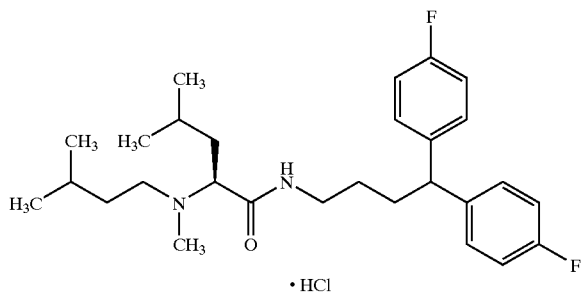

Step A. (S)-2-(Isobutyl-methyl-amino)-4-methyl-pentanoic acid

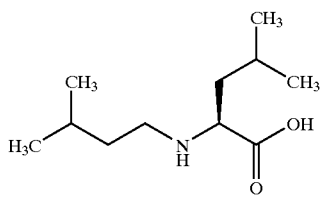

A mixture of L-leucine (100 g, 0.76 mol) and isovaleraldehyde (132 g, 1.53 mol, Aldrich, Milwaukee, Wis.) was agitated in an atmosphere of hydrogen (pressure, 50 psi) at room temperature in absolute ethanol (1.6 L) in the presence of Pd/C (20%, 8 g) until the absorption of hydrogen almost ceased, filtered. The solid was treated with concentrated aqueous HCl (36.5%) until all the desired product was dissolved in the acidic aqueous solution, the catalyst was then removed by filtration. The filtrate was treated with aqueous NaOH solution (50%) to adjust the pH to 6.5. White solid precipitated out which was isolated via filtration. The white solid was triturated, in succession, with 200 mL of water and 300 mL of acetone. After drying under vacuum. 50.0 g (33%) of the pure titled compound was isolated as a white solid: mp 275° C. (decomposed).

Anal. calculated for C$_{11}$H$_{23}$NO$_2$: C, 65.63; H, 11.52; N, 6.96. Found: C, 65.50; H, 11.40; N, 6.88.

Step B. (S)-4-Methyl-2-[methyl-(3-methyl-butyl)-amino]-pentanoic acid

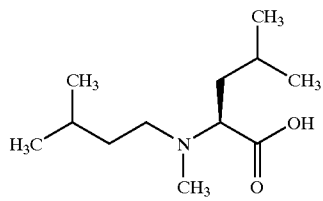

A mixture of (S)-2-(isobutyl-methyl-amino)-4-methyl-pentanoic acid (48.0 g, 239 mmol) and aqueous HCHO (50 mL of 37.2%, 18.6 g, 620 mmol) was agitated in an atmosphere of hydrogen (pressure, 50 psi) at 50° C. in absolute ethanol (1.5 L) in the presence of Pd/C (20%, 3 g) until the absorption of hydrogen almost ceased. The catalyst was removed by filtration. The filtrate was concentrated in vacuo to dryness. Thirty milliliters of water was added and concentrated to dryness, and this operation was repeated three times to remove most of HCHO. The white solid collected was triturated with hot acetone, then cooled to ambient temperature. Filtration and drying under vacuum gave 40.0 g (79%) of the desired product as a white solid; mp 159–1 60° C. (decomposed).

Anal. C$_{12}$H$_{25}$NO$_2$: C, 66.93; H, 11.70; N, 6.50. Found: C, 66.72; H, 11.99; N, 6.45.

Step C (S)-4-Methyl-2-[methyl-(3-methyl-butyl)-amino]-pentanoic acid (0.300 g, 1.39 mmol) was dissolved in dry DMF (4 mL) under nitrogen atmosphere and cooled to 0° C. in an ice-water bath. To this solution were added, in succession, N,N-diisopropylethylamine (0.728 mL, 4.18 mmol) and solid O-benzotriazol-1-yl-N,N,N",N'-tetramethyluronium hexafluorophosphate (0.528 g, 1.39 mmol). The resulting reaction mixture was stirred at that temperature for 25 minutes; solid 4,4-bis-(4-fluoro-phenyl)-butylamine monohydrochloride (0.415 g, 1.39 mmol) was then added. After stirring for, sequentially, 20 minutes at 0° C. and 60 minutes at ambient temperature, reaction mixture was mixed with 60 mL of diethyl ether; the resulting mixture was successively washed with saturated aqueous NaHCO$_3$ solution (2×60 mL), brine (2×60 mL), and was dried over Na$_2$SO$_4$. The solution was concentrated in vacuo affording an viscous oil. The crude product was further purified by flash chromatography (40% EtOAc in hexane) and treated with ethereal HCl. Subsequent concentration in vacuo and drying under vacuum provided 0.460 g (65%) of the pure titled compound as a white foam: mp 37–46° C. APCI-MS m/z 459.4 (MH$^+$).

EXAMPLE 29

Preparation of (S)-4-Methyl-piperazine-1-carboxylic acid {1-[4,4-bis-(4-fluoro-phenyl)-butylcarbamoyl]-3-methyl-butyl)-amide

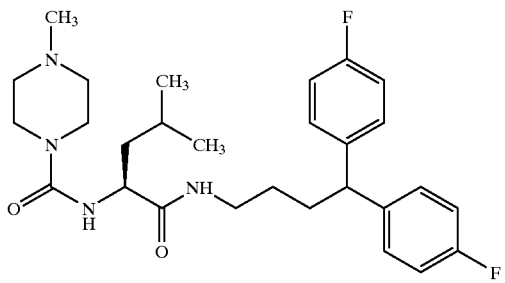

Step A. (S)-2-[(4-methyl-piperazine-1-carbonyl)-amino]-4-methyl pentanoic acid benzyl ester

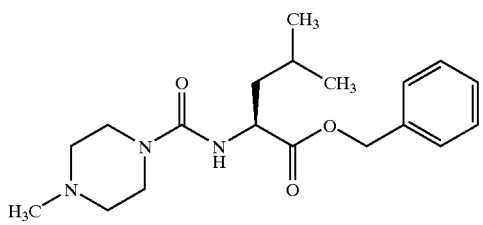

In a manner similar to that described in Example 2 Step A, (S)-2-amino-4-methyl-pentanoic acid benzyl ester (3.01 g, 13.6 mmol) and N-methlypiperazine (1.63 g, 16.3 mmol) were converted to the title compound (3.17 g, 67%).

Step B. (S)-2-[(4-Methyl-piperazine-1-carbonyl)-amino]-4-methyl pentanoic acid

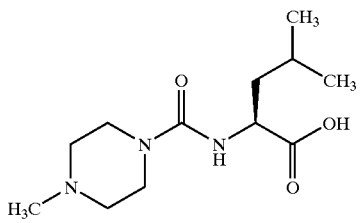

In a manner similar to that described in Example 1, Step B, (S)-2-[(4-methyl-piperazine-1-carbonyl)-amino]-4-methyl-pentanoic acid benzyl ester (1.70 g, 4.89 mmol) was converted to the title compound (0.95 g, 77%).

Anal. $C_{12}H_{23}N_3O_3$: C, 56.03; H, 8.95; N, 16.34. Found: C, 55.85; H, 8.87; N, 16.21.

Step C (S)-2-[(4-Methyl-piperazine-1-carbonyl)-amino]-4-methyl pentanoic acid (0.300 g, 1.23 mmol) was dissolved in dry DMF (4 mL) under nitrogen atmosphere and cooled to 0° C. in an ice-water bath. To this solution were added, in succession, N,N-diisopropylethylamine (0.644 mL, 3.70 mmol) and solid O-benzotriazol-1-yl-N,N,N',N'-tetramethyluronium hexafluorophosphate (0.468 g, 1.23 mmol). The resulting reaction mixture was stirred at that temperature for 30 minutes; solid 4,4-bis-(4-fluoro-phenyl)-butylamine monohydrochloride (0.367 g, 1.23 mmol) was then added. After stirring for, sequentially, 10 minutes at 0° C. and 20 minutes at ambient temperature, reaction mixture was mixed with 60 mL of diethyl ether; the resulting mixture was successively washed with saturated aqueous $NaHCO_3$ solution (2×60 mL), brine (2×60 mL), and was dried over $Na_2SO_4$. The solution was concentrated in vacuo affording an viscous oil. The crude product was further purified by flash chromatography (20% MeOH in EtOAc) to afford 0.45 g (73%) of the pure titled compound as a white foam; mp 73–91° C. APCI-MS m/z 501.3 (MH+).

EXAMPLE 30

Preparation of (S)-Azepane-1-carboxylic acid {1-[4,4-bis-(4-fluoro-phenyl)-butylcarbamoyl]-ethyl}-amide

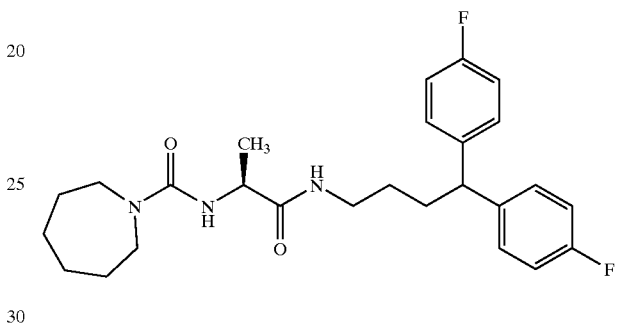

Step A. (S)-2-[(Azepane-1-carbonyl)-amino]-propanoic acid benzyl ester

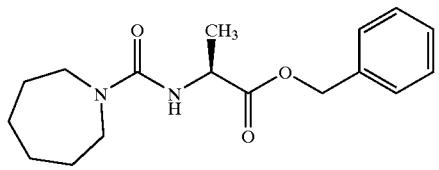

In a manner similar to that described in Example 2, Step A, alanine benzyl ester (15.0 g, 69.6 mmol) was converted to the title compound (9.00 g, 42%). APCI-MS m/z 306 (MH+).

Step B. (S)-2-[(Azepane-1-carbonyl)-amino]-propanoic acid

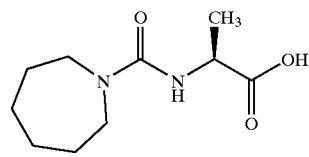

In a manner similar to that described in Example 1, Step B, (S)-2-[(azepane-1-carbonyl)-amino]-propanoic acid benzyl ester (9.00 g, 31.0 mmol) was converted to the title compound (4.90 g, 77%). APCI-MS m/z 215 (MH+).

Step C (S)-2-[(Azepane-1-carbonyl)-amino]-propanoic acid (0.300 g, 1.40 mmol) was dissolved in dry DMF (4 mL) under nitrogen atmosphere and cooled to 0° C. in an ice-water bath. To this solution were added, in succession, N,N-diisopropylethylamine (0.732 mL, 4.20 mmol) and solid O-benzotriazol-1-yl-N,N,N',N'-tetramethyluronium hexafluorophosphate (0.531 g, 1.40 mmol). The resulting reaction mixture was stirred at that temperature for 35 minutes; solid 4,4-bis-(4-fluoro-phenyl)-butylamine monohydrochloride (0.412 g, 1.40 mmol) was then added. After stirring for, sequentially, 10 minutes at 0° C. and 40 minutes at ambient temperature, reaction mixture was mixed with 60 mL of diethyl ether; the resulting mixture was successively washed with saturated aqueous NaHCO$_3$ solution (2×60 mL), brine (2×60 mL), and was dried over Na$_2$SO$_4$. The solution was concentrated in vacuo affording an viscous oil. The crude product was further purified by flash chromatography (70% EtOAc in hexanes) to afford 0.42 g (65%) of the pure titled compound as a white foam: mp 29–49° C. APCI-MS m/z 458.3 (MH$^+$).

EXAMPLE 31

Preparation of (S)-Azepane-1-carboxylic acid (1-{4-[bis-(4-fluoro-phenyl)-methyl]-piperazine-1-carbonyl}-3-methyl-butyl)-amide

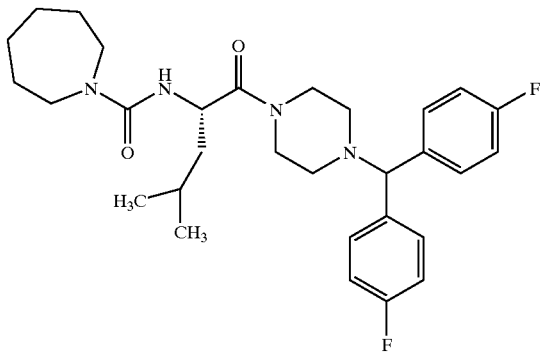

(S)-2-[(Azepane-1-carbonyl)-amino]-4-methyl-pentanoic acid (0.56 g, 2.2 mmol) was dissolved in dry DMF (7 mL) under nitrogen atmosphere and cooled to 0° C. in an ice-water bath. To this solution were added, in succession, N,N-diisopropylethylamine (0.76 mL, 4.4 mmol) and solid O-benzotriazol-1-yl-N,N,N',N'-tetramethyluronium hexafluorophosphate (0.82 g, 2.2 mmol). The resulting reaction mixture was stirred at that temperature for 30 minutes; solid 1-bis(4-fluorophenyl)methyl piperazine (0.63 g, 2.2 mmol, Acros Organics, Pittsburgh, Pa.) was then added. After sequentially 30 minutes stirring at 0° C. and 2 hours at ambient temperature, reaction mixture was mixed with 60 mL of diethyl ether; the resulting mixture was successively washed with saturated aqueous NaHCO$_3$ solution (2×60 mL), brine (2×60 mL), and was dried over Na$_2$SO$_4$. The solution was concentrated in vacuo affording a viscous oil. The crude product was further purified by flash chromatography (60% EtOAc in hexane) to provide 1.1 g (96%) of the pure titled compound as a white foam: mp 78–86° C. APCI-MS m/z 527.0 (MH$^+$).

EXAMPLE 32

Preparation of (S)-Azepane-1-carboxylic acid (2-{4-[bis-(4-fluoro-phenyl)-methyl]-piperazin-1-yl}-2-oxo-ethyl)-amide

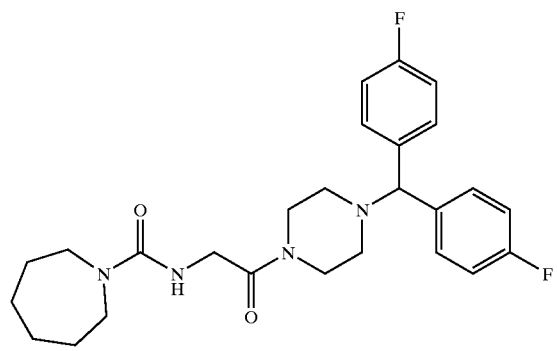

Step A. 2-[(Azepane-1-carbonyl)-amino]-acetic acid benzyl ester

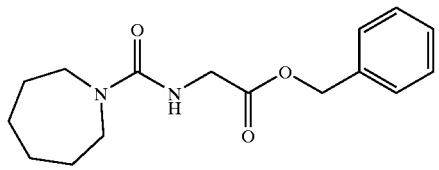

In a manner similar to that described in Example 2, Step A, glycine benzyl ester (15.0 g, 74.4 mmol) was converted to the title compound (16.7 g, 77%). APCI-MS m/z 241 (MH$^+$).

Step B. 2-[(Azepane-1-carbonyl)-amino]-acetic acid

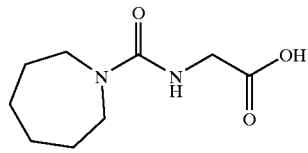

In a manner similar to that described in Example 1, Step B, 2-[(azepane-1-carbonyl)-amino]-acetic acid benzyl ester (2.07 g, 7.1 mmol) was converted to the title compound (0.50 g, 70%). APCI-MS m/z 201 (MH$^+$).

Step C

[(Azepane-1-carbonyl)-amino]-acetic acid (0.22 g, 1.1 mmol) was dissolved in dry DMF (5 mL) under nitrogen atmosphere and cooled to 0° C. in an ice-water bath. To this solution were added, in succession, N,N-diisopropylethylamine (0.38 mL, 2.2 mmol) and solid O-benzotriazol-1-yl-N,N,N',N'-tetramethyluronium hexafluorophosphate (0.41 g, 1.1 mmol). The resulting reaction mixture was stirred at that temperature for 30 minutes; solid 1-bis(4-fluorophenyl)methyl piperazine (0.31 g, 1.1 mmol) was then added. After additional 90 minutes stirring at 0° C., reaction mixture was mixed with 60 mL of diethyl ether; the resulting mixture was successively washed with saturated aqueous NaHCO$_3$ solution (2×50 mL), brine (2×50 mL), and dried over Na$_2$SO$_4$. The solution was concentrated in vacuo affording a viscous oil. The crude product was further purified by flash chromatography (straight EtOAc) to provide 0.29 g (61%) of the pure titled compound as a white foam; mp 66–86° C. APCI-MS m/z 471.2 (MH$^+$).

EXAMPLE 33

Preparation of (S)-Azepane-1-carboxylic acid (1-{4-[bis-(4-fluoro-phenyl)-methyl]-piperazine-1-carbonyl}-2-methyl-propyl)-amide

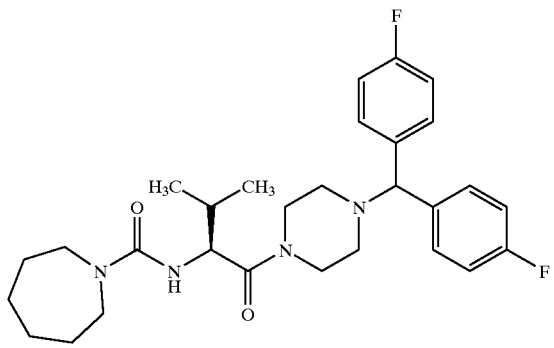

(S)-2-[(Azepane-1-carbonyl)-amino]-3-methyl-butyric acid (0.26 g, 1.1 mmol, Example 26, Step B) was dissolved in dry DMF (5 mL) under nitrogen atmosphere and cooled to 0° C. in an ice-water bath. To this solution were added, in succession, N,N-diisopropylethylamine (0.37 mL, 2.1 mmol) and solid O-benzotriazol-1-yl-N,N,N',N'-tetramethyluronium hexafluorophosphate (0.40 g, 1.1 mmol). The resulting reaction mixture was stirred at that temperature for 30 minutes; solid 1-bis(4-fluorophenyl) methyl piperazine (0.31 g, 1.1 mmol) was then added. After additional 90 minutes stirring at 0° C., reaction mixture was mixed with 60 mL of diethyl ether; the resulting mixture was successively washed with saturated aqueous NaHCO$_3$ solution (2×50 mL), brine (2×50 mL), and dried over Na$_2$SO$_4$. The solution was concentrated in vacuo affording a viscous oil. The crude product was further purified by flash chromatography (60% EtOAc in hexane) to provide 0.45 g (82%) of the pure titled compound as a white foam; mp 72–82° C. APCI-MS m/z 513.2 (MH$^+$).

EXAMPLE 34

Preparation of (R)-Azepane-1-carboxylic acid {1-(4-[bis-(4-fluoro-phenyl)-methyl]-piperazine-1-carbonyl}-3-methyl-butyl)-amide

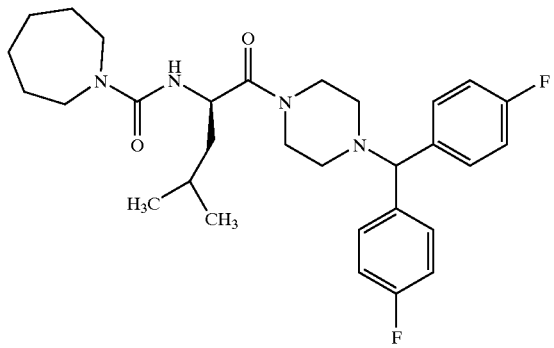

(R)-2-[{Azepane-1-carbonyl)-amino]}-4-methyl-pentanoic acid (0.33 g, 1.3 mmol, Example 2, Step B) was dissolved in dry DMF (5 mL) under nitrogen atmosphere and cooled to 0° C. in an ice-water bath. To this solution were added, in succession, N,N-diisopropylethylamine (0.45 mL, 2.6 mmol) and solid O-benzotriazol-1-yl-N,N,N',N'-tetramethyluronium hexafluorophosphate (0.49 g, 1.3 mmol). The resulting reaction mixture was stirred at that temperature for 30 minutes; solid 1-bis(4-fluorophenyl) methyl piperazine (0.37 g, 1.3 mmol) was then added. After additional 90 minutes stirring at 0° C., reaction mixture was mixed with 60 mL of diethyl ether; the resulting mixture was successively washed with saturated aqueous NaHCO$_3$ solution (2×50 mL), brine (2×50 mL), and dried over Na$_2$SO$_4$. The solution was concentrated in vacuo affording a viscous oil. The crude product was further purified by flash chromatography (60% EtOAc in hexane) to provide 0.58 g (86%) of the pure titled compound as a white foam: mp 71–84° C. APCI-MS m/z 527.3 (MH$^+$).

EXAMPLE 35

Preparation of (S)-(1-{4-[Bis-(4-fluoro-phenyl)-methyl]-piperazin-1-ylmethyl}-3-methyl-butyl)-carbamic acid tert-butyl ester

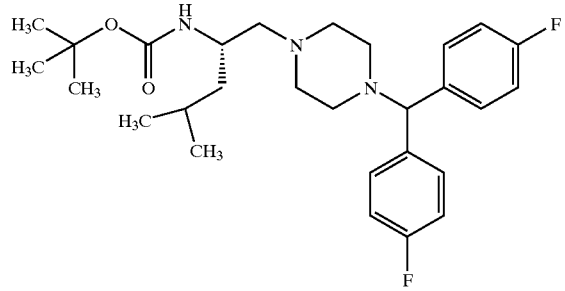

Step A. (S)-(1-Methoxycarbamoyl-3-methyl-butyl)-carbamic acid tert-butyl ester

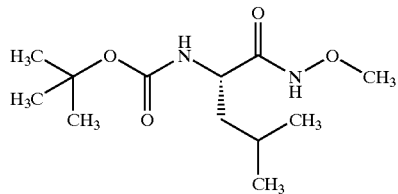

N-tert-Butoxycarbonyl-L-leucine monohydrate (2.5 g, 10 mmol, Bachem Inc., Torrance, Calif.) was dissolved in dry DMF (15 mL) under nitrogen atmosphere and cooled to 5° C. To this solution were added, in succession, N,N-diisopropylethylamine (5.3 mL, 30 mmol) and solid O-benzotriazol-1-yl-N,N,N',N'-tetramethyluronium hexafluorophosphate (3.8 g, 10 mmol). The resulting reaction mixture was stirred at that temperature for 30 minutes; O,N-dimethylhydroxylamine hydrochloride (1.1 g, 11 mmol, Aldrich, Milwaukee, Wis.) was then added. After additional 30 minutes stirring at 0° C., the reaction mixture was mixed with 75 mL of diethyl ether; the resulting mixture was successively washed with 5% aqueous HCl solution (50 mL), brine (50 mL), saturated aqueous NaHCO$_3$ solution (50 mL), brine (2×50 mL), and was dried over Na$_2$SO$_4$. The solution was concentrated in vacuo affording 2.3 g of desired product as a clear oil which was used in the subsequent reaction without further purification.

Step B. (S)-(1-Formyl-3-methyl-butyl)-carbamic acid tert-butyl ester

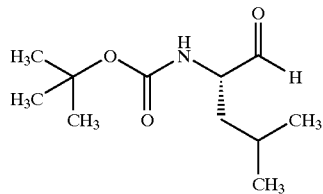

(S)-(1-Methoxycarbamoyl-3-methyl-butyl)-carbamic acid tert-butyl ester (2.2 g, 8.0 mmol) was dissolved in dry ether (80 mL) under nitrogen atmosphere and cooled to −3° C. in a ice-water-NaCl bath. Solid lithium aluminum hydride (0.31 mg, 8.2 mmol, Aldrich, Milwaukee, Wis.) was then added; the resulting reaction mixture was stirred at that temperature for 25 minutes at which time TLC showed no starting material left, then the reaction was quenched by addition of an aqueous NaHSO$_4$ solution (1.9 g NaHSO$_4$ in 60 mL of water). Two layers were separated; and aqueous layer was extracted with ether (4×100 mL). The combined ether solution was washed successively with 3N aqueous HCl solution (3×100 mL), brine (100 mL), saturated aqueous NaHCO$_3$ solution (3×100 mL), brine (3×100 mL), and was dried over MgSO$_4$. The solution was concentrated in vacuo affording 1.6 g of desired product as a clear oil which was used in the subsequent reaction without further purification.

Step C (S)-(1-Formyl-3-methyl-butyl)-carbamic acid tert-butyl ester (0.39 mg, 1.8 mmol) and 1-bis(4-fluorophenyl)methyl piperazine (0.50 g, 1.7 mmol) were dissolved in 1% HOAc in methanol (8 mL) under nitrogen atmosphere at ambient temperature. After stirring at that temperature for 1 hour, a solution of sodium cyanoborohydride (250 mg, 3.6 mmol) in methanol was added. The resulting reaction mixture was stirred at ambient temperature for 24 hours at which time TLC showed no starting aldehyde. 3N aqueous HCl was added in 5 mL portions until bubbling subsided; pH was adjusted to 8 with saturated aqueous NaHCO$_3$ solution. The resulting mixture was extracted with EtOAc (3×25 mL), the combined organic solution was washed with brine (50 mL) and dried over MgSO$_4$. The solution was concentrated in vacuo affording an amber oil. The crude product was further purified by flash chromatography (20%–30% EtOAc in hexanes) affording 342 mg (41%) of the pure titled compound as a clear oil. APCI-MS m/z 488.3 (MH$^+$).

Anal. C$_{28}$H$_{39}$N$_3$O$_2$F$_2$.0.5H$_2$O: C, 67.72; H, 8.12; N, 8.46. Found: C, 68.02; H, 7.97; N, 8.59.

EXAMPLE 36

Preparation of (S)-Azepane-1-carboxylic acid (1-{4-[bis-(4-fluoro-phenyl)-methyl]-piperazin-1-ylmethyl}-3-methyl-butyl)-amide

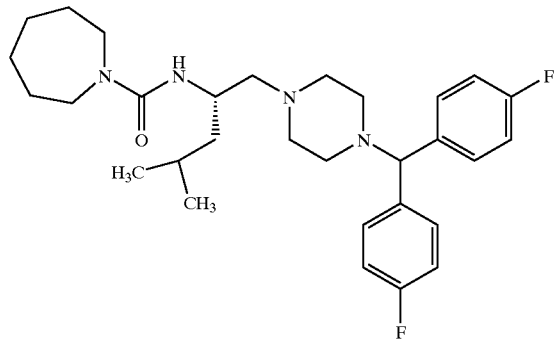

Step A. (S)-1-{4-[Bis-(4-fluoro-phenyl)-methyl]-piperazin-1-ylmethyl}-3-methyl-butylamine monohydrochloride

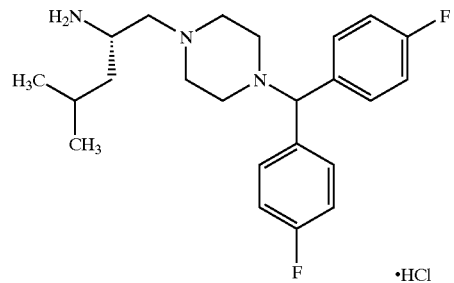

(S)-(1-{4-[Bis-(4-fluoro-phenyl)-methyl]-piperazin-1-ylmethyl}-3-methyl-butyl)carbamic acid tert-butyl ester (0.225 g, 0.461 mmol, Example 35) was dissolved in CH$_2$Cl$_2$ (4 mL) under nitrogen at ambient temperature. To this solution was added trifluoroacetic acid (0.5 mL). The resulting reaction mixture was stirred for 3 hours, then concentrated in vacuo. The viscous pale-amber oil obtained was dissolved in 5 mL of ether and treated with 3.3 mL of saturated ethereal HCl. The resulting white precipitate was triturated with 3:1 EtOAc/2,2,4-trimethylpentane, and collected via filtration. The filtrate was concentrated in vacuo affording a viscous amber oil (189 mg) which was used in the subsequent reaction without further purification.

Step B. Azepane-1-carbonyl chloride

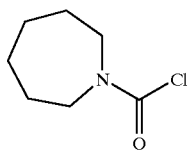

Made according to the procedure reported in *Tetrahedron Lett.*, 1994;35:839.

Step C

To a solution of (S)-1-{4-[bis-(4-fluoro-phenyl)-methyl]-piperazin-1-ylmethyl}-3-methyl-butylamine monohydrochloride (189 mg, 0.46 mmol) in benzene (2 mL) were added sequentially N,N-diisopropylethylamine (0.26 mL, 1.5 mmol), 4-dimethylaminopyridine (20 mg), and azepane-1-carbonyl chloride (0.13 mL, 0.78 mmol) under nitrogen atmosphere. The resulting reaction mixture was refluxed for 16 hours, then cooled to ambient temperature. The reaction mixture was filtered to remove the white solid formed during the reaction; the filtrate was concentrated in vacuo. The residue was dissolved in EtOAc (25 mL) and washed successively with saturated aqueous NaHCO₃ solution (25 mL), brine (2×25 mL), and dried over Na₂SO₄. The solution was concentrated in vacuo affording a slightly amber colored oil. The crude product was purified first by flash chromatography (50% EtOAc in hexanes), then by preparative plate (50% EtOAc in hexanes) affording 46.6 mg (20%) of the pure titled compound as a clear oil. APCI-MS m/z 513.3 (MH⁺).

Anal. $C_{30}H_{42}N_4OF_2 \cdot 0.5HCl \cdot 0.25EtOAc$: C, 69.40; H, 8.28; N, 10.44; Cl, 0.33. Found: C, 69.10; H, 8.06; N, 10.43; Cl, 0.21.

EXAMPLE 37

Preparation of (S)-1-{4-[Bis-(4-fluoro-phenyl)-methyl]-piperazin-1-yl}-4-methyl-2-piperidin-1-yl-pentan-1-one

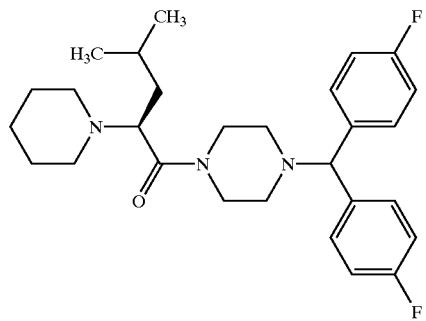

To a suspension of (S)-4-methyl-2-piperidin-1-yl-pentanoic acid monohydrobromide (0.28 g, 1.0 mmol, Example 22, Step A) and N,N-diisopropylethylamine (0.52 mL, 3.0 mmol) in dry DMF (6 mL) was added solid O-benzotriazol-1-yl -N,N,N',N'-tetramethyluronium hexafluorophosphate (0.39 g, 0.99 mmol) under nitrogen atmosphere at 0° C. The resulting reaction mixture, which became a clear solution after addition of O-benzotriazol-1-yl-N,N,N',N'-tetramethyluronium hexafluorophosphate, was stirred at that temperature for 20 minutes; solid 1-bis(4-fluorophenyl)methyl piperazine (0.29 g, 1.0 mmol) was then added. After additional 3 hours stirring while the reaction mixture was allowed to slowly warm up to ambient temperature, reaction mixture was mixed with 100 mL of diethyl ether; the resulting mixture was successively washed with saturated aqueous NaHCO₃ solution (2×100 mL), brine (2×100 mL), and dried over MgSO₄. The solution was concentrated in vacuo affording an amber oil. The crude product was further purified by flash chromatography (20:80:1 EtOAc:hexane:MeOH) to provide 0.37 g (79%) of the pure titled compound as a white foam. APCI-MS m/z 470.3 (MH⁺).

Anal. $C_{28}H_{37}N_3OF_2$: C, 71.61; H, 7.94; N, 8.95. Found: C, 71.44; H, 7.86; N, 8.84.

EXAMPLE 38

Preparation of (S)-1-{4-[Bis-(4-fluoro-phenyl)-methyl]-piperazin-1-yl}-2-cyclohexylamino-4-methyl-pentan-1-one

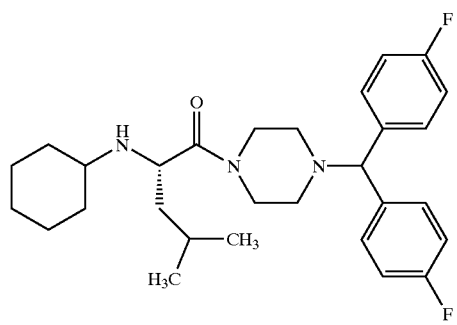

A suspension of (S)-2-cyclohexylamino-4-methyl-pentanoic acid (0.556 g, 2.62 mmol) and 1-bis(4-fluorophenyl)methyl piperazine (0.378 g, 1.31 mmol) in dry DMF (7 mL) was treated with Triton® B (2.40 mL, 5.28 mmol, 40 weight percent solution in methanol), a clear solution was obtained. The resulting reaction solution was cooled to 0° C. in an ice-water bath. To this solution was added solid O-benzotriazol-1-yl-N,N,N',N'-tetramethyluronium hexafluorophosphate (0.993 g, 2.62 mmol). After stirring at 0° C. for 30 minutes, the cooling bath was removed, and the stirring was continued at ambient temperature for 30 minutes. After this period, the reaction mixture was mixed with 60 mL of diethyl ether and 60 mL of saturated aqueous NaHCO₃ solution. White solid which forms was removed by filtration. The two layers of the filtrate were separated; the organic layer was successively washed with saturated aqueous NaHCO₃ solution (50 mL), brine (2×50 mL), and was dried over Na₂SO₄. The solution was concentrated in vacuo affording a viscous oil. The crude product was purified by flash chromatography (30% EtOAc in hexanes) affording 0.48 g (76%) of the pure titled compound as a white foam: mp 45–54° C. APCI-MS m/z 484.4 (MH⁺).

EXAMPLE 39

Preparation of (S)-1-{4-[Bis-(4-fluoro-phenyl)-methyl]-piperazin-1-yl}-2-dimethylamino-4-methyl-pentan-1-one dihydrochloride

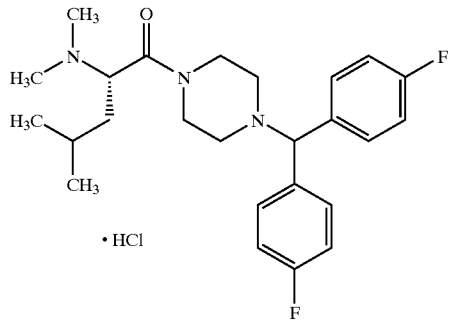

(S)-2-Dimethylamino-4-methyl-pentanoic acid (0.200 g, 1.26 mmol, Example 20, Step A) was dissolved in dry DMF (4 mL) under nitrogen atmosphere and cooled to 0° C. in an ice-water bath. To this solution were added, in succession, N,N-diisopropylethylamine (0.438 mL, 2.51 mmol) and solid O-benzotriazol-1-yl-N,N,N',N'-tetramethyluronium hexafluorophosphate (0.476 g, 1.26 mmol). The resulting reaction mixture was stirred at that temperature for 30 minutes; solid 1-bis(4-fluorophenyl)methyl piperazine (0.362 g, 1.26 mmol) was then added. After sequentially 15 minutes stirring at 0° C. and 20 minutes at ambient temperature, reaction mixture was mixed with 150 mL of diethyl ether; the resulting mixture was successively washed with saturated aqueous NaHCO₃ solution (2×60 mL), brine (2×60 mL), and was dried over Na₂SO₄. The solution was concentrated in vacuo affording a viscous oil. The crude product was further purified by flash chromatography (5% methanol in chloroform). The free amine was dissolved in 5 mL of ethyl ether and treated with ethereal HCl to provide 0.43 g (68%) of the pure titled compound as a white solid; mp 220–205° C. APCI-MS m/z 430.3 (MH$^+$).

EXAMPLE 40

Preparation of (S)-1-{4-[Bis-(4-fluoro-phenyl)-methyl]-piperazin-1-yl}-2-(cyclohexyl-methyl-amino)-4-methyl-pentan-1-one

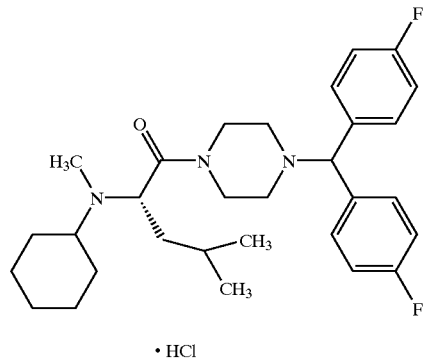

(S)-2-(Cyclohexyl-methyl-amino)-4-methyl-pentanoic acid (0.200 g, 0.880 mmol, Example 21, Step A) was dissolved in dry DMF (4 mL) under nitrogen atmosphere and cooled to 0° C. in an ice-water bath. To this solution were added, in succession, N,N-diisopropylethylamine (0.389 mL, 1.76 mmol) and solid O-benzotriazol-1-yl-N,N,N',N'-tetramethyluronium hexafluorophosphate (0.334 g, 0.880 mmol). The resulting reaction mixture was stirred at that temperature for 30 minutes; solid 1-bis(4-fluorophenyl)methyl piperazine (0.254 g, 0.880 mmol) was then added. After stirring for, sequentially, 10 minutes at 0° C. and 90 minutes at ambient temperature, reaction mixture was mixed with 50 mL of diethyl ether; the resulting mixture was successively washed with saturated aqueous NaHCO₃ solution (2×60 mL), brine (2×60 mL), and was dried over Na₂SO₄. The solution was concentrated in vacuo affording a viscous oil. The crude product was further purified by flash chromatography (30% EtOAC in hexanes). The free amine was dissolved in 5 mL of ethyl ether and treated with ethereal HCl. Subsequent concentration in vacuo and drying under vacuum provided 0.39 g (78%) of the pure titled compound as a white solid; mp 171–182° C. APCI-MS m/z 498.3 (MH$^+$).

EXAMPLE 41

Preparation of (S)-1-{4-[Bis-(4-fluoro-phenyl)-methyl]-piperazin-1-yl}-4-methyl-2-[methyl-(tetrahydro-pyran-4-yl)-amino]-pentan-1-one

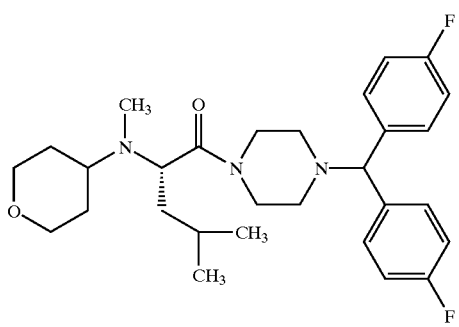

(S)-4-Methyl-2-[methyl-(tetrahydro-pyran-4-yl)-amino]-pentanoic acid (0.200 g, 0.873 mmol, Example 27, Step A) was dissolved in dry DMF (4 mL) under nitrogen atmosphere and cooled to 0° C. in an ice-water bath. To this solution were added, in succession, N,N,-diisopropylethylamine (0.304 mL, 1.75 mmol) and solid O-benzotriazol-1-yl-N,N,N',N'-tetramethyluronium hexafluorophosphate (0.331 g, 0.873 mmol). The resulting reaction mixture was stirred at that temperature for 30 minutes; solid 1-bis(4-fluorophenyl)methyl piperazine (0.252 g, 0.873 mmol) was then added. After stirring for, sequentially, 15 minutes at 0° C. and 40 minutes at ambient temperature, reaction mixture was mixed with 50 mL of diethyl ether; the resulting mixture was successively washed with saturated aqueous NaHCO₃ solution (2×60 mL), brine (2×60 mL), and was dried over Na₂SO₄. The solution was concentrated in vacuo affording a viscous oil. The crude product was further purified by flash chromatography (50% EtOAc in hexane) to provide 0.326 g (75%) of the pure titled compound as a white foam: mp 56–65° C. APCI-MS m/z 500.3 (MH$^+$).

EXAMPLE 42

Preparation of (S)-1-{4-[Bis-(4-fluoro-phenyl)-methyl]-piperazin-1-yl}-4-methyl-2-morpholin-4-yl-pentan-1-one

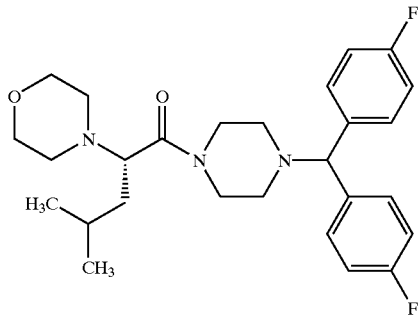

4-Methyl-2-morpholin-4-yl-pentanoic acid (0.200 g, 0.994 mmol, Example 23, Step A) was dissolved in dry DMF (4 mL) under nitrogen atmosphere and cooled to 0° C. in an ice-water bath. To this solution were added, in succession, N,N-diisopropylethylamine (0.346 mL, 1.99 mmol) and solid O-benzotriazol-1-yl-N,N,N',N'-tetramethyluronium hexafluorophosphate (0.379 g, 0.994 mmol). The resulting reaction mixture was stirred at that temperature for 30 minutes; solid 1-bis(4-fluorophenyl)methyl piperazine (0.287 g, 0.994 mmol) was then added. After stirring for, sequentially, 10 minutes at 0° C. and 20 minutes at ambient temperature, reaction mixture was mixed with 50 mL of diethyl ether; the resulting mixture was successively washed with saturated aqueous $NaHCO_3$ solution (2×60 mL), brine (2×60 mL), and was dried over $Na_2SO_4$. The solution was concentrated in vacuo affording a viscous oil. The crude product was further purified by flash chromatography (40% EtOAc in hexane) to provide 0.284 g (60%) of the pure titled compound as a white foam; mp 55–63° C. APCI-MS m/z 472.3.0 (MH$^+$).

EXAMPLE 43

Preparation of (S)-Azepane-1-carboxylic acid (1-{4-[bis-(4-fluoro-phenyl)-methyl]-piperazine-1-carbonyl}-2-methyl-butyl)-amide

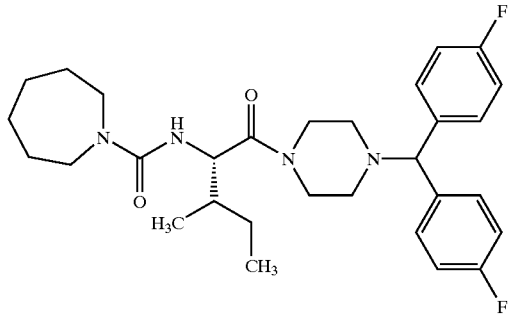

(S)-2-[(Azepane-1-carbonyl)-amino]-3-methyl-pentanoic acid (0.300 g, 1.17 mmol, Example 16, Step B) was dissolved in dry DMF (4 mL) under nitrogen atmosphere and cooled to 0° C. in an ice-water bath. To this solution were added, in succession, N,N,-diisopropylethylamine (0.408 mL, 2.34 mmol) and solid O-benzotriazol-1-yl-N,N,N',N'-tetramethyluronium hexafluorophosphate (0.444 g, 1.17 mmol). The resulting reaction mixture was stirred at that temperature for 35 minutes; solid 1-bis(4-fluorophenyl)methyl piperazine (0.337 g, 1.17 mmol) was then added. After stirring for, sequentially, 10 minutes at 0° C. and 30 minutes at ambient temperature, reaction mixture was mixed with 60 mL of diethyl ether; the resulting mixture was successively washed with saturated aqueous $NaHCO_3$ solution (2×60 mL), brine (2×60 mL), and was dried over $Na_2SO_4$. The solution was concentrated in vacuo affording a viscous oil. The crude product was further purified by flash chromatography (40% EtOAc in hexane, then 60% EtOAc in hexane) to provide 0.536 g (87%) of the pure titled compound as a white foam: mp 64–77° C. APCI-MS m/z 527.4 (MH$^+$).

EXAMPLE 44

Preparation of (S)-4-Phenyl-piperazine-1-carboxylic acid (1-{4-[bis-(4-fluoro-phenyl)-methyl]-piperazine-1-carbonyl}-3-methyl-butyl)-amide

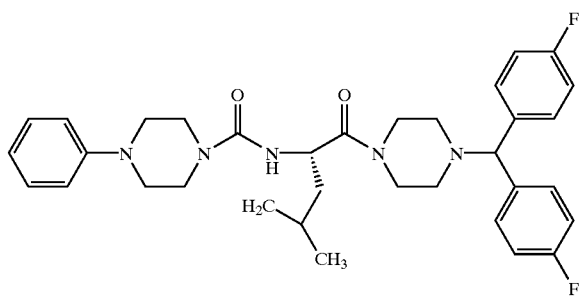

(S)-4-Methyl-2-[(4-phenyl-piperazine-1-carbonyl)-amino]pentanoic acid (0.300 g, 0.939 mmol, Example 17, Step B) was dissolved in dry DMF (4 mL) under nitrogen atmosphere and cooled to 0° C. in an ice-water bath. To this solution were added, in succession, N,N-diisopropylethylamine (0.327 mL, 1.88 mmol) and solid O-benzotriazol-1-yl-N,N,N',N'-tetramethyluronium hexafluorophosphate (0.356 g, 0.939 mmol). The resulting reaction mixture was stirred at that temperature for 35 minutes; solid 1-bis(4-fluorophenyl)methyl piperazine (0.271 g, 0.939 mmol) was then added. After stirring for, sequentially, 10 minutes at 0° C. and 40 minutes at ambient temperature, reaction mixture was mixed with 60 mL of diethyl ether; the resulting mixture was successively washed with saturated aqueous $NaHCO_3$ solution (2×60 mL), brine (2×60 mL), and was dried over $Na_2SO_4$. The solution was concentrated in vacuo affording a viscous oil. The crude product was further purified by flash chromatography (40% EtOAc in hexane, then 60% EtOAc in hexane) to provide 0.42 g (76%) of the pure titled compound as a light yellow foam: mp 83–91 ° C. APCI-MS m/z 590.4 (MH$^+$).

EXAMPLE 45

Preparation of (S)-Azepane-1-carboxylic acid {1-[4-(9H-fluoren-9-yl)-piperazine-1-carbonyl]-3-methyl-butyl}-amide

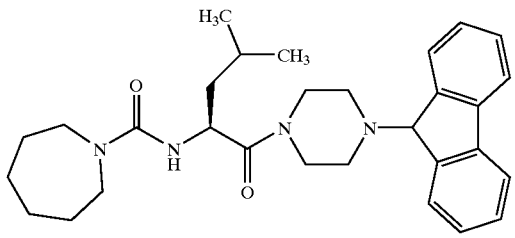

(S)-2-[(Azepane-1-carbonyl)-amino]4-methyl-pentanoic acid (0.300 g, 1.17 mmol, Example 1, Step B) was dissolved in dry DMF (4 mL) under nitrogen atmosphere and cooled to 0° C. in an ice-water bath. To this solution were added, in succession, N,N-diisopropylethylamine (0.816 mL, 4.68 mmol) and solid O-benzotriazol-1-yl-N,N,N',N'-tetramethyluronium hexafluorophosphate (0.444 g, 1.17 mmol). The resulting reaction mixture was stirred at that temperature for 30 minutes; solid 9-piperazinofluorene dihydrochloride (0.293 g, 1.17 mmol, Maybridge Chemical Co. Ltd., Tintagel Cornwall, U.K.) was then added. After stirring for, sequentially, 20 minutes at 0° C. and 20 minutes at ambient temperature, reaction mixture was mixed with 60 mL of diethyl ether; the resulting mixture was successively washed with saturated aqueous $NaHCO_3$ solution (2×60 mL), brine (2×60 mL), and was dried over $Na_2SO_4$. The solution was concentrated in vacuo affording a viscous oil. The crude product was further purified by flash chromatography (50% EtOAc in hexane containing 1% MeOH to provide 0.21 g (37%) of the pure titled compound as a white foam: mp 63–73° C. APCI-MS m/z 489.3 (MH$^+$).

EXAMPLE 46

Preparation of 1-{4-[Bis-(4-fluoro-phenyl)-methyl]-piperazin-1-yl}-4-methyl-2-[methyl-(3-methyl-butyl)-amino]-pentan-1-one dihydrochloride

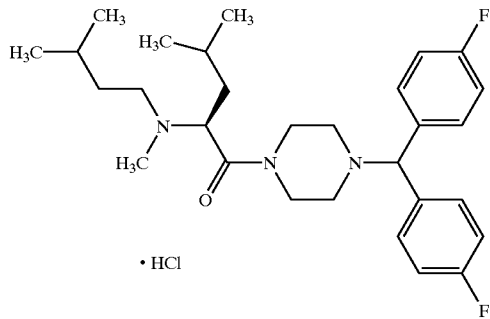

4-Methyl-2-[methyl-(3-methyl-butyl)-amino]-pentanoic acid (0.300 g, 1.39 mmol, Example 28, Step B) was dissolved in dry DMF (4 mL) under nitrogen atmosphere and cooled to 0° C. in an ice-water bath. To this solution were added, in succession, N,N-diisopropylethylamine (0.485 mL, 2.79 mmol) and solid O-benzotriazol-1-yl-N,N,N',N'-tetramethyluronium hexafluorophosphate (0.528 g, 1.39 mmol). The resulting reaction mixture was stirred at that temperature for 25 minutes; solid 1-bis(4-fluorophenyl) methyl piperazine (0.402 g, 1.39 mmol) was then added. After stirring for, sequentially, 20 minutes at 0° C. and 40 minutes at ambient temperature, reaction mixture was mixed with 60 mL of diethyl ether; the resulting mixture was successively washed with saturated aqueous $NaHCO_3$ solution (2×60 mL), brine (2×60 mL), and was dried over $Na_2SO_4$. The solution was concentrated in vacuo affording a viscous oil. The crude product was further purified by flash chromatography (30% EtOAc in hexane). The free amine was dissolved in 5 mL of ethyl ether and treated with ethereal HCl, subsequent concentration in vacuo and drying under vacuum provided 0.63 g (78%) of the pure titled compound as a white solid: mp 173–186° C. APCI-MS m/z 486.4 (MH$^+$).

EXAMPLE 47

Preparation of (S)-4-Methyl-piperazine-1-carboxylic acid (1-{4-[bis-(4-fluoro-phenyl)-methyl]-piperazine-1-carbonyl}-3-methyl-butyl)-amide

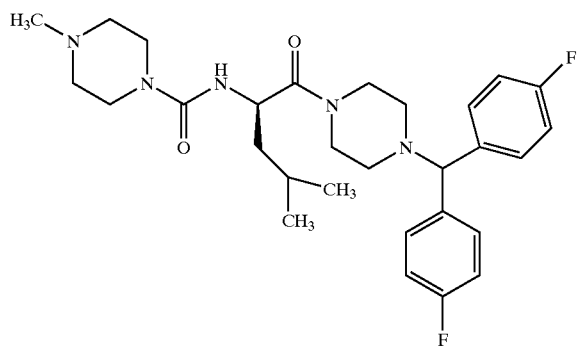

(S)-2-[(4-Methyl-piperazine-1-carbonyl)-amino]-4-methyl pentanoic acid (0.300 g, 1.23 mmol, Example 29, Step B) was dissolved in dry DMF (4 mL) under nitrogen atmosphere and cooled to 0° C. in an ice-water bath. To this solution were added, in succession, N,N-diisopropylethylamine (0.129 mL, 2.47 mmol) and solid O-benzotriazol-1-yl-N,N,N',N'-tetramethyluronium hexafluorophosphate (0.468 g, 1.23 mmol). The resulting reaction mixture was stirred at that temperature for 30 minutes; solid 1-bis(4-fluorophenyl)methyl piperazine (0.356 g, 1.23 mmol) was then added. After stirring for, sequentially, 10 minutes at 0° C. and 20 minutes at ambient temperature, reaction mixture was mixed with 60 mL of diethyl ether; the resulting mixture was successively washed with saturated aqueous $NaHCO_3$ solution (2×60 mL), brine (2×60 mL), and was dried over $Na_2SO_4$. The solution was concentrated in vacuo affording a viscous oil. The crude product was further purified by flash chromatography (20% MeOH in EtOAc) to provide 0.53 g (78%) of the pure titled compound as a white foam: mp 65–78° C. APCI-MS m/z 528.4 (MH$^+$).

EXAMPLE 48

Preparation of (S)-Azepane-1-carboxylic acid [1-(4-benzhydryl-piperazine-1-carbonyl)-3-methyl-butyl]-amide

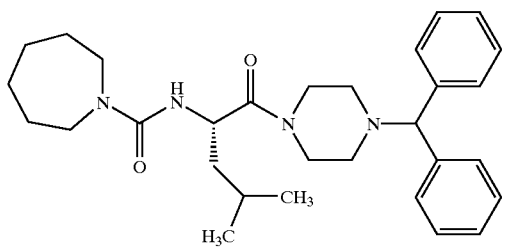

(S)-2-[(Azepane-1-carbonyl)-amino]-4-methyl-pentanoic acid (0.300 g, 1.17 mmol, Example 1, Step B) was dissolved in dry DMF (4 mL) under nitrogen atmosphere and cooled to 0° C. in an ice-water bath. To this solution were added, in succession, N,N-diisopropylethylamine (0.408 mL, 2.34 mmol) and solid O-benzotriazol-1-yl-N,N,N',N'-tetramethyluronium hexafluorophosphate (0.444 g, 1.17 mmol). The resulting reaction mixture was stirred at that temperature for 35 minutes; solid benzhydrylpiperazine (0.295 g, 1.17 mmol) was then added. After stirring for, sequentially, 10 minutes at 0° C. and 40 minutes at ambient temperature, reaction mixture was mixed with 60 mL of diethyl ether; the resulting mixture was successively washed with saturated aqueous $NaHCO_3$ solution (2×60 mL), brine (2×60 mL), and was dried over $Na_2SO_4$. The solution was concentrated in vacuo affording a viscous oil. The crude product was further purified by flash chromatography (50% EtOAc in hexanes) to provide 0.49 g (85%) of the pure titled compound as a white foam; mp 66–74° C. APCI-MS m/z 491.4 (MH$^+$).

EXAMPLE 49

Preparation of (S)-1-{4-[Bis-(4-fluoro-phenyl)-methyl]-piperazin-1-yl}-2-isopropylamino-4-methyl-pentan-1-one monohydrochloride

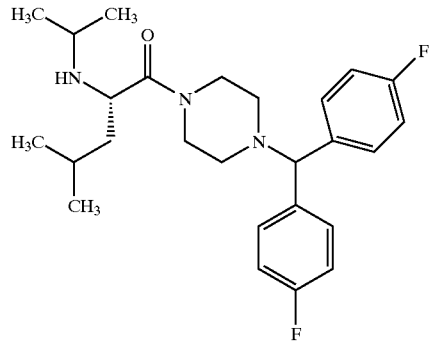

A suspension of (S)-2-isopropylamino-4-methyl-pentanoic acid (0.433 g, 2.50 mmol, Example 19, Step A) and 1-bis(4-fluorophenyl)methyl piperazine (0.743 g, 2.58 mmol) in dry DMF (12 mL) was treated with Triton® B (2.27 mL, 4.99 mmol, 40 wt. % solution in methanol), a clear solution was obtained. The resulting reaction solution was cooled to 0° C. in an ice-water bath. To this solution was added solid O-benzotriazol-1-yl-N,N,',N'-tetramethyluronium hexafluorophosphate (0.950 g, 2.50 mmol). After stirring at 0° C. for 90 minutes, the cooling bath was removed, and the stirring was continued at ambient temperature for 30 minutes. After this period, the reaction mixture was mixed with 100 mL of diethyl ether and successively washed with saturated aqueous $NaHCO_3$ solution (100 mL), brine (2×100 mL), and was dried over $Na_2SO_4$. The solution was concentrated in vacuo affording a viscous oil. The crude product was purified by flash chromatography (EtOAc:Hexanes:MeOH 50:50:5). The free amine was dissolved in 5 mL of ethyl ether and treated with ethereal HCl, subsequent filtration and drying under vacuum provided 0.78 g (65%) of the pure titled compound as a white solid: mp 100–103° C. APCI-MS m/z 444.4 (MH$^+$).

EXAMPLE 50

Preparation of (S)-(1-{4-[Bis-(4-fluoro-phenyl)-methyl]-piperazine-1-carbonyl}-3-methyl-butyl)-carbamic acid tert-butyl ester

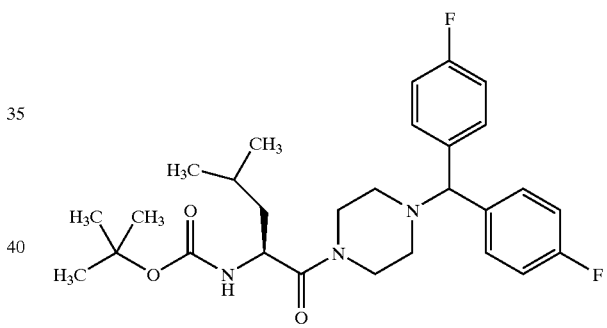

N-tert-Butoxycarbonyl-L-leucine monohydrate (4.32 g, 17.3 mmol, Bachem Inc., Torrance, Calif.) was dissolved in dry DMF (33 mL) under nitrogen atmosphere and cooled to 0° C. in an ice-water bath. To this solution were added, in succession, N,N-diisopropylethylamine (6.04 mL, 34.7 mmol) and solid -benzotriazol-1-yl-N,N,N',N'-tetramethyluronium hexafluorophosphate (6.58 g, 17.4 mmol). The resulting reaction mixture was stirred at that temperature for 35 minutes; solid 1-bis(4-fluorophenyl)methyl piperazine (5.00 g, 17.3 mmol) was then added. After stirring for, sequentially, 15 minutes at 0° C. and 30 minutes at ambient temperature, reaction mixture was mixed with 120 mL of diethyl ether; the resulting mixture was successively washed with saturated aqueous $NaHCO_3$ solution (2×120 mL), brine (2×120 mL), and was dried over $Na_2SO_4$. The solution was concentrated in vacuo affording a viscous oil. The crude product was further purified by flash chromatography (30% EtOAc in hexanes) to provide 8.23 g (94%) of the pure titled compound as a off-white foam: mp 59–66° C. APCI-MS m/z 502.4 (MH$^+$).

EXAMPLE 51

Preparation of (S)-(1-Benzyl-2-{4-[bis-(4-fluoro-phenyl)-methyl]-piperazin-1-yl}-2-oxo-ethyl)-carbamic acid tert-butyl ester

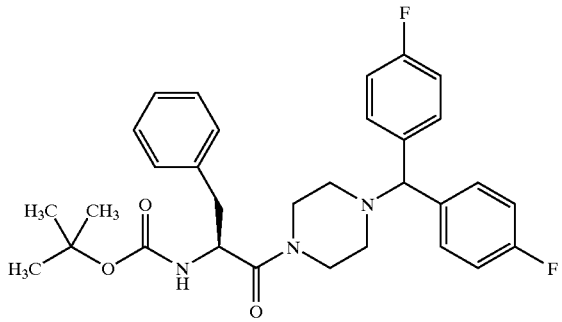

N-tert-Butoxycarbonyl-L-phenylalanine (4.60 g, 17.3 mmol, Bachem Inc., Torrance, Calif.) was dissolved in dry DMF (33 mL) under nitrogen atmosphere and cooled to 0° C. in an ice-water bath. To this solution were added, in succession, N,N-diisopropylethylamine (6.04 mL, 34.7 mmol) and solid O-benzotriazol-1-yl-N,N,N',N'-tetramethyluronium hexafluorophosphate (6.58 g, 17.4 mmol). The resulting reaction mixture was stirred at that temperature for 35 minutes; solid 1-bis(4-fluorophenyl) methyl piperazine (5.00 g, 17.3 mmol) was then added. After stirring for, sequentially, 15 minutes at 0° C. and 30 minutes at ambient temperature, reaction mixture was mixed with 120 mL of diethyl ether; the resulting mixture was successively washed with saturated aqueous $NaHCO_3$ solution (2×120 mL), brine (2×120 mL), and was dried over $Na_2SO_4$. The solution was concentrated in vacuo affording a viscous oil. The crude product was further purified by flash chromatography (30% EtOAc in hexanes) to provide 8.88 g (95%) of the pure titled compound as a off-white foam: mp 54–74° C. APCI-MS m/z 536.4 (MH$^+$).

EXAMPLE 52

Preparation of (S)-2-Amino-1-(4-[bis-(4-fluoro-phenyl)-methyl]-piperazin-1-yl}-3-phenyl-propan-1-one

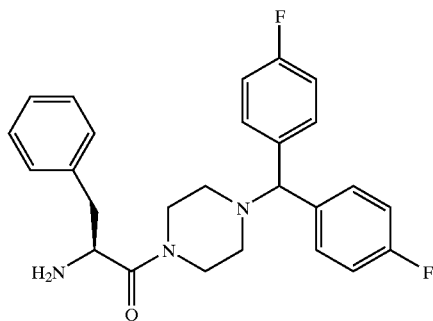

(S)-(1-Benzyl-2-{4-[bis-(4-fluoro-phenyl)-methyl]-piperazin-1-yl}-2-oxo-ethyl)-carbamic acid tert-butyl ester (8.10 g, 15.1 mmol, Example 51) was dissolved in $CH_2Cl_2$ (50 mL) under nitrogen at ambient temperature. To this solution was added trifluoroacetic acid (12 mL). The resulting reaction mixture was stirred for 50 minutes, then concentrated in vacuo. The viscous pale-amber oil obtained was mixed with 50 mL of saturated aqueous $NaHCO_3$ solution and stirred for 10 minutes, 50 mL of $CH_2Cl_2$ was then added. The resulting mixture was stirred until bubbling ceased. The two layers were separated, organic layer was successively washed with saturated aqueous $NaHCO_3$ solution (2×50 mL), brine (2×50 mL), and was dried over $Na_2SO_4$. The solution was concentrated in vacuo affording 6.11 g (92%) of the pure titled compound as a off-white foam: mp 44–51° C. APCI-MS m/z 436.3 (MH$^+$).

EXAMPLE 53

Preparation of (S)-2-Amino-1-{4-[bis-(4-fluoro-phenyl)-methyl]-piperazin-1-yl}-4-methyl-pentan-1-one

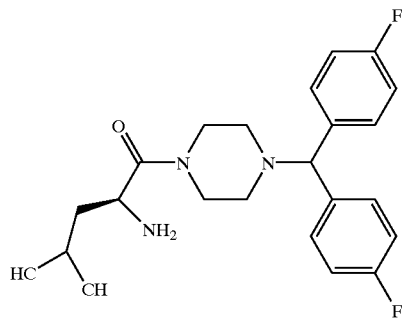

(S)-(1-{4-[Bis-(4-fluoro-phenyl)-methyl]-piperazine-1-carbonyl}-3-methyl-butyl)-carbamic acid tert-butyl ester (7.30 g, 14.6 mmol, Example 50) was dissolved in $CH_2Cl_2$ (50 mL) under nitrogen at ambient temperature. To this solution was added trifluoroacetic acid (12 mL). The resulting reaction mixture was stirred for 50 minutes, then concentrated in vacuo. The viscous pale-amber oil obtained was mixed with 50 mL of saturated aqueous $NaHCO_3$ solution and stirred for 10 minutes, 50 mL of $CH_2Cl_2$ was then added. The resulting mixture was stirred until bubbling ceased. The two layers were separated, organic layer was successively washed with saturated aqueous $NaHCO_3$ solution (2×50 mL), brine (2×50 mL), and was dried over $Na_2SO_4$. The solution was concentrated in vacuo affording 5.92 g (92%) of the pure titled compound as a off-white foam: mp 61–68° C. APCI-MS m/z 402.3 (MH$^+$);

EXAMPLE 54

Preparation of (S)-1-{4-[Bis-(4-fluoro-phenyl)-methyl]-piperazin-1-yl}-2-isopropylamino-3-phenyl-propan-1-one

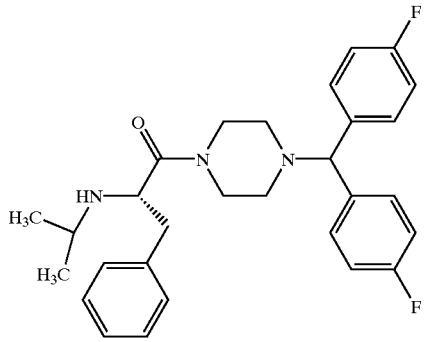

(S)-2-Amino-1-{4-[bis-(4-fluoro-phenyl)-methyl]-piperazin-1-yl}-3-phenyl-propan-1-one (0.500 g, 1.15 mmol, Example 52) and acetone (0.084 mL, 1.15 mmol) were mixed in CH$_2$Cl$_2$ (6 mL). After stirring at ambient temperature under nitrogen atmosphere for 30 minutes, the solution was cooled to 0° C. in an ice-water bath. To this solution was added sodium triacetoxyborohydride (0.365 g, 1.72 mmol). The resulting reaction mixture was stirred for, in succession, 30 minutes at 0° C. and 12 hours at ambient temperature. Twenty milliliters of saturated aqueous NaHCO$_3$ solution was added to the reaction mixture, and the resulting mixture was stirred for 5 minutes. The two layers were separated and the aqueous layer was extracted with CH$_2$Cl$_2$ (2×20 mL). The combined organic solution was dried over Na$_2$SO$_4$. The solution was concentrated in vacuo affording a viscous oil. The crude product was purified by flash chromatography (1% MeOH in EtOAc) affording 460 mg (83%) of the pure titled compound as a white foam: mp 45–58° C. APCI-MS m/z 478.4 (MH$^+$).

EXAMPLE 55

Preparation of (S)-1-{4-[Bis-(4-fluoro-phenyl)-methyl]-piperazin-1-yl}-2-(3-methyl-butylamino)-3-phenyl-propan-1-one dihydrochloride

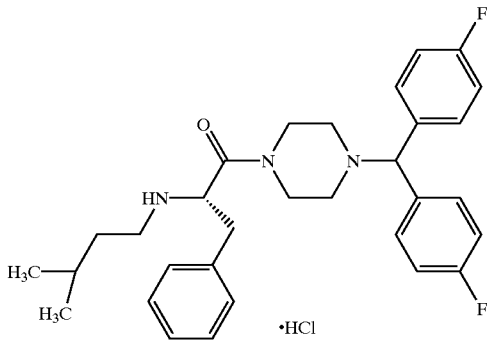

(S)-2-Amino-1-{4-[bis-(4-fluoro-phenyl)-methyl]-piperazin-1-yl}-3-phenyl-propan-1-one (0.500 g, 1.15 mmol, Example 52) and isovaleraldehyde (0.123 mL, 1.15 mmol, Aldrich, Milwaukee, Wis.) were mixed in CH$_2$Cl$_2$ (6 mL). After stirring at ambient temperature under nitrogen atmosphere for 30 minutes, the solution was cooled to 0° C. in an ice-water bath. To this solution was added sodium triacetoxyborohydride (0.365 g, 1.72 mmol). The resulting reaction mixture was stirred for, in succession, 30 minutes at 0° C. and 12 hours at ambient temperature. Twenty milliliters of saturated aqueous NaHCO$_3$ solution was added to the reaction mixture and the resulting mixture was stirred for 5 minutes. The two layers were separated and the aqueous layer was extracted with CH$_2$Cl$_2$ (2×20 mL). The combined organic solution was dried over Na$_2$SO$_4$. TLC (50% EtOAc in Hexanes as the eluant) showed two spots with R$_f$ values 1.0 and 0.29. The solution was concentrated in vacuo affording a viscous oil. The lower spot on TLC (R$_f$=0.29) was isolated by flash chromatography (60% EtOAc in hexanes). The free amine was dissolved in 5 mL of ethyl ether and treated with ethereal HCl to afford 138 mg (20%) of the pure titled compound as a white foam: mp 172–186° C. APCI-MS m/z 506.4 (MH$^+$).

EXAMPLE 56

Preparation of (S)-1-{4-[Bis-(4-fluoro-phenyl)-methyl]-piperazin-1-yl}-2-[bis-(3-methyl-butyl)-amino]-3-phenyl-propan-1-one dihydrochloride

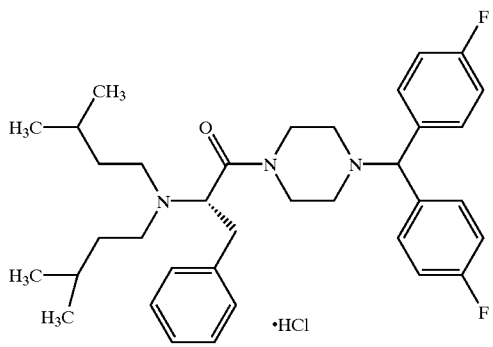

(S)-2-Amino-1-{4-[bis-(4-fluoro-phenyl)-methyl]-piperazin-1-yl}-3-phenyl-propan-1-one (0.500 g, 1.15 mmol, Example 52) and isovaleraldehyde (0.123 mL, 1.15 mmol, Aldrich, Milwaukee, Wis.) were mixed in CH$_2$Cl$_2$ (6 mL). After stirring at ambient temperature under nitrogen atmosphere for 30 minutes, the solution was cooled to 0° C. in an ice-water bath. To this solution was added sodium triacetoxyborohydride (0.365 g, 1.72 mmol). The resulting reaction mixture was stirred for, in succession, 30 minutes at 0° C. and 12 hours at ambient temperature. Twenty milliliters of saturated aqueous NaHCO$_3$ solution was added to the reaction mixture, and the resulting mixture was stirred for 5 minutes. The two layers were separated and the aqueous layer was extracted with CH$_2$Cl$_2$ (2×20 mL). The combined organic solution was dried over Na$_2$SO$_4$. TLC (50% EtOAc in Hexanes as the eluant) showed 2 spots with R$_f$ values 1.0 and 0.29. The solution was concentrated in vacuo affording a viscous oil. The top spot on TLC (R$_f$=1.0) was isolated by flash chromatography (60% EtOAc in hexanes). The free amine was dissolved in 5 mL of ethyl ether and treated with ethereal HCl to afford 280 mg (72%) of the pure titled compound as a white foam: mp 139–181° C. APCI-MS m/z 576.5 (MH$^+$).

EXAMPLE 57

Preparation of (S)-2-[Bis-(4-tert-butoxy-benzyl)-amino]-1-{4-[bis-(4-fluoro-phenyl)-methyl]-piperazin-1-yl}-4-methyl-pentan-1-one

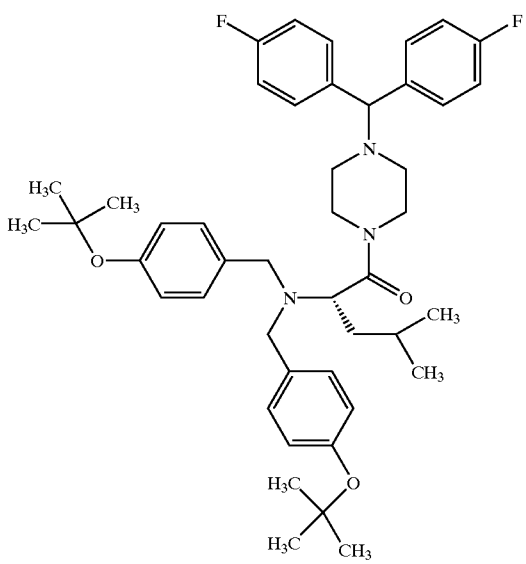

(S)-2-Amino-1-{4-[bis-(4-fluoro-phenyl)-methyl]-piperazin-1-yl}-4-methyl-pentan-1-one (0.500 g, 1.25 mmol, Example 53) and 4-(tert-butoxy)benzaldehyde (0.229 mL, 1.25 mmol, Lancaster) were mixed in CH$_2$Cl$_2$ (6 mL). After stirring at ambient temperature under nitrogen atmosphere for 30 minutes, the solution was cooled to 0° C. in an ice-water bath. To this solution was added sodium triacetoxyborohydride (0.396 g, 1.87 mmol). The resulting reaction mixture was stirred for, in succession, 30 minutes at 0° C. and 12 hours at ambient temperature. Twenty milliliters of saturated aqueous NaHCO$_3$ solution was added to the reaction mixture and the resulting mixture was stirred for 25 minutes. The two layers were separated, and the aqueous layer was extracted with CH$_2$Cl$_2$ (2×20 mL). The combined organic solution was dried over Na$_2$SO$_4$. TLC (50% EtOAc in Hexanes as the eluant) showed two spots with R$_f$ values 0.9 and 0.55. The solution was concentrated in vacuo affording a viscous oil. The top spot on TLC (R$_f$=0.9) was isolated by flash chromatography (30% EtOAc in hexanes). 0.101 g (11.2%) of the pure titled compound was obtained as a white foam: mp 62–67° C. APCI-MS m/z 726.6 (MH$^+$).

EXAMPLE 58

Preparation of (S)-1-{4-[Bis-(4-fluoro-phenyl)-methyl]-piperazin-1-yl}-2-(4-tert-butyl-benzylamino)-4-methyl-pentan-1-one

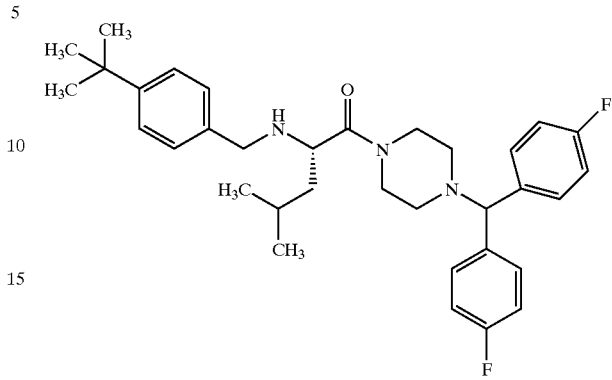

(S)-2-Amino-1-{4-[bis-(4-fluoro-phenyl)-methyl]-piperazin-1-yl}-4-methyl-pentan-1-one (0.500 g, 1.25 mmol, Example 53) and 4-(tert-butyl)benzaldehyde (0.208 mL, 1.25 mmol, Aldrich, Milwaukee, Wis.) were mixed in CH$_2$Cl$_2$ (6 mL). After stirring at ambient temperature under nitrogen atmosphere for 30 minutes, the solution was cooled to 0° C. in an ice-water bath. To this solution was added sodium triacetoxyborohydride (0.396 g, 1.87 mmol). The resulting reaction mixture was stirred for, in succession, 30 minutes at 0° C. and 12 hours at ambient temperature. Twenty milliliters of saturated aqueous NaHCO$_3$ solution was added to the reaction mixture and the resulting mixture was stirred for 15 minutes. The two layers were separated and the aqueous layer was extracted with CH$_2$Cl$_2$ (2×20 mL). The combined organic solution was dried over Na$_2$SO$_4$. TLC (50% EtOAc in Hexanes as the eluant) showed two spots with R$_f$ values 0.93 and 0.63. The solution was concentrated in vacuo affording a viscous oil. The lower spot on TLC (R$_f$=0.63) was isolated by flash chromatography (30% EtOAc in hexanes). 0.496 g (73%) of the pure titled compound was obtained as a white foam: mp 57–62° C. APCI-MS m/z 548.5 (MH$^+$).

EXAMPLE 59

Preparation of (S)-2-[Bis-(4-tert-butyl-benzyl)-amino]-1-{-4-[bis-(4-fluoro-phenyl)-methyl]-piperazin-1-yl}-4-methyl-pentan-1-one

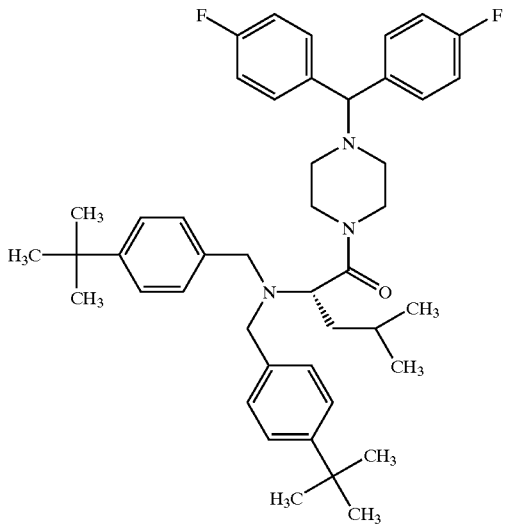

(S)-2-Amino-1-{4-[bis-(4-fluoro-phenyl)-methyl]-piperazin-1-yl}-4-methyl-pentan-1-one (0.500 g, 1.25 mmol, Example 53) and 4-(tert-butyl)benzaldehyde (0.208 mL, 1.25 mmol, Aldrich, Milwaukee, Wis.) were mixed in CH$_2$Cl$_2$ (6 mL). After stirring at ambient temperature under nitrogen atmosphere for 30 minutes, the solution was cooled to 0° C. in an ice-water bath. To this solution was added sodium triacetoxyborohydride (0.396 g, 1.87 mmol). The resulting reaction mixture was stirred for, in succession, 30 minutes at 0° C. and 12 hours at ambient temperature. Twenty milliliters of saturated aqueous NaHCO$_3$ solution was added to the reaction mixture and the resulting mixture was stirred for 15 minutes. The two layers were separated and the aqueous layer was extracted with CH$_2$Cl$_2$ (2×20 mL). The combined organic solution was dried over Na$_2$SO$_4$. TLC (50% EtOAc in Hexanes as the eluant) showed two spots with R$_f$ values 0.93 and 0.63. The solution was concentrated in vacuo affording a viscous oil. The top spot on TLC (R$_f$=0.93) was isolated by flash chromatography (30% EtOAc in hexanes). Seventeen percent (0.146 g) of the pure titled compound was obtained as a white foam: mp 78–86° C. APCI-MS m/z 694.6 (MH$^+$).

EXAMPLE 60

Preparation of (S)-1-{4-[Bis-(4-fluoro-phenyl)-methyl]-piperazin-1-yl}-4-methyl-2-(3,4,5-trimethoxy-benzylamino)-pentan-1-one

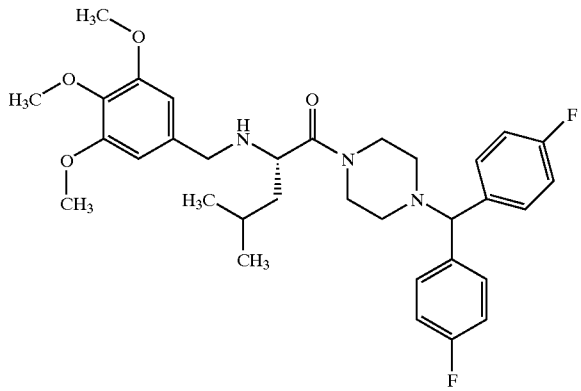

(S)-2-Amino-1-{4-[bis-(4-fluoro-phenyl)-methyl]-piperazin-1-yl}-4-methyl-pentan-1-one (0.500 g, 1.25 mmol, Example 53) and 3,4,5-trimethoxybenzaldehyde (0.244 g, 1.25 mmol, Aldrich, Milwaukee, Wis.) were mixed in CH$_2$Cl$_2$ (6 mL). After stirring at ambient temperature under nitrogen atmosphere for 30 minutes, the solution was cooled to 0° C. in an ice-water bath. To this solution was added sodium triacetoxyborohydride (0.396 g, 1.87 mmol). The resulting reaction mixture was stirred for, in succession, 30 minutes at 0° C. and 12 hours at ambient temperature. Twenty milliliters of saturated aqueous NaHCO$_3$ solution was added to the reaction mixture and the resulting mixture was stirred for 15 minutes. The two layers were separated, and the aqueous layer was extracted with CH$_2$Cl$_2$ (2×20 mL). The combined organic solution was dried over Na$_2$SO$_4$. TLC (50% EtOAc in Hexanes as the eluant) showed two spots with R$_f$ values 0.46 and 0.15. The solution was concentrated in vacuo affording a viscous oil. The lower spot on TLC (R$_f$=0.15) was isolated by flash chromatography (50% EtOAc in hexanes). Eighty-four percent (0.61 g) of the pure titled compound was obtained as a white foam: mp 58–62° C. APCI-MS m/z 582.4 (MH$^+$).

EXAMPLE 61

Preparation of (S)-1-{4-[Bis-(4-fluoro-phenyl)-methyl]-piperazin-1-yl}-2-cyclohexylamino-3-phenyl-propan-1-one

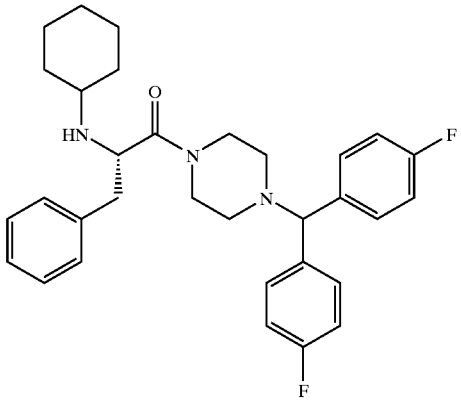

(S)-2-Amino-1-{4-[bis-(4-fluoro-phenyl)-methyl]-piperazin-1-yl}-3-phenyl-propan-1-one (0.500 g, 1.15 mmol, Example 52) and cyclohexanone (0.119 mL, 1.15 mmol, Aldrich, Milwaukee, Wis.) were mixed in CH$_2$Cl$_2$ (6 mL). After stirring at ambient temperature under nitrogen atmosphere for 30 minutes, the solution was cooled to 0° C. in an ice-water bath. To this solution was added sodium triacetoxyborohydride (0.365 g, 1.72 mmol). The resulting reaction mixture was stirred for, in succession, 30 minutes at 0° C. and 12 hours at ambient temperature. Twenty milliliters of saturated aqueous NaHCO$_3$ solution was added to the reaction mixture and the resulting mixture was stirred for 10 minutes. The two layers were separated and the aqueous layer was extracted with CH$_2$Cl$_2$ (2×20 mL). The combined organic solution was dried over Na$_2$SO$_4$. The solution was concentrated in vacuo affording a viscous oil. The crude product was purified by flash chromatography (40% EtOAc in hexanes) affording 444 mg (75%) of the pure titled compound as a white foam: mp 60–64° C. APCI-MS m/z 518.4 (MH$^+$).

EXAMPLE 62

Preparation of (S)-2-Benzylamino-1-{4-[bis-(4-fluoro-phenyl)-methyl]-piperazin-1-yl}-4-methyl-pentan-1-one

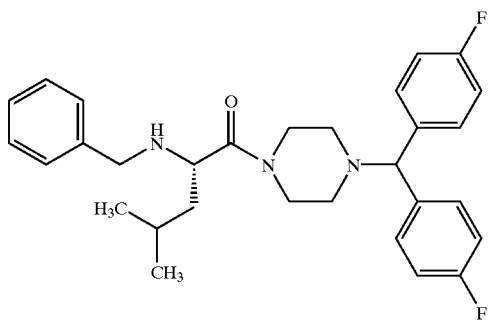

A mixture of 0.127 mL (1.245 mmol) benzaldehyde, and 500 mg of (S)-2-amino-1-{4-[bis-(4-fluoro-phenyl)-methyl]-piperazin-1-yl}-4-methyl-pentan-1-one (1.245 mmol, Example 53) [leubenzhydrylpiperizine] in 6 mL dichloromethane was stirred at 25° C. for 30 minutes, cooled to 3° C., and treated with 396 mg (1.87 mmol) sodium triacetoxyborohydride. After stirring 30 minutes at 3° C., the mixture was warmed to 25° C., and stirred 16 hours when 20 mL saturated aqueous sodium bicarbonate solution was added. The layers were separated, and the aqueous layer was extracted with three 20 mL portions of dichloro methane, which were combined and dried over anhydrous sodium sulfate and concentrated at reduced pressure. The residue thus obtained was purified by column chromatography using 30% ethyl acetate in hexane as eluant. There was obtained 356 mg [si59] (58%) as a viscous oil. APCI-MS 492.4 [MH+].

Microanalysis for $C_{30}H_{35}N_3O_1F_2$: C, 72.36; H, 7.23; N, 8.44; F, 7.63; $H_2O$, 1.27. Found: C, 72.37; H, 7.35; N, 8.25; F, 7.24; $H_2O$, 1.18.

EXAMPLE 63

Preparation of (S)-1-{4-[Bis-(4-fluoro-phenyl)-methyl]-piperazin-1-yl}-4-methyl-2-(tetrahydro-pyran-4-ylamino)-pentan-1-one

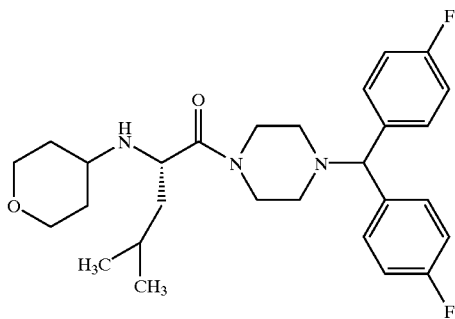

A solution of 430 mg (2.0 mmol) (S)-4-Methyl-2-(tetrahydro-pyran-4-ylamino)-pentanoic acid (Example 18, Step A), 570 mg (2.0 mmol) 1-bis(4-fluorophenyl)-methyl piperazine (Acros Chemical, New Jersey 07621), and 1.8 mL (4.0 mmol) benzyltrimethylammonium methoxide (40% solution in methanol) in 4 mL dry DMF was cooled in an ice bath. Seven hundred sixty milligrams (2.0 mmol) O-Benzotriazol-1-yl-N,N,N',N'-bis(tetramethylene)uronium hexafluorophosphate was added and the resulting mixture stirred at 3° for 30 minutes, warmed to 25° C., and stirred an additional 30 minutes at which time it was diluted with 50 mL diethyl ether, and washed with 50 mL saturated aqueous sodiumbicarbonate solution and twice with 50 mL brine, dried over anhydrous sodium sulfate and concentrated at reduced pressure. The residue thus obtained was further purified by silica gel chromatography using 1:1 ethyl acetate:hexanes containing 3% methanol as eluant, to give 809 mg (80%) of titled compound. APCI-MS 486.3 (MH+).

Microanalysis $C_{30}H_{35}N_3O_1F_2$: C, 66.78; H, 7.81; N, 8.34; $H_2O$, 3.58. Found: C, 66.47; H, 7.60; N, 8.28; $H_2O$, 3.77.

EXAMPLE 64

Preparation of (S)-1-{4-[Bis-(4-fluoro-phenyl)-methyl]-piperazin-1-yl}-2-(4-tert-butoxy-benzylamino)-4-methyl-pentan-1-one

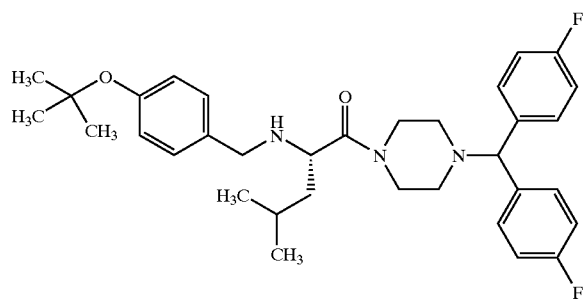

(S)-2-Amino-1-{4-[bis-(4-fluoro-phenyl)-methyl]-piperazin-1-yl}4-methyl-pentan-1-one (0.500 g, 1.25 mmol, Example 53) and 4-(tert-butoxy)benzaldehyde (0.229 mL, 1.25 mmol, Lancaster) were mixed in $CH_2Cl_2$ (6 mL). After stirring at ambient temperature under nitrogen atmosphere for 30 minutes, the solution was cooled to 0° C. in an ice-water bath. To this solution was added sodium triacetoxyborohydride (0.396 g, 1.87 mmol). The resulting reaction mixture was stirred for, in succession, 30 minutes at 0° C. and 12 hours at ambient temperature. Twenty milliliters of saturated aqueous $NaHCO_3$ solution was added to the reaction mixture, and the resulting mixture was stirred for 25 minutes. The 2 layers were separated, and the aqueous layer was extracted with $CH_2Cl_2$ (2×20 mL). The combined organic solution was dried over $Na_2SO_4$. TLC (50% EtOAc in Hexanes as the eluant) showed two spots with $R_f$ values 0.9 and 0.55. The solution was concentrated in vacuo affording a viscous oil. The lower spot on TLC ($R_f$=0.55) was isolated by flash chromatography (30% EtOAc in hexanes). Forty-four percent (0.311 g) of the pure titled compound was obtained as a white foam: mp 56–61° C. APCI-MS m/z 564.5 (MH+).

EXAMPLE 65

Preparation of (S)-N-[4,4-Bis-(4-fluoro-phenyl)-butyl]-2-isopropylamino-3-methyl-butyramide

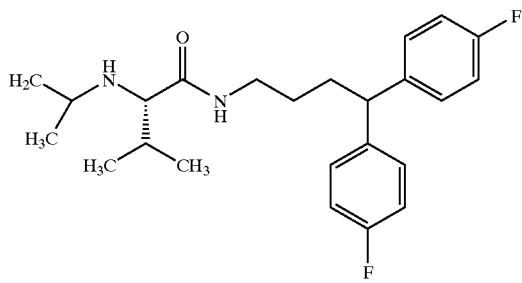

Step A. (S)-2-Isopropylamino-3-methyl-butyric acid

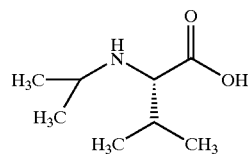

A mixture of L-valine (29.29 g, 250 mmol)6 and acetone (18.36 mL, 500 mmol, Malinckrodt Baker Inc., Paris, Ky. 40361) was agitated in an atmosphere of hydrogen (pressure, 41–50 psi) at room temperature in 500 mL ethanol in the presence of Pd/C (20%, 4 g) until the absorption of hydrogen had ceased. The mixture was filtered, and the filter cake washed with 450 mL 1 M HCl. The filtrate was treated with concentrated aqueous sodium hydroxide (29.8%) to adjust the pH to 5.5, and concentrated to dryness under reduced pressure. The white solid thus obtained was extracted by stirring 2 to 3 hours vigorously with 250 mL methanol followed by filtration. This process was repeated several times. The combined extracts were concentrated under reduced pressure, and the white solid thus obtained was recrystallized from methanol and dried under vacuum to give 36.48 g (92%) of the pure titled compound in two crops as a white solid: mp >300° C. APCI-MS m/z 160.2 (MH+).

Step B

A solution of 267 mg (1.68 mmol) (S)-2-isopropylamino-3-methyl-butyric acid, 500 mg (1.68 mmol) 4-fluoro-d-(4-fluorophenyl)benzenebutanamine, 292 mL (1.68 mmol) N,N-diisopropylethylamine, and 1.5 mL (3.36 mmol) benzyltrimethylammonium methoxide (40% solution in methanol) in 4 mL dry DMF was cooled to 3° C. and 637 mg (1.68 mmol) O-Benzotriazol-1-yl-N,N,N',N'-bis (tetramethylene)uronium hexafluorophosphate was added and the resulting mixture stirred at 3° C. for 30 minutes, warmed to 25° C., and stirred an additional 30 minutes, at which time it was diluted with 20 mL diethyl ether, and washed with 20 mL saturated aqueous sodiumbicarbonate solution and twice with 20 mL brine, dried over anhydrous sodium sulfate and concentrated at reduced pressure. The residue thus obtained was further purified by silica gel chromatography using 4:1 ethyl acetate:hexanes as eluant, followed by conversion to the hydrochloride salt by treating with excess diethyl ether which had been saturated with hydrogen chloride gas to give 122 mg (16%) of the titled compound: mp 72–80° C. APCI-MS m/z 403.3 (MH+).

EXAMPLE 66

Preparation of (S)-N-[4,4-Bis-(4-fluoro-phenyl)-butyl]-2-sec-butylamino-3-methyl-butyramide

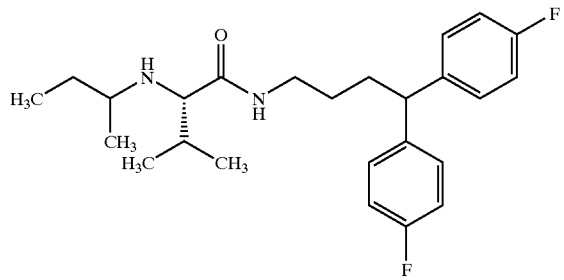

Step A. (S)-2-sec-Butylamino-3-methyl-butyric acid

A mixture of L-valine (29.29 g, 250 mmol), and 2-butanone (44.8 mL, 500 mmol, Aldrich Inc, Milwaukee, Wis.) was agitated in an atmosphere of hydrogen (pressure, 39–51 psi) at 45° C. in 500 mL ethanol in the presence of Pd/C (20%, 4 g) until the absorption of hydrogen had ceased. The mixture was filtered, and this ethanolic filtrate was set aside, then the filter cake washed with 450 mL 1 M HCl. The ethanolic filtrate was concentrated to dryness and the residue dissolved in the aqueous filtrate above, which was treated with concentrated aqueous sodium hydroxide (29.8%) to adjust the pH to 5.5, and the mixture concentrated to dryness under reduced pressure. The white solid thus obtained was extracted by stirring 2–3 hours vigorously with 250 mL methanol followed by filtration. This process was repeated several times. The combined extracts were concentrated under reduced pressure and the white solid thus obtained was triturated in warm acetone, filtered, and the solids washed with acetone and dried under vacuum to give 23.4 g (54%) of the pure titled compound as a white solid; mp >300° C. APCI-MS m/z 174.2 (MH+).

Step B

A solution of 291 mg (1.68 mmol) (S)-2-sec-butylamino-3-methyl-butyric acid, 500 mg (1.68 mmol) 4,4-bis-(4-fluoro-phenyl)-butylamine, 0.29 mL (1.68 mmol) N,N-diisopropylethylamine, and 1.5 mL (3.36 mmol) benzyltrimethylammonium methoxide (40% solution in methanol) in 4 mL dry DMF was cooled to 3° C. and 637 mg (1.68 mmol) O-Benzotriazol-1-yl-N,N,N',N'-bis (tetramethylene)uronium hexafluorophosphate was added and the resulting mixture stirred at 3° for 30 minutes, warmed to 25° C., and stirred an additional 30 minutes at which time it was diluted with 20 mL diethyl ether, and washed with 20 mL saturated aqueous sodiumbicarbonate solution and twice with 20 mL brine, dried over anhydrous sodium sulfate and concentrated at reduced pressure. The residue thus obtained was further purified by silica gel chromatography using 70% ethyl acetate/hexanes as eluant, followed by conversion to the hydrochloride salt by treating with excess diethyl ether which had been saturated with hydrogen chloride gas to give 270 mg (35%) of titled compound: mp 77–81° C. APCI-MS m/z417.4 (MH+).

EXAMPLE 67

Preparation of (S)-{4-[4,4-Bis-(4-fluoro-phenyl)-butylcarbamoyl]-4-tert-butoxycarbonylamino-butyl}-carbamic acid tert-butyl ester

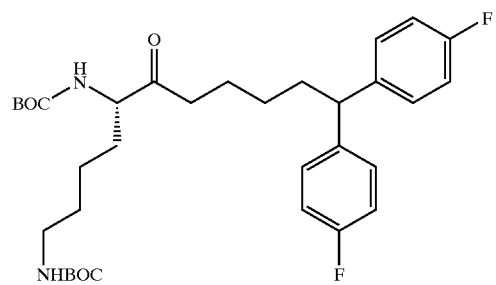

A solution of 581 mg (1.68 mmol) BOC-Lys(Boc)-OH (Bachem Inc., Torrance, Calif.), 0.88 mL (5 mmol) N,N-diisopropylethylamine, and 636 mg (1.68 mmol) O-benzotriazol-1-yl-N,N,N,',N'-bis(tetramethylene) uronium hexafluorophosphate in 4 mL dry DMF was stirred at 3° for 35 minutes, at which time 500 mg (1.68 mmol) 4,4-bis-(4-fluoro-phenyl)-butylamine monohydrochloride was added, and the reaction stirred an additional 30 minutes at which time it was diluted with 20 mL diethyl ether, and washed with 20 mL saturated aqueous sodiumbicarbonate solution and twice with 20 mL brine, dried over anhydrous sodium sulfate and concentrated at reduced pressure. The residue thus obtained was further purified by silica gel chromatography using 1:1 ethyl acetate:hexanes as eluant, to give 814 mg (81%) of titled compound; mp 54–59° C. APCI-MS m/z 590.4(MH+).

EXAMPLE 68

Preparation of (S)-2-(Isopropyl-methyl-amino)-4-methyl-pentanoic acid [4,4-bis-(4-fluoro-phenyl)-butyl]-amide

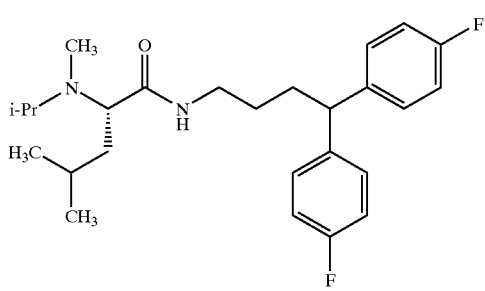

Step A. 2-(Isopropyl-methyl-amino)-4-methyl-pentanoic acid

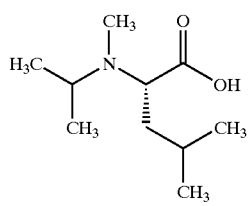

A mixture of (S)-2-isopropylamino-4-methyl-pentanoic acid (70.86 g, 0.41 mol, Example 19, Step A) and aqueous HCHO (94 mL of 37.2%) was agitated in an atmosphere of hydrogen (pressure, 47–52 psi) at 50° C. in absolute ethanol (1.5 L) in the presence of Pd/C (20%, 5 g) until the absorption of hydrogen almost ceased. The catalyst was removed by filtration. The filtrate was concentrated in vacuo to dryness. One hundred milliliters of water was added and concentrated to dryness, and this operation was repeated twice to remove most of HCHO. Absolute ethanol (100 mL) was then added and concentrated to dryness to remove residual water. The white solid collected was triturated with acetone. Filtration and drying under vacuum gave 69.39 g (89%) of the desired product as a white solid; mp 159–160° C. APCI-MS m/z 188.2 (MH+).

Step B

A solution of 297 mg (1.68 mmol) 2-(isopropyl-methyl-amino)-4-methyl-pentanoic acid, 0.88 mL (5 mmol) N,N-diisopropylethylamine, and 636 mg (1.68 mmol) O-Benzotriazol-1-yl-N,N,N',N'-bis(tetramethylene)uronium hexafluorophosphate in 4 mL dry DMF was stirred at 3° for 60 minutes, at which time 500 mg (1.68 mmol) 4,4-bis-(4-fluoro-phenyl)-butylamine monohydrochloride was added and the reaction stirred an additional 10 minutes at 3°, then warmed to 25° C. for 40 minutes at which time it was diluted with 20 mL diethyl ether and washed with 20 mL saturated aqueous sodium bicarbonate solution and twice with 20 mL brine, dried over anhydrous sodium sulfate and concentrated at reduced pressure. The residue thus obtained was further purified by silica gel chromatography using 60% ethyl acetate in hexanes as eluant, followed by conversion to the hydrochloride salt by treating with excess diethyl ether which had been saturated with hydrogen chloride gas to give 648 mg (83%) of titled compound: mp 155–156° C. APCI-MS m/z 431.4 (MH+).

EXAMPLE 69

Preparation of (S)-N-[4,4-Bis-(4-fluoro-phenyl)-butyl]-2-(cyclohexyl-methyl-amino)-3-methyl-butyramide

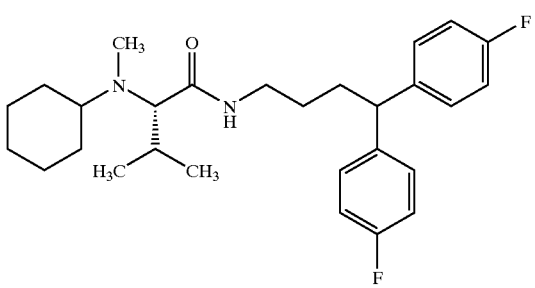

Step A. (S)-2-Cyclohexylamino-3-methyl-butyric acid

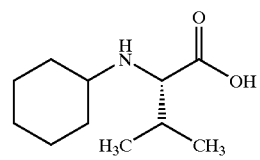

A mixture of L-valine (29.29 g, 250 mmol), and cyclohexanone (51.8 mL, 500 mmol, Aldrich Inc, Milwaukee, Wis.) was agitated in an atmosphere of hydrogen (pressure, 23.4–51.1 psi) at room temperature in 370 mL ethanol in the presence of Pd/C (20%, 3 g) until the absorption of hydrogen had ceased. The mixture was filtered, and this ethanolic filtrate was set aside, then the filter cake washed with 450 mL 1 M HCl. The ethanolic filtrate was concentrated to dryness and the residue dissolved in the aqueous filtrate above, which was treated with concentrated aqueous sodium hydroxide (29.8%) to adjust the pH to 5.5. The white solid precipitated out which was isolated via filtration, washed with two 150 mL portions of ethanol and dried under vacuum to give 37.4 g (70%) of the pure titled compound as a white solid; mp >300° C. APCI-MS m/z 200.2 (MH+).

Step B. (S)-2-(Cyclohexyl-methyl-amino)-3-methyl-butyric acid

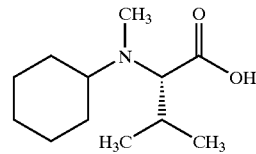

A mixture of (S) 2-(cyclohexylamino)-3-methylbutyric acid (14.95 g, 75 mmol) (S)-2-cyclohexylamino-3-methyl-butyric acid and aqueous HCHO (17 mL of 37.2%, 6.32 g, 211 mmol) was agitated in an atmosphere of hydrogen (pressure, 44–51 psi) at 50° C. in absolute ethanol (500 mL) in the presence of Pd/C (20%, 2 g) until the absorption of hydrogen almost ceased. The catalyst was removed by filtration. The filtrate was concentrated in vacuo to dryness. Fifty milliliters of water was added and concentrated to dryness, and this operation was repeated twice to remove most of HCHO. Absolute ethanol (50 mL) was then added and concentrated to dryness to remove residual water. The white solid collected was recrystallized from methanol. Filtration and drying under vacuum gave 9.34 g (58%) of the desired product as a white solid; mp 185–190° C. (decomposed). APCI-MS m/z 230.2 (MH$^+$).

Step C

A solution of 358 mg (1.68 mmol) (S)-2-(cyclohexyl-methyl-amino)-3-methylbutyric acid, 0.88 mL (5 mmol) N,N-diisopropylethylamine, and 636 mg (1.68 mmol) O-Benzotriazol-1-yl-N,N,N',N'-bis(tetramethylene)uronium hexafluorophosphate in 4 mL dry DMF was stirred at 3° for 60 minutes, at which time 500 mg (1.68 mmol) 4,4-bis-(4-fluoro-phenyl)-butylamine monohydrochloride was added, and the reaction stirred an additional 10 minutes at 3°, then warmed to 25° C. for 50 minutes at which time it was diluted with 20 mL diethyl ether, and washed with 20 mL saturated aqueous sodiumbicarbonate solution and twice with 20 mL brine, dried over anhydrous sodium sulfate and concentrated at reduced pressure. The residue thus obtained was further purified by silica gel chromatography using 40% ethyl acetate in hexanes as eluant, followed by conversion to the hydrochloride salt by treatment with excess diethyl ether which had been saturated with hydrogen chloride gas to give 577 mg (68%) mp 82–86° C. APCI-MS m/z 457.4 (MH$^+$).

EXAMPLE 70

Preparation of (S)-N-[4,4-Bis-(4-fluoro-phenyl)-butyl]-2-cyclohexylamino-3-methyl-butyramide

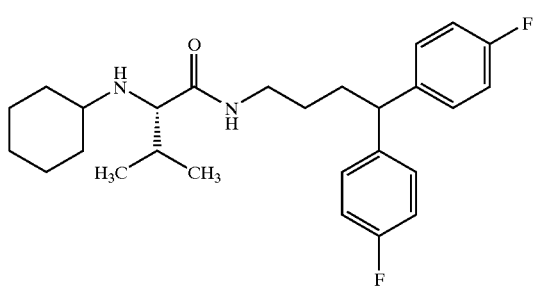

A solution of 335 mg (1.68 mmol) 2-(cyclohexylamino)-3-methylbutyric acid (Example 69, Step A), 500 mg (1.68 mmol) 4,4-bis-(4-fluoro-phenyl)-butylamine monohydrochloride, 0.29 mL (1.68 mmol) N,N-diisopropylethylamine, and 1.5 mL (3.36 mmol) benzyltrimethylammonium methoxide (40% solution in methanol) in 4 mL dry DMF was cooled to 3° C., and 637° mg (1.68 mmol) O-benzotriazol-1-yl-N,N,N',N'-bis(tetramethylene) uronium hexafluorophosphate was added and the resulting mixture stirred at 3° for 30 minutes, warmed to 25° C., and stirred an additional 30 minutes at which time it was diluted with 20 mL diethyl ether, and washed with 20 mL saturated aqueous sodiumbicarbonate solution and twice with 20 mL brine, dried over anhydrous sodium sulfate and concentrated at reduced pressure. The residue thus obtained was further purified by silica gel chromatography using 4:1 ethyl acetate:hexanes as eluant, followed by conversion to the hydrochloride salt by treating with excess diethyl ether which had been saturated with hydrogen chloride gas to give 29 mg (4%) of titled compound: mp 49–53° C. APCI-MS m/z 443.4 (MH$^+$).

EXAMPLE 71

(R)-4-Methyl-2-methylamino-pentanoic acid [4,4-bis-(4-fluorophenyl)-butyl]-amide monohydrochloride

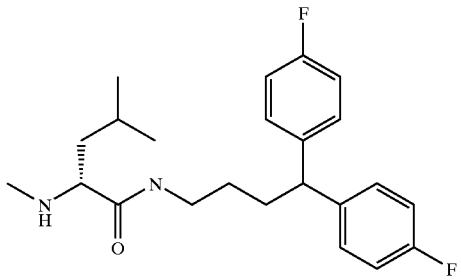

(R)-4-Methyl-2-methylamino-pentanoic acid [4,4-bis-(4-fluorophenyl)-butyl]-amide monohydrochloride was prepared in accordance with the methods of Example 12, except that N-tert-butoxycarbonyl-N-methyl-D-leucine was used instead of N-tert-butoxycarbonyl-N-methyl-L-leucine in Step A, and (R)-4-methyl-2-methylamino-pentanoic acid [4,4-bis-(4-fluoro-phenyl)-butyl]-amide was used instead of (S)-4-methyl-2-methylamino-pentanoic acid [4,4-bis-(4-fluoro-phenyl)-butyl]-amide in Step B. MS: 389.3 (M+1 for $C_{23}H_{30}N_2F_2O_1$); a white solid; mp: 85–90° C.;

Analysis ($C_{23}H_{30}N_2F_2O_1$.HCl.0.5H$_2$O): (calc.) C, 63.66; H, 7.45; N, 6.45. (found) C, 64.18; H, 7.56; N, 5.99.

EXAMPLE 72

(S)-2-Hydroxy-4-methyl-pentanoic acid [4,4-bis-(4-fluoro-phenyl)-butyl]-amide

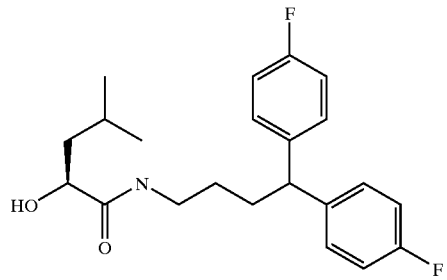

(S)-2-Hydroxy-4-methyl-pentanoic acid [4,4-bis-(4-fluoro-phenyl)-butyl]-amide: L-2-hydroxyisocaproic acid (102 mg, 0.77 mmol) was dissolved in DMF (5 mL) and treated with N,N-diisopropylethylamine (0.53 mL, 3.06 mmol), 4,4-bis-(4-fluorophenyl)-butylamine (200 mg, 0.77 mmol), and HBTU (292 mg, 0.77 mmol), then stirred overnight at room temperature. The reaction was diluted with EtOAc (125 mL), washed with saturated bicarbonate solution and brine, dried over Na$_2$SO$_4$, and concentrated. The residue was chromatographed twice on silica gel, eluting with 2–4% MeOH/CH$_2$Cl$_2$ to give 139 mg (48%) of the desired product as an oil. MS: 376.2 (M+1 for $C_{22}H_{27}N_1O_2F_2$); an oil; TLC (SiO$_2$), Rf 0.73 (8% MeOH/CH$_2$Cl$_2$); HPLC (7:3 CH$_3$CN/H$_2$O with 0.1% TFA, C-18 column) 96.46%, RT=5.448 min.

EXAMPLE 73

(S)-3-Methyl-2-methylamino-butanoic acid [4,4-bis-(4-fluorophenyl)-butyl]-amide monohydrochloride

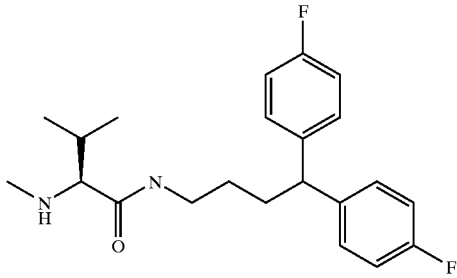

(S)-3-Methyl-2-methylamino-butanoic acid [4,4-bis-(4-fluorophenyl)-butyl]-amide monohydrochloride was prepared in accordance with the methods of Example 12, except that N-tert-butoxycarbonyl-N-methyl-L-valine was used instead of N-tert-butoxycarbonyl-N-methyl-L-leucine in Step A, and (S)-1-[4,4-bis-(4-fluoro-phenyl)-butylcarbamoyl]-2-methyl-propyl)-methyl-carbamic acid tert-butyl ester was used instead of (S)-4-methyl-2-methylamino-pentanoic acid [4,4-bis-(4-fluoro-phenyl)-butyl]-amide in Step B. MS: 375.3 (M+1 for $C_{22}H_{28}N_2F_2O_1$); a white solid; mp: 85–90° C.;

Analysis ($C_{22}H_{28}N_2F_2O_1$·HCl·0.65H$_2$O): (calc) C, 62.52; H, 7.24; N, 6.63. (found) C, 63.02; H, 7.23; N. 6.25.

EXAMPLE 74

N-[4,4-Bis-(4-fluoro-phenyl)-butyl]-2-methylamino-acetamide

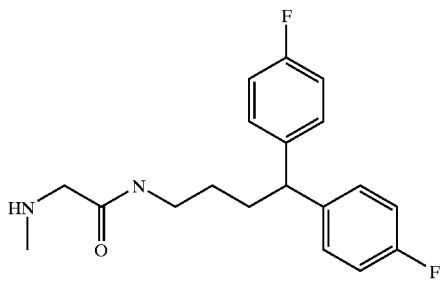

N-[4,4-Bis-(4-fluoro-phenyl)-butyl]-2-methylamino-acetamide was prepared in accordance with the methods of Example 12, except that N-tert-butoxycarbonyl-N-methyl-glycine was used instead of N-tert-butoxycarbonyl-N-methyl-L-leucine in Step A, and {[4,4-bis-(4-fluoro-phenyl)-butylcarbamoyl]-methyl}-methyl-carbamic acid tert-butyl ester was used instead of (S)-1-[4,4-bis-(4-fluoro-phenyl)-butylcarbamoyl]-3-methyl-butyl}-methyl-carbamic acid tert-butyl ester in Step B. MS: 333.2 (M+1 for $C_{19}H_{22}N_2F_2O_1$); an oil;

Analysis. ($C_{19}H_{22}N_2F_2O_1$·0.20H$_2$O): (calc) C, 67.92; H, 6.72; N, 8.34. (found) C, 67.55; H, 6.75; N, 8.15.

EXAMPLE 75

(S)-4-Ethyl-2-methylamino-pentanoic acid [4,4-bis-(4-fluorophenyl)butyl]-amide monohydrochloride

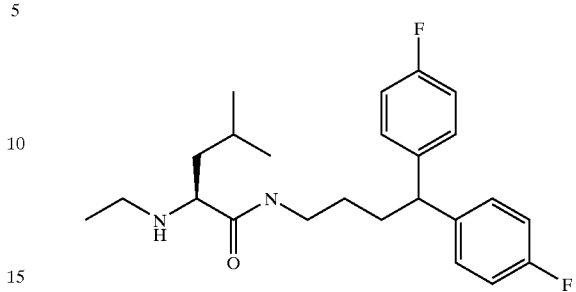

(S)-4-Ethyl-2-methylamino-pentanoic acid [4,4-bis-(4-fluorophenyl)-butyl]-amide monohydrochloride was prepared in accordance with the methods of Example 12, except that N-tert-butoxycarbonyl-N-ethyl-L-leucine was used instead of N-tert-butoxycarbonyl-N-methyl-L-leucine in Step A, and (S)-{1-[4,4-bis-(4-fluoro-phenyl)-butylcarbamoyl]-3-methyl-butyl}-ethyl-carbamic acid tert-butyl ester was used instead of (S)-1-[4,4-bis-(4-fluoro-phenyl)-butylcarbamoyl]-3-methyl-butyl}-methyl-carbamic acid tert-butyl ester in Step B; MS: 403.3 (M+1 for $C_{24}H_{32}N_2F_2O_1$); a white solid; mp: 78–83° C.

Analysis ($C_{24}H_{32}N_2F_2O_1$·HCl·0.25H$_2$O): (calc) C, 64.99; H, 7.63; N, 6.31. (found) C, 64.63; H, 7.74; N, 6.09.

EXAMPLE 76

(S)-$N^1$-[4,4-Bis-(4-fluoro-phenyl)-butyl]-4-$N^2$-dimethyl-pentane-1,2-diamine

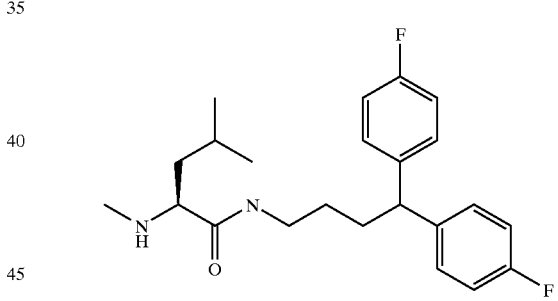

The preparation of $N^1$-[4,4-Bis-(4-fluoro-phenyl)-butyl]-4-$N^2$-dimethyl-pentane-1,2-diamine:

Step 1: (S)-[1-(Methoxy-methyl-carbamoyl)-3-methyl-butyl]-methyl-carbamic acid tert-butyl ester: N-tert-butoxycarbonyl-N-methyl-L-leucine (5.0 g, 20.4 mmol) was dissolved in DMF (100 mL), treated with treated with N,N-diisopropylethylamine (28 mL, 163 mmol), N,N-dimethylhydroxylamine hydrochloride salt (2.0 g, 20.4 mmol), and HBTU (7.73 g, 20.4 mmol), then stirred overnight at room temperature. The reaction was diluted with EtOAc (500 mL), washed with saturated bicarbonate solution and brine, dried over Na$_2$SO$_4$, and concentrated to give the desired product as an oil; MS: 289.2 (M+1 for $C_{14}H_{28}N_2O_4$); TLC (SiO$_2$) Rf 0.39 (8% MeOH/CH$_2$Cl$_2$), visualized with ninhydrin.

Step 2: (S)-(1-Formyl-3-methyl-butyl)-methyl-carbamic acid tert-butyl ester: (S)-[1-(Methoxy-methyl-carbamoyl)-3-methyl-butyl]-methyl-carbamic acid tert-butyl ester (288 mg, 1.0 mmol) was dissolved in Et$_2$O (10 mL), cooled to 0° C., treated with LAH (38 mg, 1.0 mmol), and stirred cold for 30 minutes. The reaction was quenched by dropwise addition of a solution of 150 mg $Na_2S_2O_3$ in 5 mL $H_2O$. The reaction was diluted with $H_2O$ (100 mL), washed with $Et_2O$ (3×100 mL), then the organic layers were combined, washed with saturated bicarbonate solution and brine, dried over $Na_2SO_4$, and concentrated to give the desired product which was carried on immediately without further purification.

Step 3: (S)-(1-{[4,4-Bis-(4-fluoro-phenyl)-butylamino]-methyl}-3-methyl-butyl)-methyl-carbamic acid tert-butyl ester: 4,4-bis-(4-fluorophenyl)-butylamine (200 mg, 0.77 mmol) was dissolved in $CH_2Cl_2$ (5 mL), treated with (S)-(1-formyl-3-methyl-butyl)-methyl-carbamic acid tert-butyl ester (229 mg, 1.0 mmol), stirred for 30 minutes, then cooled to 0° C., treated with $NaBH(OAc)_3$ (245 mg, 1.16 mmol), and stirred overnight at room temperature. The reaction was diluted with EtOAc (100 mL), washed with saturated bicarbonate solution and brine, dried over $Na_2SO_4$, and concentrated. The crude material was chromatographed on silica gel eluting with 4% $MeOH/CH_2Cl_2$ to give 257 mg (70%) of the desired product as an oil. MS: 475.4 (M+1 for $C_{28}H_{40}N_2O_2F_2$); an oil; TLC ($SiO_2$), Rf 0.26 (4% $MeOH/CH_2Cl_2$); HPLC (1:1 $CH_3CN/H_2O$ with 0.1% TFA, C-18 column) 100%, RT=15.013 min.

Step 4: The preparation of Example 76 (S)-(1-{[4,4-Bis-(4-fluoro-phenyl)-butylamino]-methyl}-3-methyl-butyl)-methyl-carbamic acid tert-butyl ester (220 mg, 0.46 mmol) was dissolved in $CH_2Cl_2$ (2 mL), treated with TFA (2 mL), stirred 30 minutes, concentrated, diluted with EtOAc (100 mL), washed three 5 times with saturated bicarbonate solution and once with brine, dried over $Na_2SO_4$, and concentrated. The crude material was chromatographed on silica gel eluting with 8/91.5/0.5 $MeOH/CH_2Cl_2/iPr_2NEt$ to give 142 mg (82%) of the desired product as an oil; MS: 375.3 (M+1 for $C_{23}H_{30}N_2F_2$); an oil; TLC ($SiO_2$) Rf 0.26 (10/89.5/0.5 $MeOH/CH_2Cl_2/iPr_2NEt$).

Analysis ($C_{24}H_{32}N_2F_2O_1$): (calc) C 72.10; H, 8.67; N, 7.31. (found) C, 71.73; H, 8.28; N, 7.23.

EXAMPLE 77

(R)-$N^1$-[4,4-Bis-(4-fluoro-phenyl)-butyl]-4-$N^2$-dimethyl-pentane-1,2-diamine

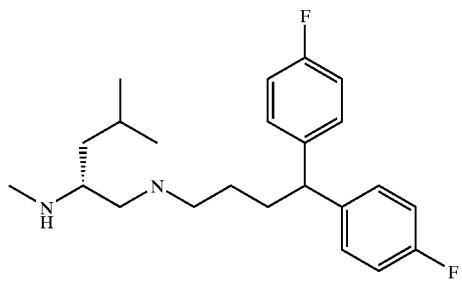

Step 1: (R)-[1-(Methoxy-methyl-carbamoyl)-3-methyl-butyl]-methyl-carbamic acid tert-butyl ester was prepared in accordance with the methods of Step 1 in Example 76, except that N-tert-butoxycarbonyl-N-methyl-D-leucine was used instead of N-tert-butoxycarbonyl-N-methyl-L-leucine. MS: 289.2 (M+1 for $C_{14}H_{28}N_2O_4$); TLC ($SiO_2$) Rf 0.39 (8% $MeOH/CH_2Cl_2$), visualized with ninhydrin.

Step 2: (R)-(1-Formyl-3-methyl-butyl)-methyl-carbamic acid tert-butyl ester was prepared in accordance with the methods of Step 2 in Example 76, except that (R)-[1-(methoxy-methyl-carbamoyl)-3-methyl-butyl]-methyl-carbamic acid tert-butyl ester was used instead of (S)-[1-(methoxy-methyl-carbamoyl)-3-methyl-butyl]-methyl-carbamic acid tert-butyl ester.

Step 3: (R)-(1-{[4,4-Bis-(4-fluoro-phenyl)-butylamino]-methyl}-3-methyl-butyl)-methyl-carbamic acid tert-butyl ester was prepared in accordance with the methods of Step 3 in Example 76, except that (R)-(1-formyl-3-methyl-butyl)-methyl-carbamic acid tert-butyl ester was used instead of (S)-(1-formyl-3-methyl-butyl)-methyl-carbamic acid tert-butyl ester. MS: 475.4 (M+1 for $C_{28}H_{40}N_2O_2F_2$); an oil; TLC ($SiO_2$), $R_f$=0.26 (4% $MeOH/CH_2Cl_2$); HPLC (1:1 $CH_3CN/H_2O$ with 0.1% TFA, C-18 column) 100%, RT=14.758 min.

Analysis ($C_{28}H_{40}N_2F_2O_2 \cdot 0.03H_2O$): (calc) C, 70.78; H, 8.50; N, 5.90. (found) C, 70.39; H, 8.71; N 5.87.

Step 4: Example 77 was prepared in accordance with the methods of Step 4 in Example 76, except that (R)-(1-{[4,4-Bis-(4-fluoro-phenyl)-butylamino]-methyl}-3-methyl-butyl)-methyl-carbamic acid tert-butyl ester was used instead of (S)-(1-{[4,4-Bis-(4-fluoro-phenyl)-butylamino]-methyl}-3-methyl-butyl)-methyl-carbamic acid tert-butyl ester; MS: 375.3 (M+1 for $C_{23}H_{30}N_2F_2$); an oil; TLC ($SiO_2$) Rf 0.26 (10:89.5:0.5 $MeOH/CH_2Cl_2/iPr_2NEt$).

Analysis ($C_{24}H_{32}N_2F_2O_1 \cdot 0.49H_2O$): (calc) C, 72.06; H, 8.67; N, 7.31. (found): C, 71.67; H, 8.52; N, 7.12.

EXAMPLE 78

N-[4,4-Bis-(4-fluoro-phenyl)-butyl]-2-(isobutyl-methyl-amino)-acetamide

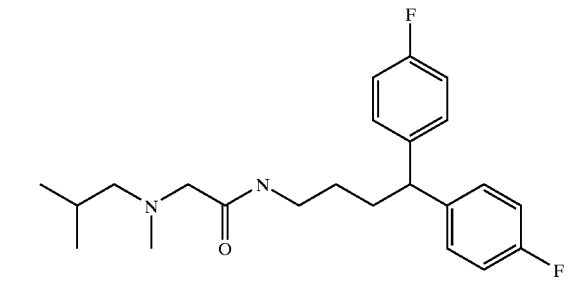

N-[4,4-Bis-(4-fluoro-phenyl)-butyl]-2-methylamino-acetamide (157 mg, 0.47 mmol) was dissolved in $CH_2Cl_2$ (5 mL), treated with isobutyraldehyde (43 mL, 0.47 mmol), stirred for 30 minutes, then cooled to 0° C., treated with $NaBH(OAc)_3$ (150 mg, 0.71 mmol), and stirred overnight at room temperature. The reaction was diluted with EtOAc (100 mL), washed with saturated bicarbonate solution and brine, dried over $Na_2SO_4$, and concentrated. The crude material was chromatographed on silica gel eluting with 4% $MeOH/CH_2Cl$ to give 168 mg (92%) of the desired product as a sticky solid. MS: 389.3 (M+1 for $C_{23}H_{30}N_2O_1F_2$); sticky solid; TLC ($SiO_2$), Rf 0.44 (6% $MeOH/CH_2Cl_2$); HPLC (7:3 $CH_3CN/H_2O$ with 0.1% TFA, C-18 column) 100%, RT=2.067 min.

EXAMPLE 79

(R)-N-[4,4-Bis-(4-fluoro-phenyl)-butyl]-2-methylamino-propionamide

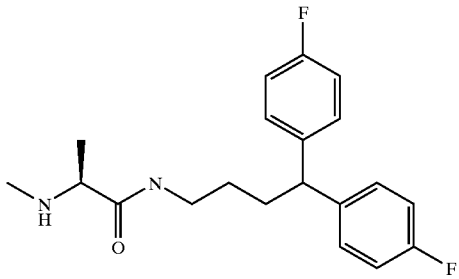

(R)-N-[4,4-Bis-(4-fluoro-phenyl)-butyl]-2-methylamino-propionamide was prepared in accordance with the methods of Example 12, except that: N-tert-butoxycarbonyl-N-methyl-L-alanine was used instead of N-tert-butoxycarbonyl-N-methyl-L-leucine in Step A, and (S){1-[4,4-Bis-(4-fluoro-phenyl)-butylcarbamoyl]-ethyl}-methyl-carbamic acid tert-butyl ester was used instead of (S){1-[4,4-bis-(4-fluoro-phenyl)-butylcarbamoyl]-3-methyl-butyl}-methyl-carbamic acid tert-butyl ester in Step B. MS: 347 (M+1 for $C_{20}H_{24}N_2F_2O_1$); an oil; Rf 0.3 (5% MeOH/$CH_2Cl_2$).

The following compounds can be made in accordance with the synthetic procedures set forth above.

(S){1-[4,4-Bis-(4-fluoro-phenyl)-butylcarbamoyl]-2-methyl-propyl}-methyl-carbamic acid tert-butyl ester;
(S)N-[4,4-Bis-(4-fluoro-phenyl)-butyl]-3-methyl-2-methylamino-butyramide;
(S){1-[4,4-Bis-(4-fluoro-phenyl)-butylcarbamoyl]-2-methyl-butyl}-methyl-carbamic acid tert-butyl ester;
(S)3-Methyl-2-methylamino-pentanoic acid [4,4-bis-(4-fluoro-phenyl)-butyl]-amide;
(S){1-[4,4-Bis-(4-fluoro-phenyl)-butylcarbamoyl]-ethyl}-methyl-carbamic acid tert-butyl ester;
(S)N-[4,4-Bis-(4-fluoro-phenyl)-butyl]-2-methylamino-propionamide;
(S){1-[4,4-Bis-(4-fluoro-phenyl)-butylcarbamoyl]-2-cyclohexyl-ethyl}-methyl-carbamic acid tert-butyl ester;
(S)N-[4,4-Bis-(4-fluoro-phenyl)-butyl]-3-cyclohexyl-2-methylamino-propionamide;
(S){1-[4,4-Bis-(4-fluoro-phenyl)-butylcarbamoyl]-2-cyclohexyl-ethyl}-carbamic acid tert-butyl ester;
(S)2-Amino-N-[4,4-bis-(4-fluoro-phenyl)-butyl]-3-cyclohexyl-propionamide;
{1-[4,4-Bis-(4-fluoro-phenyl)-butylcarbamoyl]-cyclohexyl}-carbamic acid tert-butyl ester;
1-Amino-cyclohexanecarboxylic acid [4,4-bis-(4-fluoro-phenyl)-butyl]-amide;
{1-[4,4-Bis-(4-fluoro-phenyl)-butylcarbamoyl]-cyclohexyl}-methyl-carbamic acid tert-butyl ester;
1-Methylamino-cyclohexanecarboxylic acid [4,4-bis-(4-fluoro-phenyl)-butyl]-amide;
{1-[4,4-Bis-(4-fluoro-phenyl)-butylcarbamoyl]-cyclopentyl}-carbamic acid benzyl ester; and
1-Amino-cyclopentanecarboxylic acid [4,4-bis-(4-fluoro-phenyl)-butyl]-amide.

BIOLOGICAL EXAMPLES

Measurement of N-type $Ca^{2+}$ Channel Blocking Potencies of Compounds in IMR-32 Cells Using the Fluorescent $Ca^{2+}$ Indicator Indo-1

IMR-32 cells are a human tumoral cell line of neural origin. The IMR-32 cell line has been shown to contain both N- and L-type voltage sensitive calcium channels. Calcium flux into these cells may be induced by stimulation with elevated potassium concentrations. The L-channel component of calcium flux may be blocked by adding 5 µM nitrendipine. The remaining component of calcium entry into the IMR-32 cells is due to calcium flux through N-type calcium channels. Intracellular calcium concentrations are measured using the fluorescent calcium indicator Indo-1. The effect of drug concentration on calcium uptake is studied.

Methods

The IMR-32 cell line was obtained from the American Type Culture Collection (Rockville, Md.). Cells were grown in Eagle's Minimum Essential Medium with Earle's salts supplemented with 10% fetal bovine serum, 2 mM L-Gln and antibiotic/antimycotic mixture (Gibco). At approximately 80% confluency, differentiation was induced by the addition of 1 mM dibutyryl cAMP and 2.5 µM bromodeoxyuridine to the medium. After 7 to 13 days of differentiation, cells were detached using 0.5 mM EDTA and loaded with 5 µM Indo-1 acetoxymethyl ester (Molecular Probes, Eugene, Oreg.) at 30° C. for 45 minutes. Loaded cells were washed twice, resuspended (~$10^7$ cells/mL) in assay buffer (10 mM HEPES/Tris pH 7.4 in Hank's Balanced Salt Solution without bicarbonate or phenol red containing 0.5% bovine serum albumin) and kept on ice until use. Fluorescence measurements were carried out in a Photon Technology International (PTI, South Brunswick, N.J.) Model RF-F3004 spectrofluorometer with dual emission monochromators using excitation at 350 nm and emission at 400 and 490 nm. The instrument was equipped with a thermostated cuvette holder with stirring capabilities as well as with a computer-controlled pump which allowed for reagent addition during measurement. Instrument control and data collection was done by PTI's OSCAR software running on an IBM compatible computer. Different concentrations of the test compounds (60 µL in dimethyl sulfoxide) were added to 5.94 mL of assay buffer containing approximately 3×$10^6$ loaded cells, and 5 µM Nitrendipine (in 30 µL EtOH) to block L-type $Ca^{2+}$ channels. Samples were incubated for 10 minutes at 30° C. and the aliquot into three 10×10 mm disposable acrylic cuvettes. Emission signals at 400 and 490 nm were acquired from each cuvette at 30° C. for 50 seconds. At 20 seconds after the start of reading, cells were depolarized by the addition of 160 µL of stimulation solution (1 M KCl, 68 mM $CaCl_2$) to the cuvette via the computer-controlled pump. Ratio of dual emission signals (400/490 nm), which is proportional to intracellular $Ca^{2+}$ concentration, was plotted against time, and the difference between maximal response after stimulation and basal value (before stimulation) was determined. Values obtained in this way were plotted as a function of drug concentration. $IC_{50}$ values of test compounds were calculated by fitting a four-parameter logistic function to the data using the least squares method.

Table of $Ca^{2+}$ Channel Blocking Potency in IMR-32 Cells

| Example No. | IMR32 $IC_{50}$ (µM) |
| --- | --- |
| 1 | 0.820 |
| 3 | 4.4 |
| 4 | 3.30 |
| 5 | 1.80 |
| 6 | 1.30 |
| 7 | 2.40 |
| 8 | 0.460 |
| 9 | 0.280 |

-continued

Table of Ca$^{2+}$ Channel Blocking Potency in IMR-32 Cells

| Example No. | IMR32 IC$_{50}$ ($\mu$M) |
|---|---|
| 10 | 2.60 |
| 11 | 4.00 |
| 12 | 1.43 |
| 13 | 0.520 |
| 14 | 0.840 |
| 15 | 87% @ 10 |
|    | 62% @ 1 |
| 16 | 0.61[b] |
| 17 | 2.0[b] |
| 18 | 2.0[b] |
| 19 | 1.1[b] |
| 20 | 92% @ 10 |
|    | 25% @ 1 |
| 21 | 94% @ 10 |
|    | 71% @ 1 |
| 22 | 94% @ 10 |
|    | 49% @ 1 |
| 23 | 89% @ 10 |
|    | 35% @ 1 |
| 24 | 89% @ 10 |
|    | 35% @ 1 |
| 25 | 0.99[b] |
| 26 | 0.84[b] |
| 27 | 1.2[b] |
| 28 | 97% @ 10 |
|    | 92% @ 1 |
| 29 | 82% @ 10 |
|    | 22% @ 1 |
| 30 | 100% @ 10 |
|    | 39% @ 1 |
| 31 | 0.480 |
| 32 | 0.470 |
| 33 | 0.850 |
| 34 | 1.89[b] |
| 35 | 0.50[b] |
| 36 | 0.50[b] |
| 37 | 2.0[b] |
| 38 | 1.2[b] |
| 39 | 3.5[b] |
| 40 | 0.7[b] |
| 41 | 2.3[b] |
| 42 | 3.4[b] |
| 43 | 0.47[b] |
| 44 | 0.41[b] |
| 45 | 1.5[b] |
| 46 | 0.33[b] |
| 47 | 54% @ 10 |
|    | 13% @ 1 |
| 48 | 1.2[b] |
| 49 | 3.2[b] |
| 50 | 0.55[b] |
| 51 | 0.25[b] |
| 52 | 99% @ 10 |
|    | 23% @ 1 |
| 53 | 78% @ 10 |
|    | 22% @ 1 |
| 54 | 99% @ 10 |
|    | 25% @ 1 |
| 55 | 104% @ 10 |
| 56 | 37 @ 10 |
|    | 16 @ 1 |
| 57 | 7 @ 10 |
| 53 | 86 @ 10 |
|    | 21 @ 1 |
| 59 | 2 @ 10 |
|    | -5 @ 1 |
| 60 | 95 @ 10 |
|    | 26 @ 1 |
| 61 | 102 @ 10 |
|    | 42 @ 1 |
| 62 | 99% @ 10 |
| 65 | 83% @ 10 |
| 66 | 94% @ 10 |
|    | 34% @ 1 |

-continued

Table of Ca$^{2+}$ Channel Blocking Potency in IMR-32 Cells

| Example No. | IMR32 IC$_{50}$ ($\mu$M) |
|---|---|
| 67 | 92% @ 10 |
|    | 35% @ 1 |
| 68 | 97% @ 10 |
| 69 | 99% @ 10 |
|    | 34% @ 1 |

[a]Percent of inhibition at certain concentration in $\mu$M
[b]Estimated IC$_{50}$ values based on two data points
[c]X% @ Y means X% blockage at Y $\mu$M Audiogenic Seizure Model in DBA/2 Mice A compound of the present invention was dissolved in water using 10% (weight/volume) Emulphor (GAF Corp., Wayne, N.J.) surfactant. Substances were administered by intravenous injection into the retro-orbital venous sinus of male mice (3–4 weeks old, Jackson Laboratories, Bar Harbour, Me.). All testing was preformed 15 minutes or 45 minutes after drug injection. Immediately before anticonvulsant testing, mice were placed upon a wire mesh, 4 inches square suspended from a steel rod. The square was slowly inverted through 180 degrees and mice observed for 30 seconds. Any mouse falling from the wire mesh was scored as ataxic.

Mice were placed into an enclosed acrylic plastic chamber (21 cm height, approximately 30 cm diameter) with a high-frequency speaker (4 cm diameter) in the center of the top lid. An audio signal generator (Protek model B-810) was used to produce a continuous sinusoidal tone that Was swept linearly in frequency between 8 kHz and 16 kHz once each 10 msec. The average sound pressure level (SPL) during stimulation was approximately 100 dB at the floor of the chamber. Mice were placed within the chamber and allowed to acclimatize for 1 minute. DBA/2 mice in the vehicle-treated group responded to the sound stimulus (applied until tonic extension occurred, or for a maximum of 60 sec) with a characteristic seizure sequence consisting of wild running followed by clonic seizures, and later by tonic extension, and finally by respiratory arrest and death in 80% or more of the mice. In vehicle-treated mice, the entire sequence of seizures to respiratory arrest lasts approximately 15–20 seconds.

The incidence of all the seizure phases in the drug-treated and vehicle-treated mice was recorded, and the occurrence of tonic seizures were used for calculating anticonvulsant ED$_{50}$ values by probit analysis. Mice were used only once for testing at each time and dose point. Results of this assay are shown below in Table 3.

TABLE 3

Table of Audiogenic Seizure Model in DBA/2 Mice

| Example No. | Dose (mg/Kg, IV) | Time Posttreatment (min.) | Number of Mice Protected From Tonic Convulsions* |
|---|---|---|---|
| 1 | 30 | 15 | 3/5 |
| 7 | 30 | 15 | 4/5 |
| 7 | 30 | 45 | 4/5 |
| 8 | 30 | 15 | 5/5 |
| 8 | 30 | 45 | 5/5 |
| 8 | 10 | 15 | 4/5 |
| 8 | 10 | 45 | 2/5 |
| 8 | 3 | 15 | 0/5 |
| 8 | 3 | 45 | 0/5 |
| 9 | 30 | 15 | 4/4 |

TABLE 3-continued

Table of Audiogenic Seizure Model in DBA/2 Mice

| Example No. | Dose (mg/Kg, IV) | Time Posttreatment (min.) | Number of Mice Protected From Tonic Convulsions* |
|---|---|---|---|
| 9  | 30 | 45 | 4/4 |
| 9  | 10 | 15 | 5/5 |
| 9  | 10 | 45 | 3/5 |
| 9  | 3  | 15 | 3/5 |
| 9  | 3  | 45 | 0/5 |
| 12 | 30 | 15 | 5/5 |
| 12 | 30 | 45 | 4/5 |
| 15 | 30 | 15 | 3/3 |
| 15 | 30 | 45 | 5/5 |
| 28 | 30 | 15 | 4/5 |
| 28 | 30 | 45 | 5/5 |
| 31 | 30 | 15 | 0/5 |
| 31 | 30 | 45 | 0/5 |
| 33 | 30 | 15 | 0/5 |
| 33 | 30 | 45 | 0/5 |
| 38 | 30 | 15 | 4/5 |
| 38 | 30 | 45 | 1/5 |
| 40 | 30 | 15 | 0/5 |
| 40 | 30 | 45 | 0/5 |
| 46 | 10 | 15 | 4/5 |
| 46 | 10 | 45 | 1/5 |
| 52 | 30 | 15 | 5/5 |
| 52 | 30 | 45 | 4/5 |

*Number of mice protected from tonic convulsions/Number of mice tested

Measurement of L-type $Ca^{2+}$ Channel Blocking Potencies of Compounds in A10 Cells Calcium flux through voltage-sensitive calcium channels was assessed by time-resolved monitoring of the fluorescence of pre-loaded calcium-sensitive dyes using FLIPR, a fluorescent image plate reader (Molecular Devices Co.). The A10 smooth muscle cell line derived from embryonic thoracic aorta of the DBIX rat (ATCC, CRL-1476) which endogenously expresses L-type calcium channels. The growth media for A10 cells was Ham's F12/DME high glucose (Irvine Scientific, 9052), supplemented with 20% fetal bovine serum (HyClone Labs, A-1115-L), and 1% each of L-glutamine and antibiotic-antimycotic (same source as above).

Cells were grown to confluency and replated on black-sided 96-well plates (Costar, 3603) for use in FLIPR. Two days after replating, growth media was removed and cells were loaded at 37° C. with 100 μL media containing 1 μM Oregon Green 488 Bapta-1 dye (Molecular Probes, O-6807) for 1 to 3 hours. The dye-containing media was then washed away with buffer (composition in mM: 1.25 $CaCl_2$, 1.2 $MgSO_4$, 11 glucose, 10 HEPES, 3.0 KCl, 137.0 NaCl, pH 7.4 with Tris base) in a Denley Cellwash (Labsystems, CW018B). The residual buffer volume was adjusted to 50 μL. A 5 minute drug-pre-incubation period at 35° C. was initiated when 50 μL of drug-containing buffer was pipetted into the cell plate with the 96-well pipettor integrated in the FLIPR apparatus. Fluorescent counts were monitored at 20 second intervals for 360 seconds, beginning 60 seconds prior to the delivery of drug-containing buffer. Following drug addition, 100 μL aliquots of a high $K^+$, depolarizing stimulus (composition in mM: 1.25 $CaCl_2$, 1.2 $MgSO_4$, 11 glucose, 10 HEPES, 140.0 KCl, pH 7.4 with Tris base) were added to each well, and fluorescence was monitored at 1 second intervals for 120 seconds beginning 10 seconds prior to the stimulus addition. CCD camera exposure time was 0.4 seconds, laser excitation was at 488 nm with a power of 0.2–0.5W, and a 510 to 560 nm bandpass interference filter preceded the camera.

Data was analyzed as a summation of fluorescent counts above basal during the stimulation period (an approximation of area under the curve), after normalizing the data with a spatial uniformity correction (for variations in laser illumination and cell density) and a negative control correction (zero calcium increase defined as the fluorescence reading in the presence of saturating pharmacologic block of the respective calcium channel). Drug effects were expressed as percent inhibition of fluorescence from an average of 8 $K^+$-stimulated wells which were pre-treated in the drug incubation period with buffer only. In the A10 cells, the pharmacologic agent used to define zero calcium influx was nitrendipine (RBI, N-144) at a final concentration of $1.0 \times 10^{-6}$ M.

Table of $Ca^{2+}$ Channel Blocking Potency in A10 Cells

| Example No. | FLPA10 $IC_{50}$ (μM) |
|---|---|
| 2  | 0.29 |
| 7  | 0.28 |
| 8  | 0.45 |
| 9  | 0.39 |
| 12 | 0.6 |
| 14 | >3.0 |
| 16 | 0.27 |
| 17 | 0.074 |
| 18 | 0.57 |
| 19 | 0.66 |
| 20 | 0.47 |
| 21 | 0.27 |
| 22 | 0.16 |
| 23 | 0.13 |
| 24 | 1.5 |
| 25 | 0.80 |
| 26 | 0.24 |
| 27 | 0.45 |
| 28 | 0.29 |
| 29 | 1.2 |
| 30 | 1.3 |
| 31 | 1.2 |
| 32 | 1.8 |
| 33 | 0.36 |
| 34 | 0.63 |
| 35 | 0.36 |
| 36 | 0.27 |
| 37 | 1.4 |
| 38 | 0.61 |
| 39 | 0.89 |
| 40 | 0.5 |
| 41 | 0.78 |
| 42 | 2.0 |
| 43 | 0.44 |
| 44 | 0.30 |
| 45 | 0.93 |
| 46 | 1.8 |
| 47 | 1.7 |
| 48 | 1.7 |
| 49 | 1.0 |
| 50 | 0.95 |
| 51 | 0.71 |
| 52 | 0.43 |
| 53 | 0.42 |
| 54 | 1.3 |
| 55 | 0.94 |
| 56 | >3.0 |
| 57 | >3.0 |
| 58 | >3.0 |
| 59 | >3.0 |
| 60 | 0.22 |
| 61 | 1.7 |
| 62 | 0.42 |
| 63 | 1.1 |
| 64 | 0.089 |
| 65 | 0.68 |
| 66 | 0.51 |

-continued

Table of Ca$^{2+}$ Channel Blocking Potency in A10 Cells

| Example No. | FLPA10 IC$_{50}$ ($\mu$M) |
|---|---|
| 67 | 0.14 |
| 68 | 0.53 |
| 69 | 0.4 |

Measurement of Calcium, Sodium, and Potassium Current in Superior Cervical Ganglion Cells Electrophysiological techniques were used to measure the effects of experimental compounds on voltage-gated Ca$^{2+}$, Na$^{30}$, and K$^+$ channels. Ca$^{2+}$ channel currents were measured from N-type Ca$^{2+}$ channels in cultured superior cervical ganglion (SCG) neurons. Sodium and potassium channel currents were measured from acutely dissociated SCG neurons.

Superior cervical ganglia (SCG) were isolated from 1 to 4 day Sprague-Dawley neonatal rats following sacrifice by carbon dioxide asphyxiation. Dissociation of the neurons from the ganglia was accomplished using a 30 to 45 minute treatment in 0.25% trypsin, similar to methods outlined in Higgins, et al. (see Higgins D. et al. "Tissue culture of mammalian autonomic neurons." In Banker G. and Goslin K. (Eds), *Culturing Nerve Cells*, Cambridge, Mass., MIT Press [1991]).

Ca$^{2+}$, Na$^+$, and K$^+$ channel currents in SCG neurons were measured using conventional single electrode whole-cell voltage-clamp techniques, outlined in Hamill et al., (see Hamill O. P. et al. "Improved patch-clamp techniques for high resolution current recordings from cells and cell-free membrane patches."*Pflugers Arch.*, 1981;391:85–100). For Ca$^{2+}$ channel experiments, the external bathing solution contained tetraethylammonium chloride (100 mM), choline chloride (52 mM), NaCl (15 mM), HEPES (10 mM), glucose (5.6 mM), CaCl$_2$ (2 mM), and MgCl$_2$ (0.8 mM), pH 7.35 with KOH; with the internal pipette solution containing cesium methane sulfonate (140 mM), EGTA (10 mM), and HEPES (10 mM), supplemented with 5 mM Mg$^{2+}$-ATP on the day of the experiment, pH 7.4 with CsOH. For Na$^+$ and K$^+$ channel experiments, the external bathing solution contained NaCl (150 mM), KCl (5 mM), MgCl$_2$ (1.1 mM), CaCl$_2$ (2.6 mM), Na-HEPES (10 mM), and glucose (10 mM), pH 7.4; with the internal pipette solution containing KCl (80 mM), K-gluconate (50 mM), HEPES (10 mM), and EGTA (10 mM), pH 7.4 with KOH. Experimental compounds were diluted into the external solution and applied to the soma of cells by local perfusion from large diameter (20–50 $\mu$m) glass micropipettes or from a U-tube applicator.

After obtaining a whole-cell recording, Ca$^{2+}$ channels were elicited by stepping to test potentials between −40 and +20 mV for 120 msec from the holding potential of −90 mV to determine if the amplitude of the current and clamp control were adequate for evaluation of drug effects. Ca$^{2+}$ channel currents were evoked by stepping from a holding potentials between −65 mV and −55 mV to a test potential of +20 mV for 150 msec every 40 seconds. The amplitude of the Ca$^{2+}$ channel currents were compared before and during drug application and drug effects expressed as percent inhibition of the amplitude of control currents.

For Na$^+$ and K$^+$ channel currents, following the determination of the I/V relationship for each cell in control solution, currents were evoked from a holding potential between −65 and −55 mV by stepping every 10 sec to a test potential of either 0 mV for Na$^+$ or +50 mV for K$^+$ current for a duration of 35 msec. Peak inward current was measured for Na$^+$ and sustained current for K$^+$ channel currents. After stable current amplitudes were observed in control solution, the external solution was rapidly exchanged with an external solution containing test compound. Test compounds were applied until steady-state block was achieved. Data were expressed as percent inhibition of control amplitudes for Na$^+$ and K$^+$ channel currents.

Table of Calcium, Sodium, and Potassium Current in Superior Cervical Ganglion Cells

| Example No. | SCG Ca, IC$_{50}$ ($\mu$M) | SCG K, IC$_{50}$ ($\mu$M) | SCG Na, IC$_{50}$ ($\mu$M) |
|---|---|---|---|
| 1 | 16% @ 10[a] | 3% @ 10 | 14% @ 10 |
|   | 17% @ 1 | 4.3% @ 1 |   |
| 3 | 33% @ 10 | 48% @ 10 | 5% @ 10 |
| 7 | 98% @ 10 | 90% @ 10 |   |
|   | 45% @ 1 |   |   |
| 8 | 2.4 | 50% @ 10 | 94% @ 10 |
| 9 | 53 | 9.1 | 8.5 |
| 12 | 94% @ 10 | 58% @ 10 | 87% @ 10 |
|   | 3% @ 1 | 15% @ 1 |   |
| 13 | 77% @ 10 | 48% @ 10 | 95% @ 10 |
|   | 23% @ 1 | 10% @ 1 |   |
| 14 | 8% @ 10 | −1% @ 10 |   |
| 28 | 88% @ 10 | 47% @ 10 | 90% @ 10 |
|   | 55% @ 1 | 3% @ 1 | 5% @ 1 |
| 31 | 62% @ 10[a] |   |   |
|   | 2.5% @ 1 |   |   |
| 33 | 72% @ 10 | 39% @ 10 | 22% @ 10 |
|   | 18% @ 1 |   |   |
| 36 | 81% @ 10 | 27% @ 10 | 81% @ 10 |
|   | 18% @ 1 |   |   |
| 39 | 75% @ 10 | 6% @ 1 |   |
|   | 15% @ 1 |   |   |

[a]"X% @ Y" means X% blockage at Y $\mu$M

Maximal Electroshock Testing

In this test, four representative compounds were tested for their anticonvulsant effects using the procedure described below.

Male CF-1 mice, 20 to 28 g, from Charles River Laboratories, Portage, Mich. were used in all experiments. Groups of 10 mice each were given various intravenous doses of test compound in aqueous solution with 10% Emulphan® Surfactant in a volume of 10 mL/kg of body weight. Electroshock was delivered by corneal electrodes with 60 Hz alternating current (50 mA root-mean-squared for 0.2 seconds) using a constant-current stimulator (Wahlquist Instruments, Salt Lake City, Utah). Untreated or saline-treated mice reliably had tonic extensor seizures with rearward extension of hindlimbs more than 3 seconds. These methods are similar to those published by Krall R. L.; Penry J. K.; White B. G.; and Kupferberg H. K. Antiepileptic Drug Development II. Anticonvulsant Drug Screening, *Epilepsia*, 1978; 19:409–428.

Table of Maximal Electroshock Testing

| Example No. | Dose (mg/Kg, iv) | Time Posttreatment (min.) | Number of Mice Protected from Tonic Convulsions* |
|---|---|---|---|
| 8 | 30 | 15 | 4/4 |
| 8 | 30 | 45 | 2/2 |
| 8 | 10 | 15 | 0/4 |
| 8 | 10 | 45 | 0/5 |
| 9 | 30 | 15 | 10/10 |
| 9 | 10 | 15 | 10/10 |
| 13 | 10 | 15 | 3/5 |
| 15 | 30 | 15 | 3/3 |
| 15 | 30 | 45 | 5/5 |

-continued

Table of Maximal Electroshock Testing

| Example No. | Dose (mg/Kg, iv) | Time Posttreatment (min.) | Number of Mice Protected from Tonic Convulsions* |
|---|---|---|---|
| 15 | 10 | 15 | 5/5 |
| 15 | 10 | 45 | 2/5 |

*Number of mice protected from tonic convulsions/Number of mice tested

In Vitro Protocol: FLPIMR Assays

Calcium flux through voltage-sensitive calcium channels was assessed by time-resolved monitoring of the fluorescence of pre-loaded intracellular calcium-sensitive dyes using FLIPR, a fluorescent image plate reader (Molecular Devices Co.). The IMR32 human neuroblastoma cell line (ATCC, CRL-127), expressing neuronal N-type calcium channels upon differentiation, was used for this assay. IMR32 cells were grown in MEM media (Gibco BRL, 11095-080), supplemented with 10% fetal bovine serum (Gibco BRL, 26140-087), 1% antibiotic-antimycotic (Gibco BRL, 15240-096), 1% L-glutamine (Gibco BRL, 25030-032). Cells, grown to confluency, were differentiated for a period of 7–10 days, or longer, by adding 1 mM dibutyryl cAMP (Sigma D-0627) and 2.5 $\mu$M 5-bromo-2-deoxyuridine (Sigma B-9285) to the media. The differentiation media was fed continuously to cells until the cells were used in an experiment.

Differentiated cells were removed from T150 flasks by aspirating media and adding 10 mL harvesting solution consisting of 0.5 mM EDTA in DPBS without calcium or magnesium (Gibco BRL, 14190-144). Cells were then centrifuged at 1500 rpm ($\approx$500 g) for 3 minutes in a Beckman tabletop centrifuge in order to remove the harvesting solution. Cells were resuspended in 10 mL of media containing 1 $\mu$M Oregon Green 488 Bapta-1 dye (Molecular Probes, O-6807) and placed in a 37° C. shaking waterbath for 1 hour. The dye-containing media was then diluted with 40 mL buffer (composition in mM: 1.25 $CaCl_2$, 1.2 $MgSO_4$, 11 glucose, 10 HEPES, 3.0 KCl, 137.0 NaCl, pH 7.4 with Tris base) and cells were centrifuged at 1500 rpm ($\approx$500 g) for 3 minutes. Cells were resuspended and washed a second time with 40–50 mL incubation buffer. After centrifugation, cells were resuspended and 200 $\mu$L aliquots were plated on black-sided 96-well plates (Costar, 3603) for use in FLIPR. The plates of cells were centrifuged at 750 rpm ($\approx$100 g) for 1.5 minutes to settle the cells to the bottom of the wells. Cells were given one final wash at setting BF1F in a Denley Cellwash (Labsystems, CW018B). The residual buffer volume was adjusted to 50 $\mu$L. A 5-minute drug-preincubation period at 35° C. was initiated when 50 $\mu$L of drug-containing buffer was pipetted into the cell plate with the 96-well pipettor integrated in the FLIPR apparatus. Nitrendipine, at a concentration of 4 $\mu$M, was included in this buffer, in addition to compounds of the present invention at various concentrations. IMR32 cells exhibit an L-type calcium channel component of calcium flux and nitrendipine was used to block this component. The 4 $\mu$M nitrendipine used at this step resulted in a final concentration, after stimulus addition, of 1 $\mu$M. Fluorescent counts were monitored at 20 s intervals for 360 s, beginning 60 s prior to the delivery of drug-containing buffer. Following drug addition, 100 $\mu$L aliquots of a high $K^+$, depolarizing stimulus (composition in mM: 1.25 $CaCl_2$, 1.2 $MgSO_4$, 11 glucose, 10 HEPES, 140.0 KCl, pH 7.4 with Tris base) were added to each well, and fluorescence was monitored at 1 s intervals for 120 s, beginning 10 s prior to the stimulus addition. CCD camera exposure time was 0.4 s; laser excitation was at 488 nm with a power of 0.2–0.5W; and a 510 to 560 nm bandpass interference filter preceded the camera.

Data was analyzed as a summation of fluorescent counts above basal during the stimulation period (an approximation of area under the curve), after normalizing the data with a spatial uniformity correction (for variations in laser illumination and cell density) and a negative control correction (zero calcium increase defined as the fluorescence reading in the presence of saturating pharmacologic block of the N-type calcium channel). Pharmacologic block of the N-type component in IMR32 cells was achieved with the omega-conotoxin MVIIA-like peptide, SNX-194 (Neurex Corp.), at a final concentration of $1.0 \times 10^{-6}$. A residual component of calcium flux remained in IMR32 cells in the presence of both nitrendipine and SNX-194. This component was not included in any calculations.

Drug effects were expressed as percent inhibition of fluorescence from an average of 8 $K^+$-stimulated wells which were pre-treated in the drug incubation period with buffer only. Data was analyzed using FLIPR software and Microsoft Excel spreadsheet software. The $IC_{50}$ calculations were performed with the Excel Add-In XLfit software (IDBS Ltd.).

Anti-Writhing Test in Mice (AW) Test Protocol

The purpose of this test is to evaluate drugs for analgesic-like activity. The AW test determines the effect of drugs on the response to a presumed painful stimulus in mice and is used as a preliminary in vivo procedure for the identification of potential analgesic agents.

Known analgesics with low, moderate, or high efficacy in man allow mice to tolerate intra-peritoneal administration of dilute acetic acid as evidenced by lesser incidence of writhing movements. The AW test measures the nociceptive response to acetic acid in mice and provides an objective, reliable, and quantitative estimate of efficacy and potency of potential analgesic compounds. This test serves as a preclinical predictor of analgesic activity.

Subjects are male Swiss-Webster mice (25–35 g).

Compounds are dissolved or suspended in physiological saline containing 2% Emulphor. Suspensions are subjected to ultrasonication for 3 minutes. Drug doses are expressed as the active moiety and are normally administered to mice (10, 30, and 100 mg/kg IP, SC, PO, or IM) in a volume of 10 mL/kg, 1 hour prior to testing; ICV doses (in $\mu$g/kg) are administered in a volume of 0.5 mL/kg, 5 minutes prior to testing. Animals dosed PO are fasted for 16 hours prior to dosing. Groups of eight mice are tested with each dose or the vehicle solution (control group).

Mice are treated with a dilute solution of acetic acid (0.6%, 10 mL/kg IP) which elicits writhing. In four successive trials, one pair of mice from each treatment group is placed in one of four adjacent clear plexiglas chambers (4 in×4 in×4 in). This allows the simultaneous observation of four pairs of mice representing all treatments and controls throughout the test. Writhing movements (abdominal contractions, stretching of the torso and hind legs, and concave arching of the back) are counted for 5 minutes commencing 7 minutes after acetic acid administration.

Drug effects on acetic acid-induced writhing are expressed as percent suppression of writhing relative to the vehicle-treated control group run in parallel with treated animals. The writhing tallies from pairs of animals are summed for each treatment and are divided by the summed writhing in the control group. The $ED_{50}$s for suppression of writhing are determined by nonlinear regression analysis. Each dose is assigned a rating as follows:

N=not active: 0–30% inhibition of writhing

C=moderately active: 31–60% inhibition

A=active: 61–100% inhibition

The results of this test are shown below.
In Vitro FLR IMR Results

| Example | FLP IMR IC$_{50}$ ($\mu$M) |
|---|---|
| 71 | IC$_{50}$ = 2.5 $\mu$M |
| 72 | IC$_{50}$ = 1.9 $\mu$M |
| 73 | IC$_{50}$ = 3.9 $\mu$M |
| 74 | IC$_{50}$ = 2.9 $\mu$M |
| 75 | IC$_{50}$ = 2.0 $\mu$M |
| 76 | IC$_{50}$ = 2.2 $\mu$M |
| 77 | IC$_{50}$ = 2.2 $\mu$M |
| 78 | IC$_{50}$ = 1.6 $\mu$M |

In Vivo Anti-Writhing Test Results

| Example | Anti-Writhing % Protection (dose) |
|---|---|
| 71 | 33.9% @ 10 mg/kg |
| 73 | 90.4% @ 10 mg/kg |
| 76 | 20.9% @ 10 mg/kg |
| 77 | 43.4% @ 10 mg/kg |
| 78 | 0% @ 10 mg/kg |

What is claimed is:

1. A compound having the structural Formula I

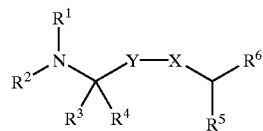

or the pharmaceutically acceptable salts, thereof, wherein

X is —NH(CH$_2$)$_3$—;

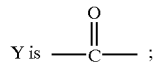

each R$^1$ and R$^2$ are independently hydrogen, C$_1$–C$_6$ alkyl, C$_2$–C$_6$ alkenyl,

—(CH$_2$)$_n$phenyl, —(CH$_2$)$_n$substituted phenyl wherein the substituents on the phenyl group are selected from the group consisting of halogen, C$_1$–C$_8$ alkyl, —CN, —CF$_3$, —NO$_2$, —NH$_2$, —NHC$_1$–C$_8$ alkyl, —N(C$_1$–C$_8$ alkyl)$_2$, —OC$_1$–C$_8$ alkyl, and —OH,

—C$_3$–C$_7$ cycloalkyl-(CH$_2$)$_n$—, C$_3$–C$_7$ heterocycle-(CH$_2$)$_n$— wherein one of C$_3$–C$_7$ is replaced with a heteroatom selected from the group consisting of N, O, or S and wherein the heterocycle is saturated or unsaturated, monocyclic or bicyclic,

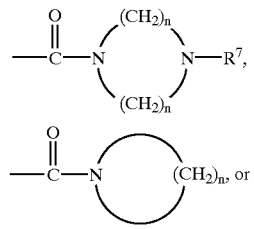

R$^1$ and R$^2$ together with the nitrogen atom to which they are both attached form a heterocycloalkyl group selected from piperidinyl and morpholinyl, with the proviso that R$^1$ and R$^2$ cannot simultaneously be hydrogen;

n is 0 to 6

R$^3$ is hydrogen, C$_1$–C$_6$ alkyl, phenyl, substituted phenyl selected from the substituents consisting of halogen, C$_1$–C$_8$ alkyl, —CN, —CF$_3$, —NO$_2$, —NH$_2$, —NHC$_1$–C$_8$ alkyl, —N(C$_1$–C$_8$ alkyl)$_2$, —OC$_1$–C$_8$ alkyl, and —OH, benzyl, substituted benzyl selected from the substituents consisting of halogen, C$_1$–C$_8$ alkyl, —CN, —CF$_3$, —NO$_2$, —NH$_2$, —NHC$_1$–C$_8$ alkyl, —N(C$_1$–C$_8$ alkyl)$_2$, —OC$_1$–C$_8$ alkyl and —OH, or —(CH$_2$)$_n$—C$_3$–C$_7$ cycloalkyl;

R$^4$ is hydrogen or C$_1$–C$_6$ alkyl, with the proviso that R$^3$ and R$^4$ cannot simultaneously be hydrogen;

or R$^3$ and R$^4$ together with the carbon atom to which they are attached form a C$_3$–C$_7$ cycloalkyl ring;

each R$^5$ and R$^6$ are substituted phenyl selected from the substituents consisting of halogen, C$_1$–C$_8$ alkyl, —CN, —CF$_3$, —NO$_2$, —NH$_2$, —NHC$_1$–C$_8$ alkyl, —N(C$_1$–C$_8$ alkyl)$_2$, —OC$_1$–C$_8$ alkyl, and —OH; and R$^7$ is C$_1$–C$_6$ alkyl, phenyl, or C$_3$–C$_7$ heterocycloalkyl wherein one of C$_3$–C$_7$ is replaced with a heteroatom selected from the group consisting of N, O, or S and wherein the heterocycle is saturated or unsaturated, monocyclic or bicyclic.

2. A compound according to claim 1 wherein R$^1$ is hydrogen and R$^2$ is

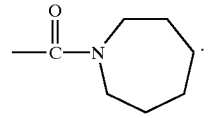

3. A compound according to claim 1 wherein R$^3$ is hydrogen and R$^4$ is 2-methyl propyl.

4. A compound according to claim 1 wherein R$^5$ and R$^6$ are 4-fluorophenyl.

5. A compound according to claim 1 wherein R$^5$ and R$^6$ are 4-fluorophenyl; X is —NHCH$_2$CH$_2$CH$_2$—; R$^3$ is hydrogen; and R$^4$ is 2-methylpropyl.

6. A compound according to claim 1 wherein R$^1$ is hydrogen;

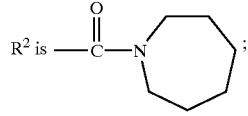

and

R$^3$ and R$^6$ are 4-fluorophenyl.

7. The compound (S)-(1-{4-[Bis-(4-fluoro-phenyl)-methyl]-piperazin-1-ylmethyl}-3-methyl-butyl)-carbamic acid tert-butyl ester.

8. The compound
(S)-Azepane-1-carboxylic acid {1-[4,4-bis-(4-fluoro-phenyl)-butylcarbamoyl]-3-methyl-butyl}-amide;
(R)-Azepane-1-carboxylic acid {1-[4,4-bis-(4-fluoro-phenyl)-butylcarbamoyl]-3-methyl-butyl}-amide;
(S)-{1-[4,4-Bis-(4-fluoro-phenyl)-butylcarbamoyl]-3-methyl-butyl}-carbamic acid tert-butyl ester;
(S)-2-Amino-4-methyl-pentanoic acid [4,4-bis-(4-fluoro-phenyl)-butyl]-amide;
(S)-2-(Cyclohexylmethyl-amino)-4-methyl-pentanoic acid [4,4-bis-(4-fluoro-phenyl)-butyl]-amide;
(S)-4-Methyl-2-(3-methyl-but-2-enylamino)-pentanoic acid [4,4-bis-(4-fluoro-phenyl)-butyl]-amide;
(S)-4-Methyl-2-methylamino-pentanoic acid [4,4-bis-(4-fluoro-phenyl)-butyl]-amide;
(S)-4-Methyl-2-[methyl-(3-methyl-but-2-enyl)-amino]-pentanoic acid [4,4-bis-(4-fluoro-phenyl)-butyl]-amide; or
(S)-2-[(4-tert-Butyl-benzyl)-methyl-amino]-4-methyl-pentanoic acid [4,4-bis-(4-fluoro-phenyl)-butyl]-amide.

9. The compound:
(S)-2-Cyclohexylamino-4-methyl-pentanoic acid [4,4-bis-(4-fluoro-phenyl)-butyl]-amide;
(S)-Azepane-1-carboxylic acid {1-[4,4-bis-(4-fluoro-phenyl)-butylcarbamoyl]-2-methyl-butyl}-amide;
(S)-4-Phenyl-piperazine-1-carboxylic acid {1-[4,4-bis-(4-fluoro-phenyl)-butylcarbamoyl]-3-methyl-butyl}-amide;
(S)-4-Methyl-2-(tetrahydro-pyran-4-ylamino)-pentanoic acid [4,4-bis-(4-fluoro-phenyl)-butyl]-amide;
(S)-2-Isopropylamino-4-methyl-pentanoic acid [4,4-bis-(4-fluoro-phenyl)-butyl]-amide;
(S)-2-Dimethylamino-4-methyl-pentanoic acid [4,4-bis-(4-fluoro-phenyl)-butyl]-amide;
(S)-2-(Cyclohexyl-methyl-amino)-4-methyl-pentanoic acid [4,4-bis-(4-fluoro-phenyl)-butyl]-amide;
(S)-4-Methyl-2-piperidin-1-yl-pentanoic acid [4,4-bis-(4-fluoro-phenyl)-butyl]-amide;
(S)-4-Methyl-2-morpholin-4-yl-pentanoic acid [4,4-bis-(4-fluoro-phenyl)-butyl]-amide; or
(S)-4-Methyl-2-piperidin-1-yl-pentanoic acid (3,3-diphenyl-propyl)-amide.

10. The compound
(S)-Azepane-1-carboxylic acid {1-[4,4-bis-(4-fluoro-phenyl)-butylcarbamoyl]-2-methyl-propyl}-amide;
(S)-4-Methyl-2-[methyl-(tetrahydro-pyran-4-yl)-amino]-pentanoic acid [4,4-bis-(4-fluoro-phenyl)-butyl]-amide;
(S)-4-Methyl-2-[methyl-(3-methyl-butyl)-amino]-pentanoic acid [4,4-bis-(4-fluoro-phenyl)-butyl]-amide;
(S)-4-Methyl-piperazine-1-carboxylic acid {1-[4,4-bis-(4-fluoro-phenyl)-butylcarbamoyl]-3-methyl-butyl}-amide; or
(S)-Azepane-1-carboxylic acid {1-[4,4-bis-(4-fluoro-phenyl)-butylcarbamoyl]-ethyl}-amide.

11. The compound:
S-N-[4,4-Bis-(4-fluoro-phenyl)-butyl]-2-isopropylamino-3-methyl-butyramide;
S-N-[4,4-Bis-(4-fluoro-phenyl)-butyl]-2-sec-butylamino-3-methyl-butyramide;
S-2-(Isopropyl-methyl-amino)-4-methyl-pentanoic acid [4,4-bis-(4-fluoro-phenyl)-butyl]-amide;
S-N-[4,4-Bis-(4-fluoro-phenyl)-butyl]-2-(cyclohexyl-methyl-amino)-3-methyl-butyramide; or
S-N-[4,4-Bis-(4-fluoro-phenyl)-butyl]-2-cyclohexylamino-3-methyl-butyramide.

12. the compound:
(R)-4-methyl-2-methylamino-pentanoic acid [4,4-bis-(4-fluorophenyl)-butyl]-amide;
(S)-2-Hydroxy-4-methyl-pentanoic acid [4,4-bis-(4-fluorophenyl)-butyl]-amide;
(S)-3-Methyl-2-methylamino-butanoic acid [4,4-bis-(4-fluorophenyl)-butyl]-amide;
N-[4,4-Bis-(4-fluoro-phenyl)-butyl]-2-methylamino-acetamide;
(S)-4-Ethyl-2-methylamino-pentanoic acid [4,4-bis-(4-fluorophenyl)butyl]-amide;
(S)-$N^1$-[4,4-Bis-(4-fluoro-phenyl)-butyl]-4-$N^2$-dimethyl-pentane-1,2-diamine;
(R)-$N^1$-[4,4-Bis-(4-fluoro-phenyl)-butyl]-4-$N^2$-dimethyl-pentane-1,2-diamine;
N-[4,4-Bis-(4-fluoro-phenyl)-butyl]-2-(isobutyl-methyl-amino)-acetamide; or
(R)-N-[4,4-Bis-(4-fluoro-phenyl)-butyl]-2-methylamino-propionamide.

13. The compound:
(S){1-[4,4-Bis-(4-fluoro-phenyl)-butylcarbamoyl]-2-methyl-propyl}-methyl-carbamic acid tert-butyl ester;
(S)N-[4,4-Bis-(4-fluoro-phenyl)-butyl]-3-methyl-2-methylamino-butyramide;
(S){1-[4,4-Bis-(4-fluoro-phenyl)-butylcarbamoyl]-2-methyl-butyl}-methyl-carbamic acid tert-butyl ester;
(S)3-Methyl-2-methylamino-pentanoic acid [4,4-bis-(4-fluoro-phenyl)-butyl]-amide;
(S){1-[4,4-Bis-(4-fluoro-phenyl)-butylcarbamoyl]-ethyl}-methyl-carbamic acid tert-butyl ester;
(S)N-[4,4-Bis-(4-fluoro-phenyl)-butyl]-2-methylamino-propionamide;
(S){1-[4,4-Bis-(4-fluoro-phenyl)-butylcarbamoyl]-2-cyclohexyl-ethyl}-methyl-carbamic acid tert-butyl ester;
(S)N-[4,4-Bis-(4-fluoro-phenyl)-butyl]-3-cyclohexyl-2-methylamino-propionamide;
(S){1-[4,4-Bis-(4-fluoro-phenyl)-butylcarbamoyl]-2-cyclohexyl-ethyl}-carbamic acid tert-butyl ester;
(S)2-Amino-N-[4,4-bis-(4-fluoro-phenyl)-butyl]-3-cyclohexyl-propionamide;
{1-[4,4-Bis-(4-fluoro-phenyl)-butylcarbamoyl]-cyclohexyl}-carbamic acid tert-butyl ester;
1-Amino-cyclohexanecarboxylic acid [4,4-bis-(4-fluoro-phenyl)-butyl]-amide;
{1-[4,4-Bis-(4-fluoro-phenyl)-butylcarbamoyl]-cyclohexyl}-methyl-carbamic acid tert-butyl ester;
1-Methylamino-cyclohexanecarboxylic acid [4,4-bis-(4-fluoro-phenyl)-butyl]-amide;
{1-[4,4-Bis-(4-fluoro-phenyl)-butylcarbamoyl]-cyclopentyl}-carbamic acid benzyl ester; or
1-Amino-cyclopentanecarboxylic acid [4,4-bis-(4-fluoro-phenyl)-butyl]-amide.

14. A method of treating an N-type calcium channel mediated affliction selected from the group consisting of stroke, cerebral ischemia, head trauma, epilepsy and pain, the method comprising administering to a patient in need thereof a therapeutically effective amount of a compound according to claim 1.

15. The method according to claim 14, wherein the affliction is stroke.

16. The method according to claim 14, wherein the affliction is cerebral ischemia.

17. The method according to claim 14, wherein the affliction is head trauma.

18. The method according to claim 14, wherein the affliction is epilepsy.

19. The method according to claim 14, wherein the affliction is pain.

20. a pharmaceutical composition comprising a compound of claim 1 and a pharmaceutically acceptable carrier.

* * * * *